(12) United States Patent
Khan

(10) Patent No.: US 11,426,176 B2
(45) Date of Patent: Aug. 30, 2022

(54) CARTRIDGE WITH MULTI-CLIP DISPENSING PROVISIONS

(71) Applicant: Mubashir H. Khan, Springfield, MO (US)

(72) Inventor: Mubashir H. Khan, Springfield, MO (US)

(*) Notice: Subject to any disclaimer, the term of this patent is extended or adjusted under 35 U.S.C. 154(b) by 568 days.

(21) Appl. No.: 16/371,387

(22) Filed: Apr. 1, 2019

(65) Prior Publication Data

US 2019/0231357 A1    Aug. 1, 2019

Related U.S. Application Data

(63) Continuation-in-part of application No. 14/834,186, filed on Aug. 24, 2015, now abandoned, which is a continuation-in-part of application No. 14/721,312, filed on May 26, 2015, now abandoned, and a continuation-in-part of application No. 14/276,513, filed on May 13, 2014, now abandoned.

(60) Provisional application No. 62/081,755, filed on Nov. 19, 2014, provisional application No. 62/076,149, filed on Nov. 6, 2014, provisional application No. 62/073,664, filed on Oct. 31, 2014, provisional application No. 62/040,908, filed on Aug. 22, 2014, provisional application No. 62/016,717, filed on Jun. 25, 2014, provisional application No. 62/002,691, filed on May 23, 2014, provisional application No. 61/961,842, filed on Oct. 24, 2013, provisional application No. 61/957,306, filed on Jun. 29, 2013, (Continued)

(51) Int. Cl.
*A61B 17/128* (2006.01)
*A61B 17/122* (2006.01)
*A61B 17/068* (2006.01)
*A61B 17/064* (2006.01)
*A61B 17/00* (2006.01)

(52) U.S. Cl.
CPC ........ *A61B 17/1285* (2013.01); *A61B 17/064* (2013.01); *A61B 17/068* (2013.01); *A61B 17/122* (2013.01); *A61B 2017/0034* (2013.01); *A61B 2017/0641* (2013.01); *A61B 2017/0645* (2013.01); *A61B 2017/0647* (2013.01); *A61B 2017/0688* (2013.01)

(58) Field of Classification Search
CPC . A61B 17/122; A61B 17/128; A61B 17/1285; A61B 17/1222; A61B 17/1227; A61B 17/10; A61B 17/105; A61B 17/068; A61B 17/0682; A61B 16/0686; A61B 17/07207; A61B 2017/1225; A61B 2017/0688
See application file for complete search history.

(56) References Cited

U.S. PATENT DOCUMENTS 188,355 A    3/1877  Goddu ..................... 411/445
711,169 A   10/1902  LeBlanc ................... 74/127
(Continued)

FOREIGN PATENT DOCUMENTS

GB          1 452 185      5/1974  ............ A61B 17/42

*Primary Examiner* — Katherine H Schwiker

(57) ABSTRACT

An endoscopic surgical apparatus is configured to be loaded with a replaceable cartridge. The cartridge is loaded with a single-file line-up of a series of endoscopic clips. The endoscopic surgical apparatus is furthermore configured to apply (ie., dispense) each clip serially in the line-up, one clip at a time, wherever and whenever the user (eg., surgeon) chooses.

20 Claims, 58 Drawing Sheets

Related U.S. Application Data provisional application No. 61/855,313, filed on May 14, 2013.

(56) References Cited

U.S. PATENT DOCUMENTS

| | | | |
|---|---|---|---|
| 861,188 A | 7/1907 | Jones | 411/446 |
| 1,031,431 A | 7/1912 | Dunn | 411/448 |
| 1,878,053 A | 9/1932 | Winger | 192/44 |
| 2,277,931 A | 3/1942 | Moe | 411/444 |
| 2,487,803 A | 11/1949 | Heimann | 411/517 |
| 2,597,344 A | 5/1952 | Lang | 411/449 |
| 2,631,584 A | 3/1953 | Purificato | 606/68 |
| 3,051,499 A | 8/1962 | Minegishi | 277/481 |
| 3,086,208 A | 4/1963 | Eby | 206/339 |
| 3,098,232 A | 7/1963 | Brown | 606/143 |
| 3,498,175 A | 3/1970 | Goodstein | 411/548 |
| 3,958,576 A | 4/1976 | Komiya | 606/142 |
| 4,246,903 A | 1/1981 | Larkin | 606/143 |
| 4,265,226 A | 5/1981 | Cassimally | 606/221 |
| 4,512,345 A | 4/1985 | Green | A61B 17/128 |
| 4,557,263 A | 12/1985 | Green | 606/143 |
| 4,589,416 A | 5/1986 | Green | 606/220 |
| 4,719,917 A | 1/1988 | Barrows et al. | 606/220 |
| 4,796,627 A | 1/1989 | Tucker | 606/143 |
| 4,905,691 A | 3/1990 | Rydell | 606/47 |
| 5,049,152 A | 9/1991 | Simon et al. | 602/143 |
| 5,122,147 A | 6/1992 | Sewell | 606/110 |
| 5,156,609 A | 10/1992 | Nakao | A61B 17/0682 |
| 5,242,456 A | 3/1993 | Nash | 606/139 |
| 5,207,692 A | 5/1993 | Kraus | 227/901 |
| 5,282,808 A | 2/1994 | Kovac et al. | 606/143 |
| 5,304,183 A | 4/1994 | Gourlay | A61B 17/00234 |
| 5,336,227 A | 8/1994 | Nakao | 600/106 |
| 5,340,360 A | 8/1994 | Stefanchik | 606/142 |
| 5,354,304 A | 10/1994 | Allen | A61B 17/22 |
| 5,366,459 A | 11/1994 | Yoon | 606/151 |
| 5,433,721 A | 7/1995 | Hoven et al. | 606/143 |
| 5,462,558 A | 10/1995 | Kolesa et al. | 606/139 |
| 5,486,182 A | 1/1996 | Nakao | 600/37 |
| 5,535,759 A | 7/1996 | Wilk | 128/898 |
| 5,547,474 A | 8/1996 | Kloeckl | 606/143 |
| 5,626,585 A | 5/1997 | Mittelstadt et al. | 606/143 |
| 5,746,747 A | 5/1998 | McKeating | 606/110 |
| 5,772,379 A | 6/1998 | Evensen | 411/442 |
| 5,814,052 A | 9/1998 | Nakao | 606/110 |
| 5,846,248 A | 12/1998 | Chu | 606/113 |
| 5,906,620 A | 5/1999 | Nakao | 606/113 |
| 6,010,512 A | 1/2000 | Chu | 606/113 |
| 6,015,415 A | 1/2000 | Avallanet | 606/110 |
| 6,071,233 A | 6/2000 | Ishikawa | 600/104 |
| 6,090,129 A | 7/2000 | Ouchi | 606/221 |
| 6,171,315 B1 | 1/2001 | Chu | 606/113 |
| 6,352,541 B1 | 3/2002 | Keinzle | A61B 17/1285 |
| 6,375,661 B2 | 4/2002 | Chu | 606/113 |
| 6,599,298 B1 | 7/2003 | Forster et al. | 606/139 |
| 6,616,654 B2 | 9/2003 | Mollenauer | 606/110 |
| 6,616,659 B1 | 9/2003 | de la Torre | 128/898 |
| 6,679,892 B2 | 1/2004 | Guido | 606/113 |
| 6,843,794 B2 | 1/2005 | Sixto, Jr. et al. | 605/142 |
| 7,001,399 B2 | 2/2006 | Damarati | 606/143 |
| 7,044,947 B2 | 5/2006 | de la Torre | 128/898 |
| 7,081,121 B2 | 7/2006 | Muramatsu et al. | 606/142 |
| 7,094,245 B2 | 8/2006 | Adams et al. | 606/142 |
| 7,223,271 B2 | 6/2007 | Muramatsu et al. | 606/143 |
| 7,285,115 B2 | 10/2007 | Terakura | 606/1 |
| 7,635,374 B2 | 12/2009 | Monassevitch | 600/104 |
| 7,648,514 B1 | 1/2010 | Nakao | 606/142 |
| 7,740,639 B2 | 6/2010 | Hummel | 606/139 |
| 8,070,756 B2 | 12/2011 | Secrest | 600/564 |
| 8,080,021 B2 | 12/2011 | Griego | 606/143 |
| 8,123,795 B1 | 2/2012 | Knodel et al. | 623/1.23 |
| 8,407,875 B2 | 4/2013 | Gray et al. | 29/268 |
| 8,439,245 B2 | 5/2013 | Knodel et al. | 227/175.1 |
| 8,631,992 B1 | 1/2014 | Hausen et al. | 227/179.1 |
| 8,652,146 B2 | 2/2014 | Hewitt | 606/113 |
| 8,679,155 B2 | 3/2014 | Knodel et al. | 606/219 |
| 8,979,836 B2 | 3/2015 | Fischer | 606/41 |
| 9,463,039 B2 | 10/2016 | Kuroda | |
| 2001/0000348 A1 | 4/2001 | Chu | 606/113 |
| 2002/0091399 A1 | 7/2002 | Shlomo | A61B 17/0057 |
| 2002/0133178 A1 | 9/2002 | Muramatsu | A61B 17/1227 |
| 2003/0023237 A1 | 1/2003 | Mollenauer | 606/27 |
| 2003/0065335 A1 | 4/2003 | Guido | 606/144 |
| 2003/0083677 A1* | 5/2003 | Damarati | A61B 17/122 606/151 |
| 2003/0236535 A1 | 12/2003 | Onuki | 606/144 |
| 2004/0044335 A1 | 3/2004 | de la Torre | 606/27 |
| 2004/0225183 A1 | 11/2004 | Michlitsch | A61B 1/00135 |
| 2005/0107807 A1 | 5/2005 | Nakao | A61B 17/122 |
| 2005/0107809 A1 | 5/2005 | Litscher et al. | 606/142 |
| 2005/0209590 A1 | 9/2005 | Terakura | 606/47 |
| 2005/0216036 A1 | 9/2005 | Nakao | A61B 17/068 |
| 2006/0235433 A1 | 10/2006 | Secrest | 606/114 |
| 2006/0253128 A1 | 11/2006 | Sekine | 606/139 |
| 2006/0271072 A1 | 11/2006 | Hummel | 606/142 |
| 2008/0208217 A1 | 8/2008 | Adams | 606/143 |
| 2008/0255427 A1 | 10/2008 | Satake et al. | 600/204 |
| 2009/0069805 A1 | 3/2009 | Fischer | 606/42 |
| 2009/0105533 A1 | 4/2009 | Fujita | A61B 17/1227 |
| 2009/0131749 A1 | 5/2009 | Ahmed | 600/106 |
| 2010/0044251 A1 | 2/2010 | Itoh | A61B 17/1227 |
| 2010/0049217 A1 | 2/2010 | Matsuoka | A61B 17/1227 |
| 2010/0292715 A1 | 11/2010 | Nering | A61B 17/064 |
| 2011/0112434 A1 | 5/2011 | Ghabrial | 600/564 |
| 2011/0184429 A1 | 7/2011 | Saldinger | 606/113 |
| 2011/0224492 A1 | 9/2011 | Stern | 600/153 |
| 2011/0313437 A1 | 12/2011 | Yeh | A61B 17/122 |
| 2012/0029526 A1 | 2/2012 | Hewitt | 606/113 |
| 2012/0226287 A1 | 9/2012 | Qadeer | 606/113 |
| 2013/0131688 A1 | 5/2013 | Schwartz | 606/113 |
| 2013/0211432 A1 | 8/2013 | Terada | A61B 17/122 |
| 2013/0331854 A1 | 12/2013 | Saldinger | 606/113 |
| 2014/0074143 A1 | 3/2014 | Fitzgerald | A61B 17/10 |
| 2015/0032119 A1 | 1/2015 | Kuroda | 606/113 |
| 2015/0272588 A1 | 10/2015 | Khan | 606/130 |
| 2015/0374392 A1 | 12/2015 | Khan | 606/113 |
| 2016/0095598 A1 | 4/2016 | Khan | 606/143 |
| 2016/0354070 A1 | 12/2016 | Motai | A61B 18/1477 |
| 2018/0250011 A1 | 9/2018 | Khan | A61B 17/1285 |

* cited by examiner

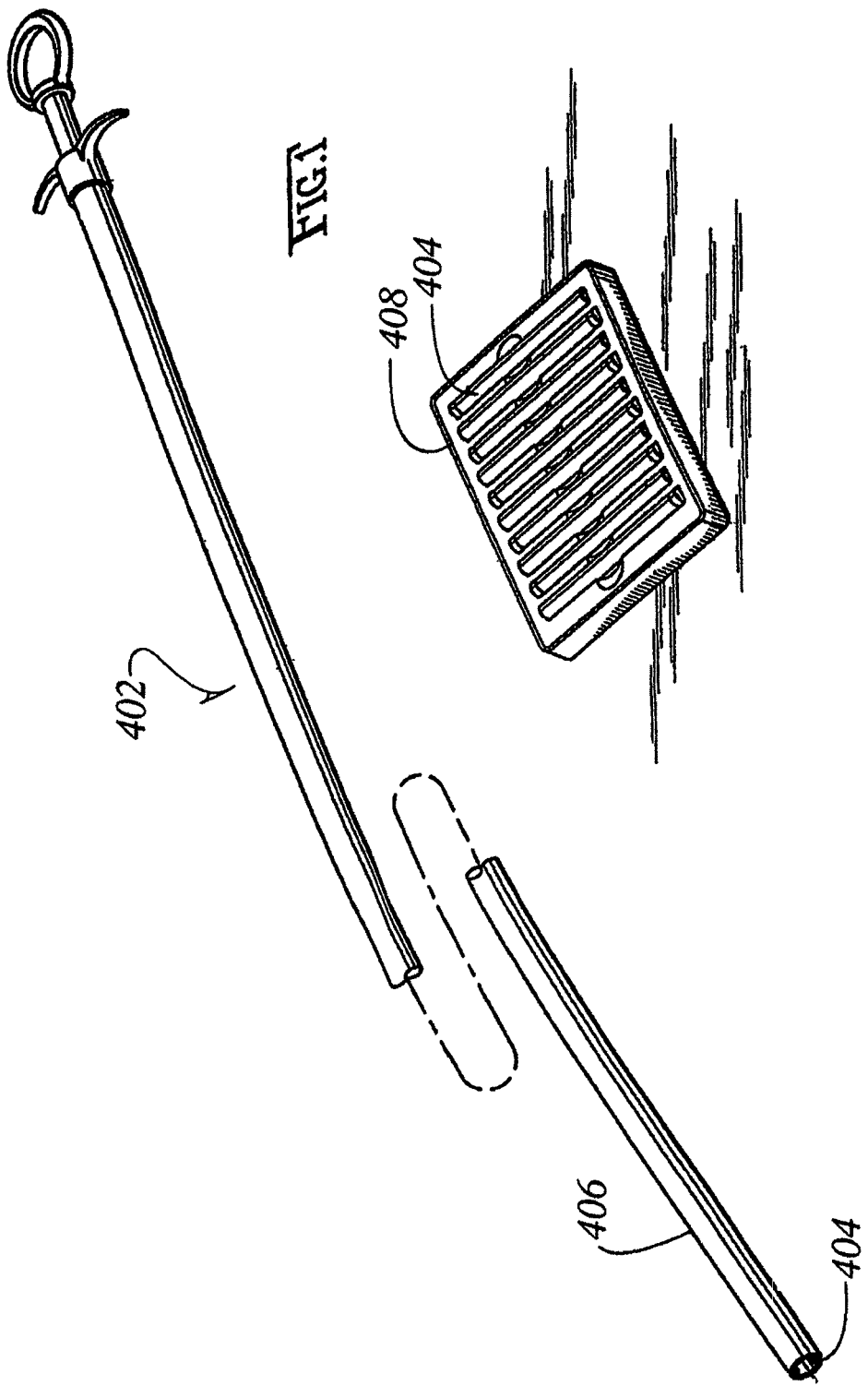

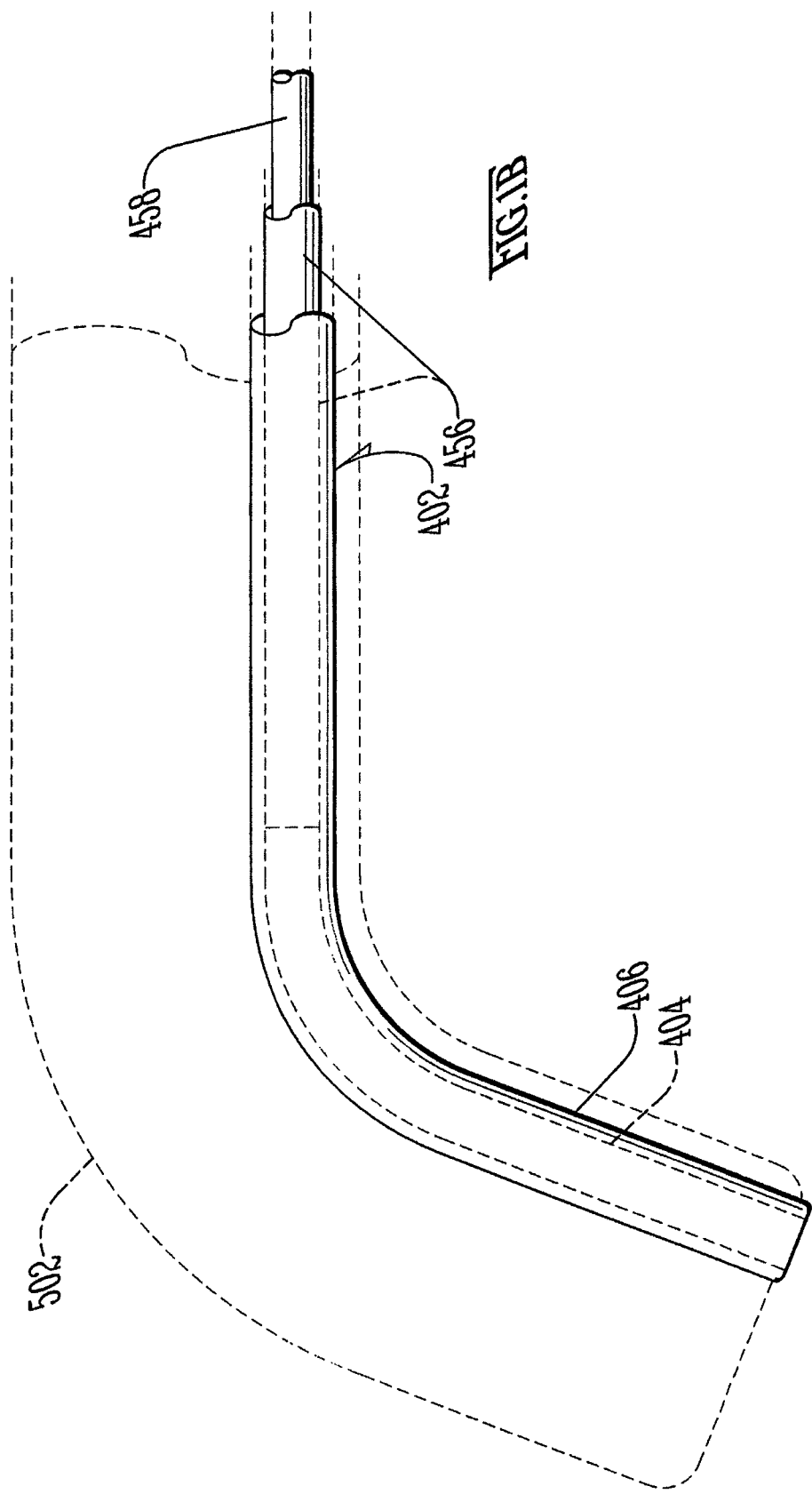

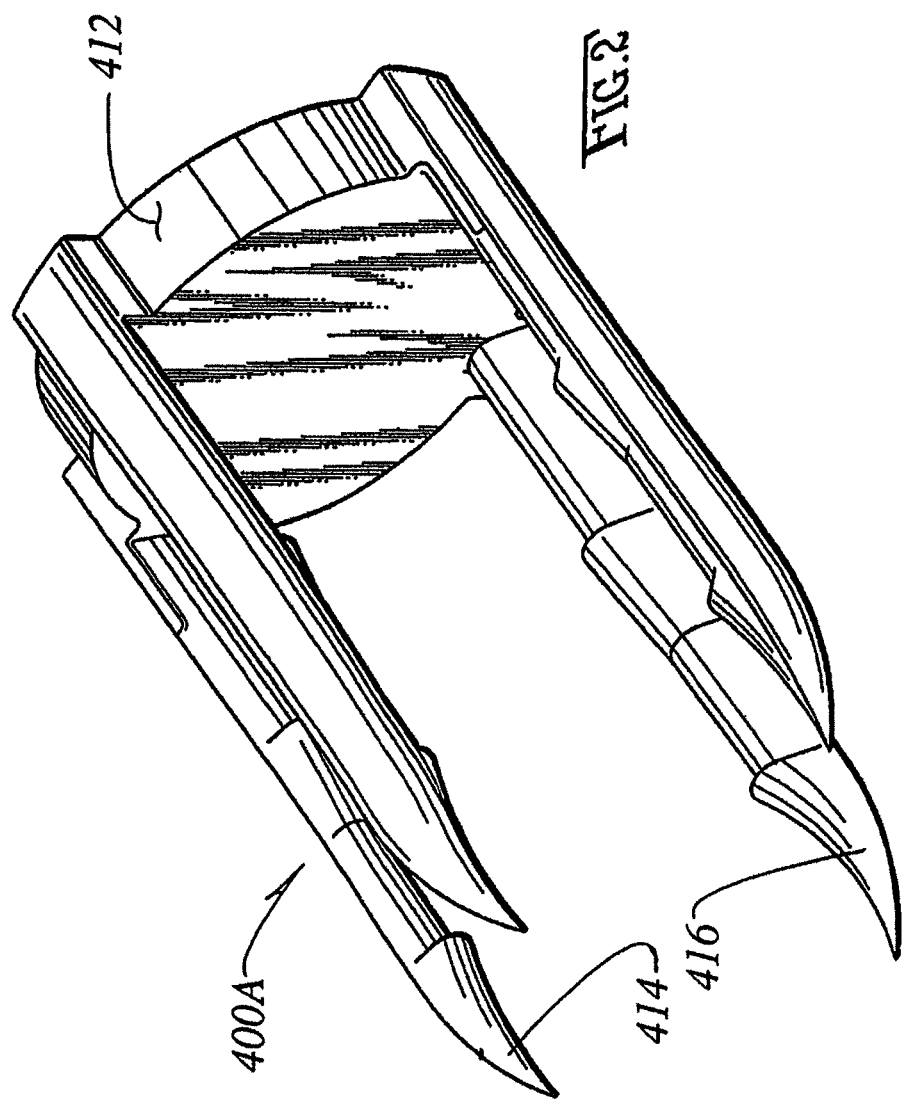

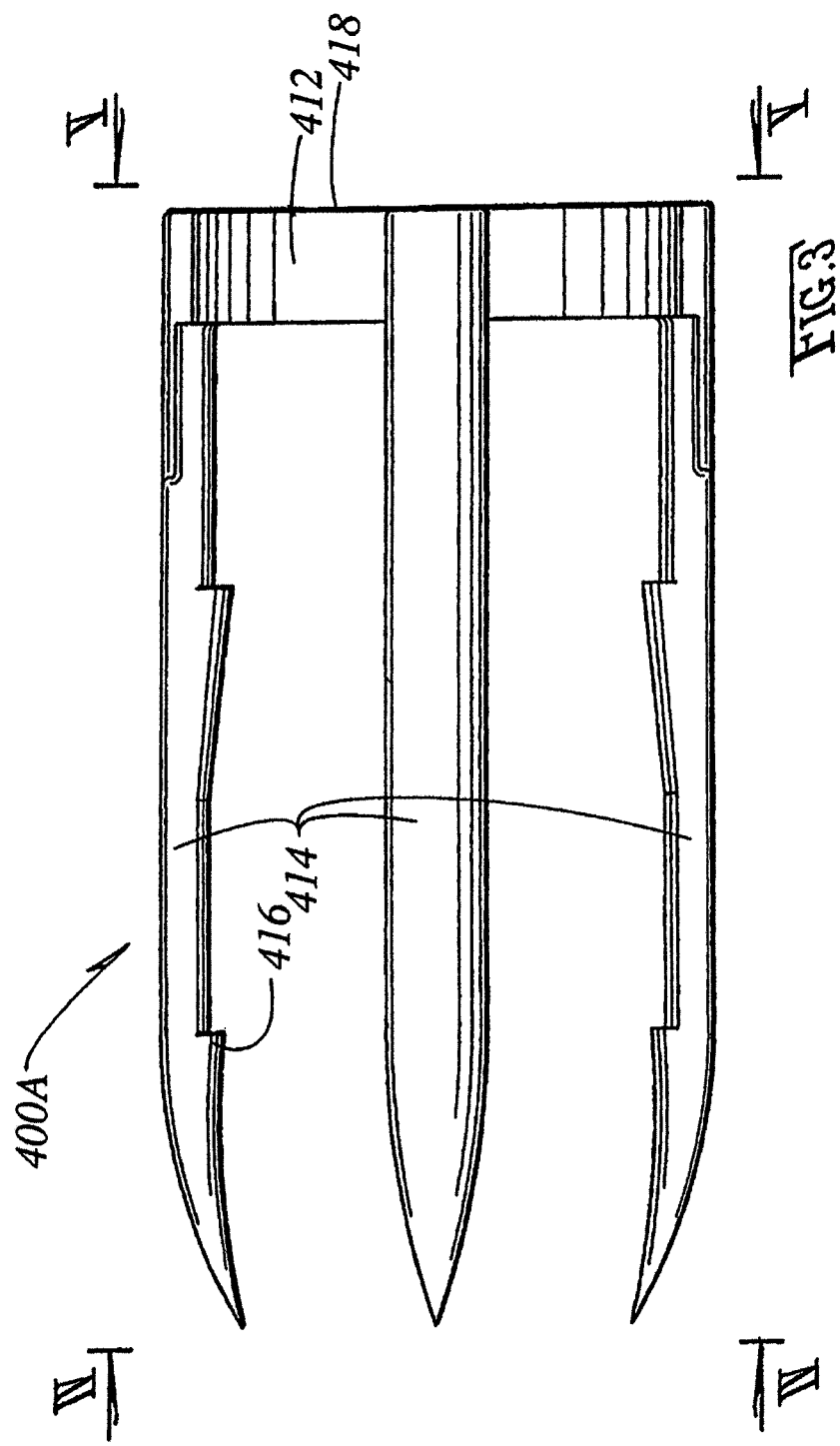

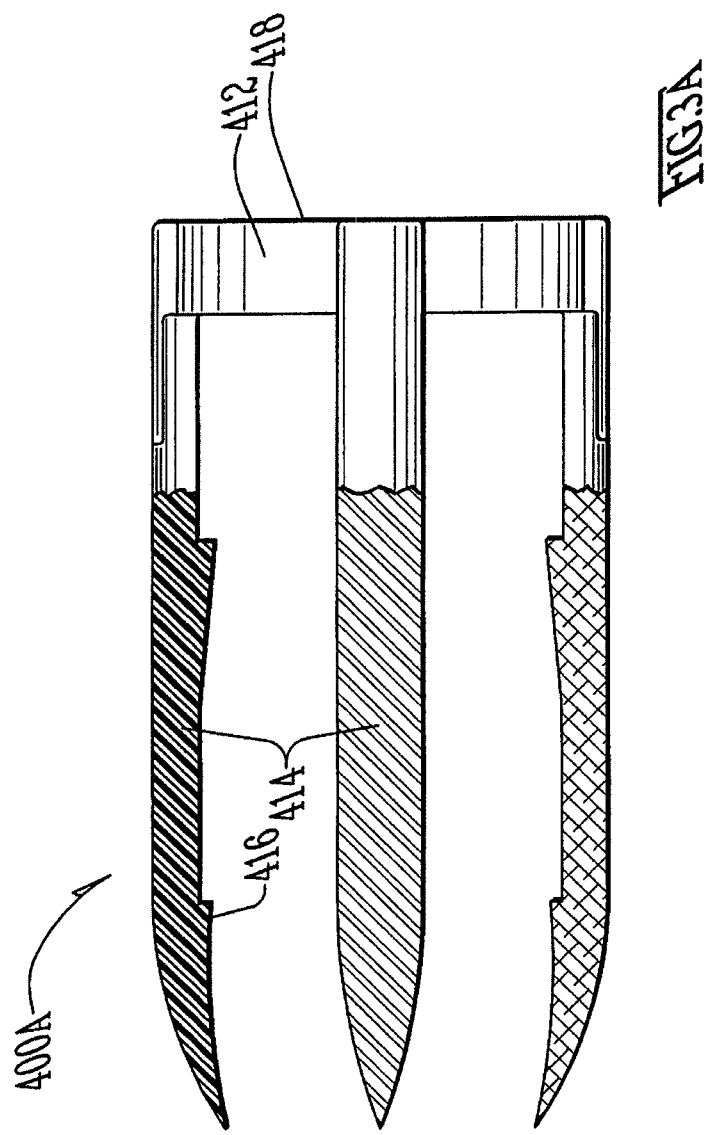

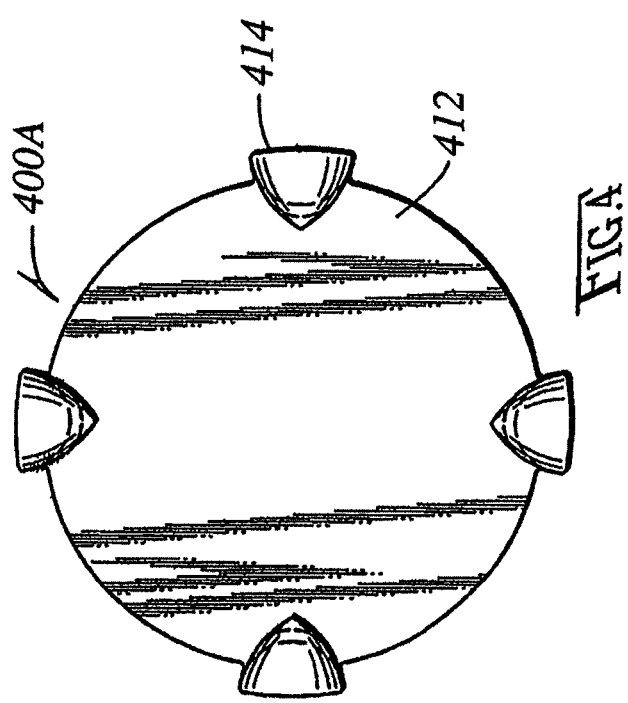
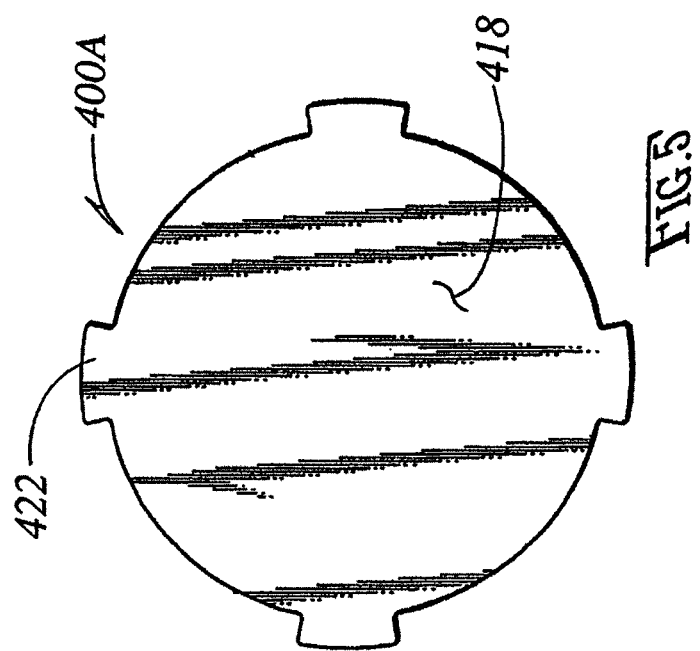

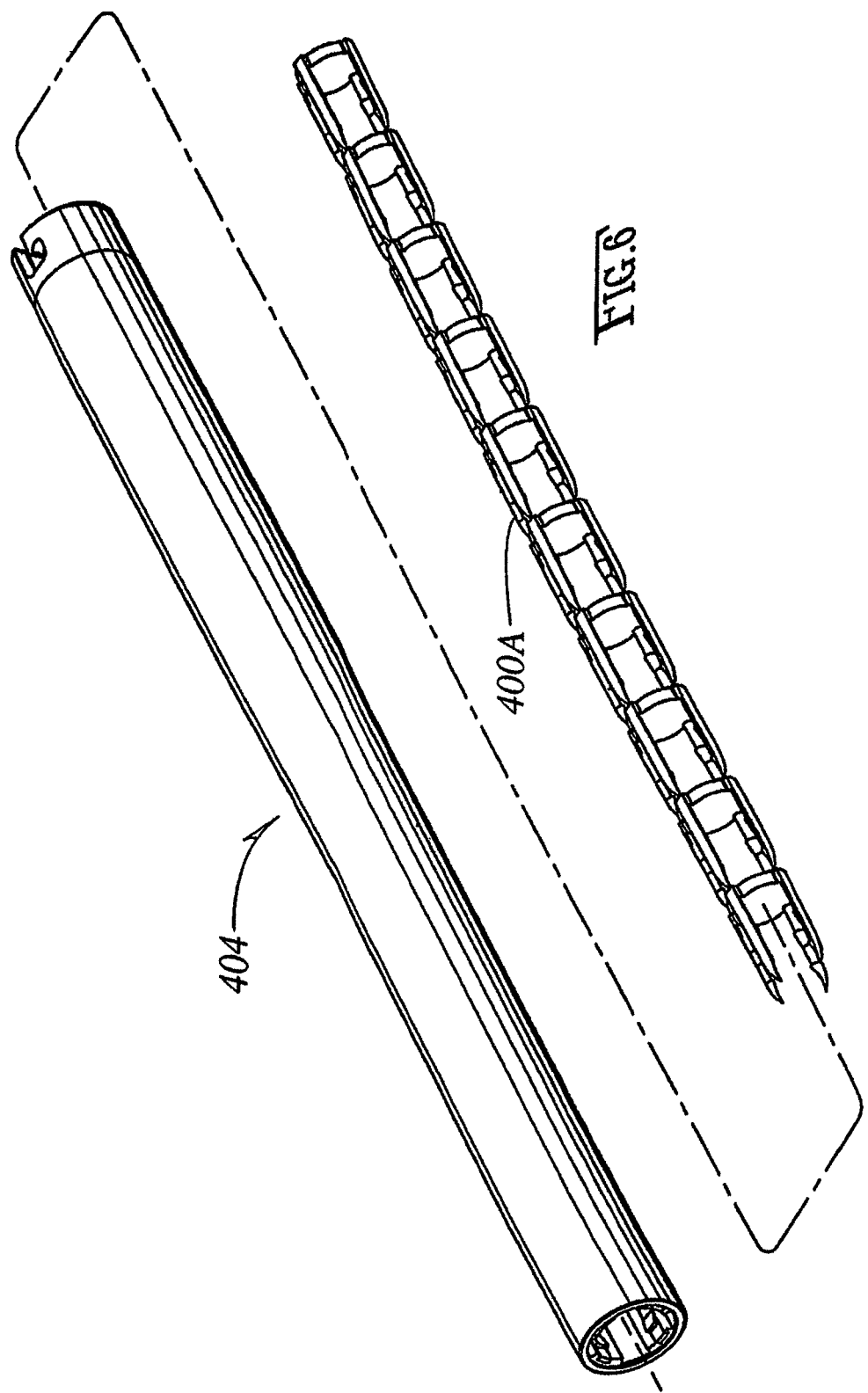

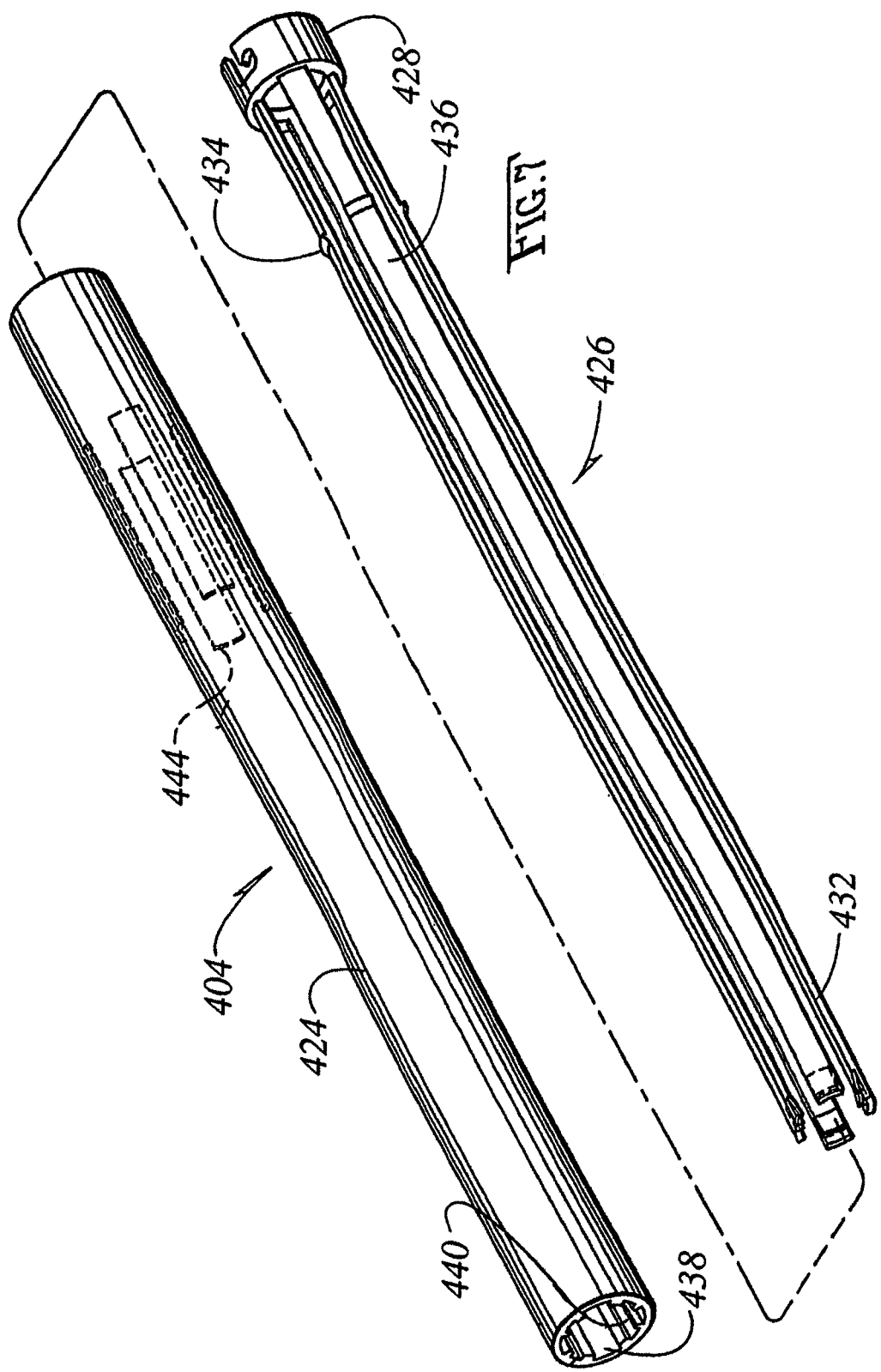

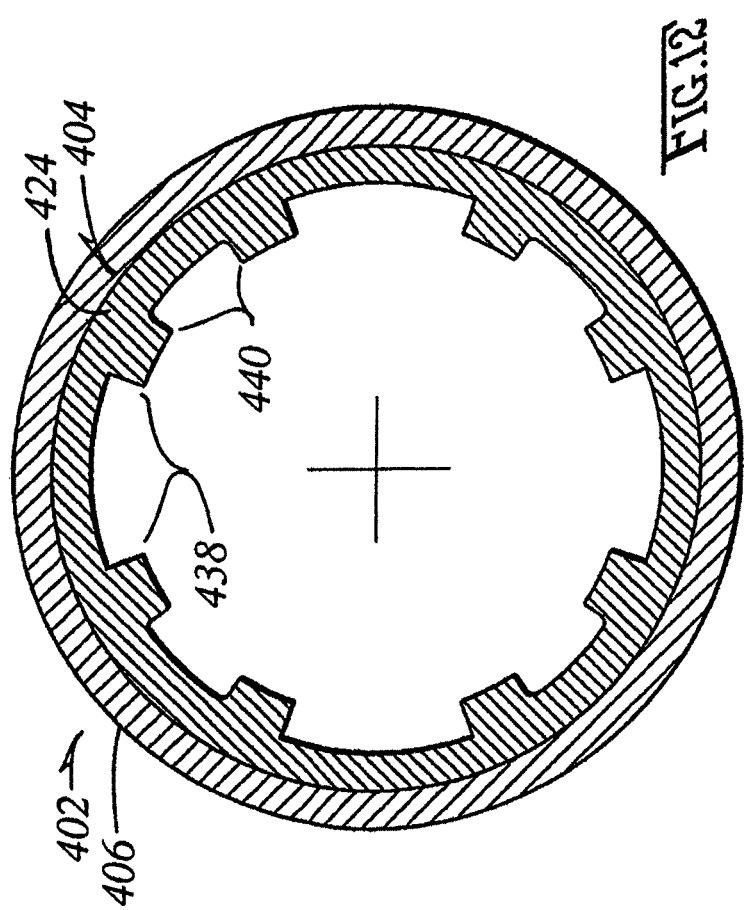

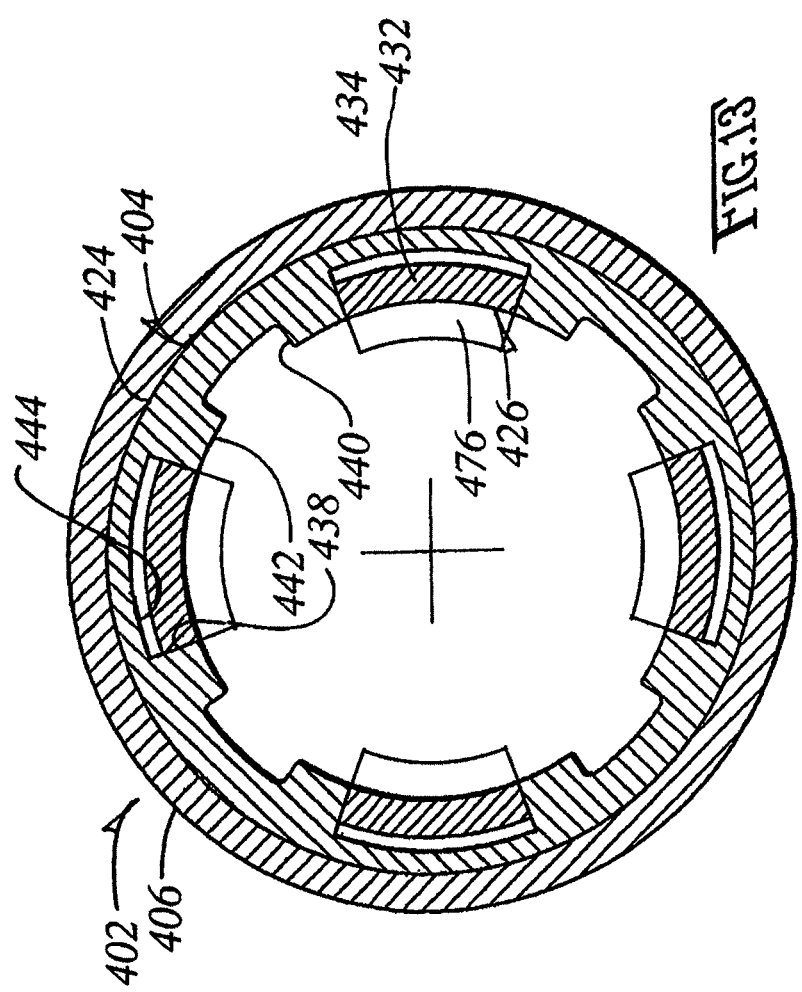

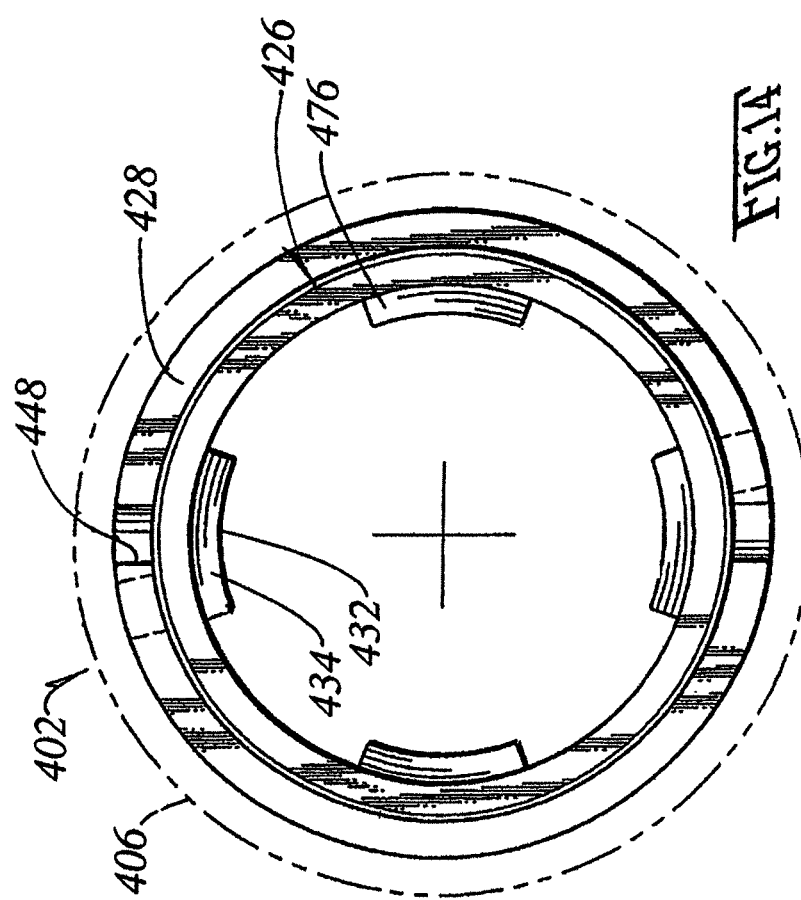

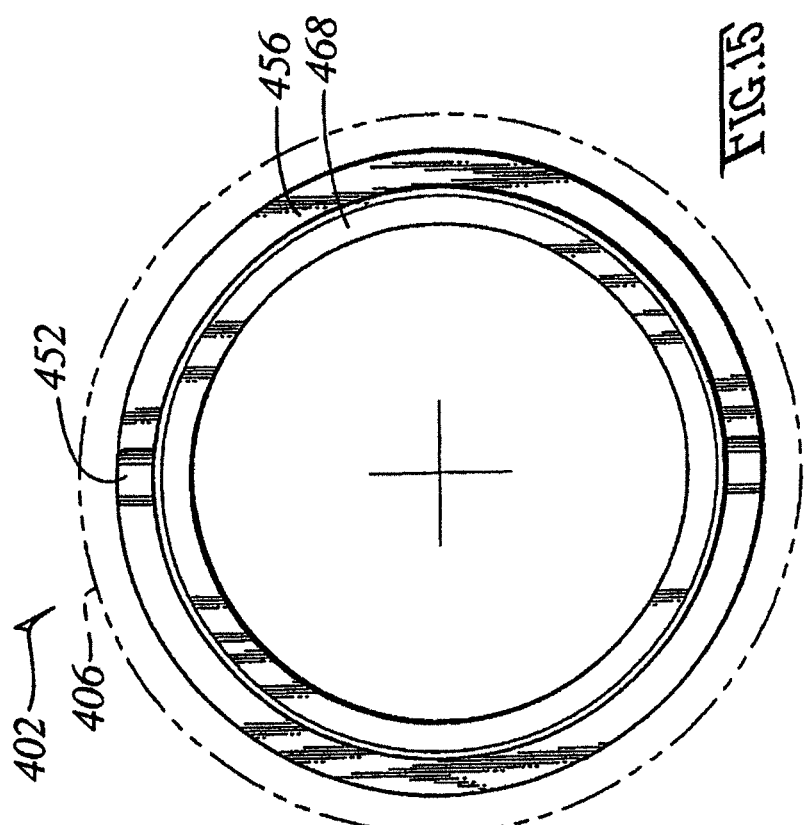

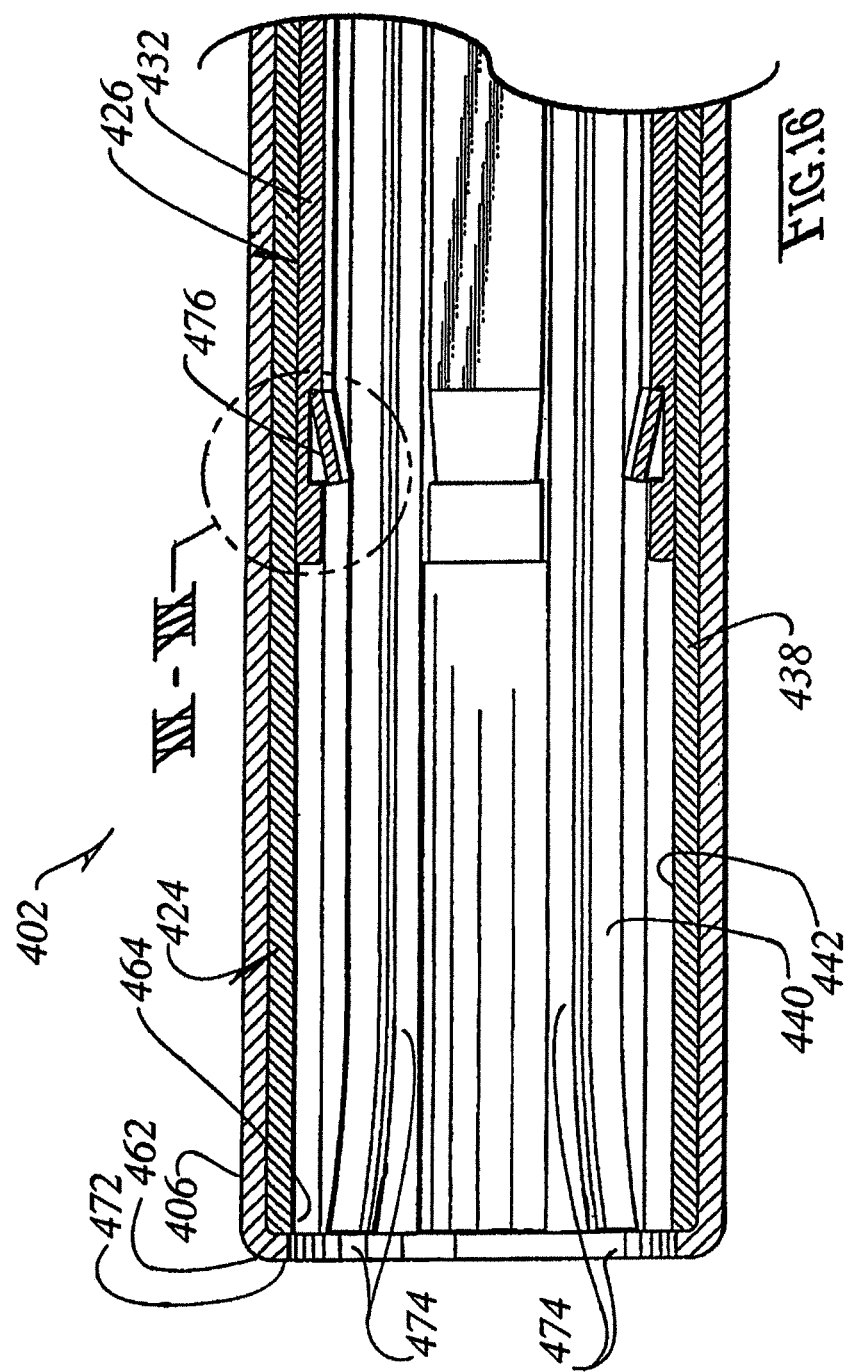

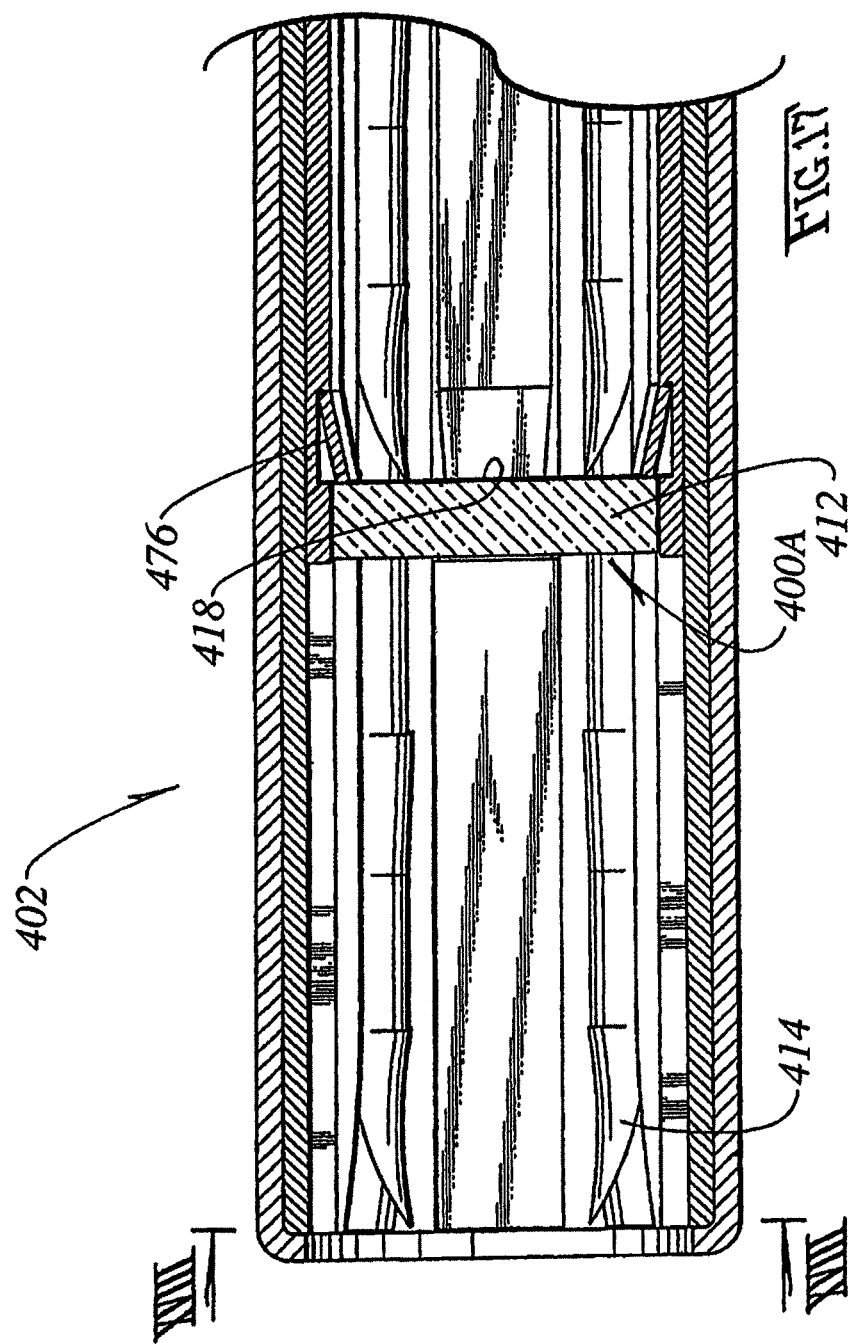

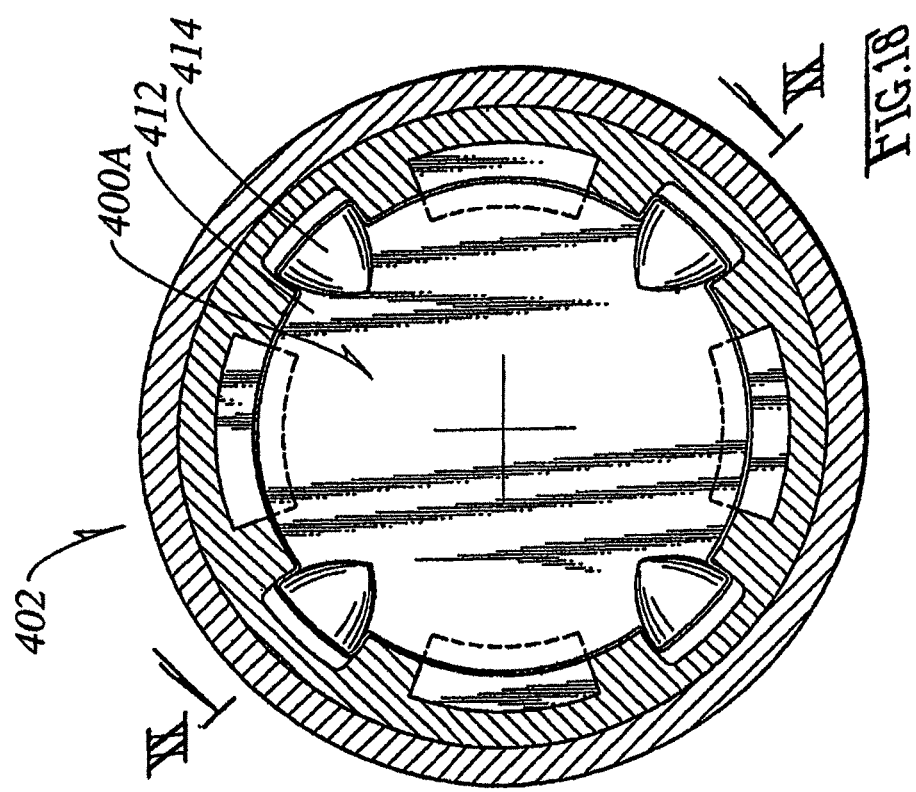

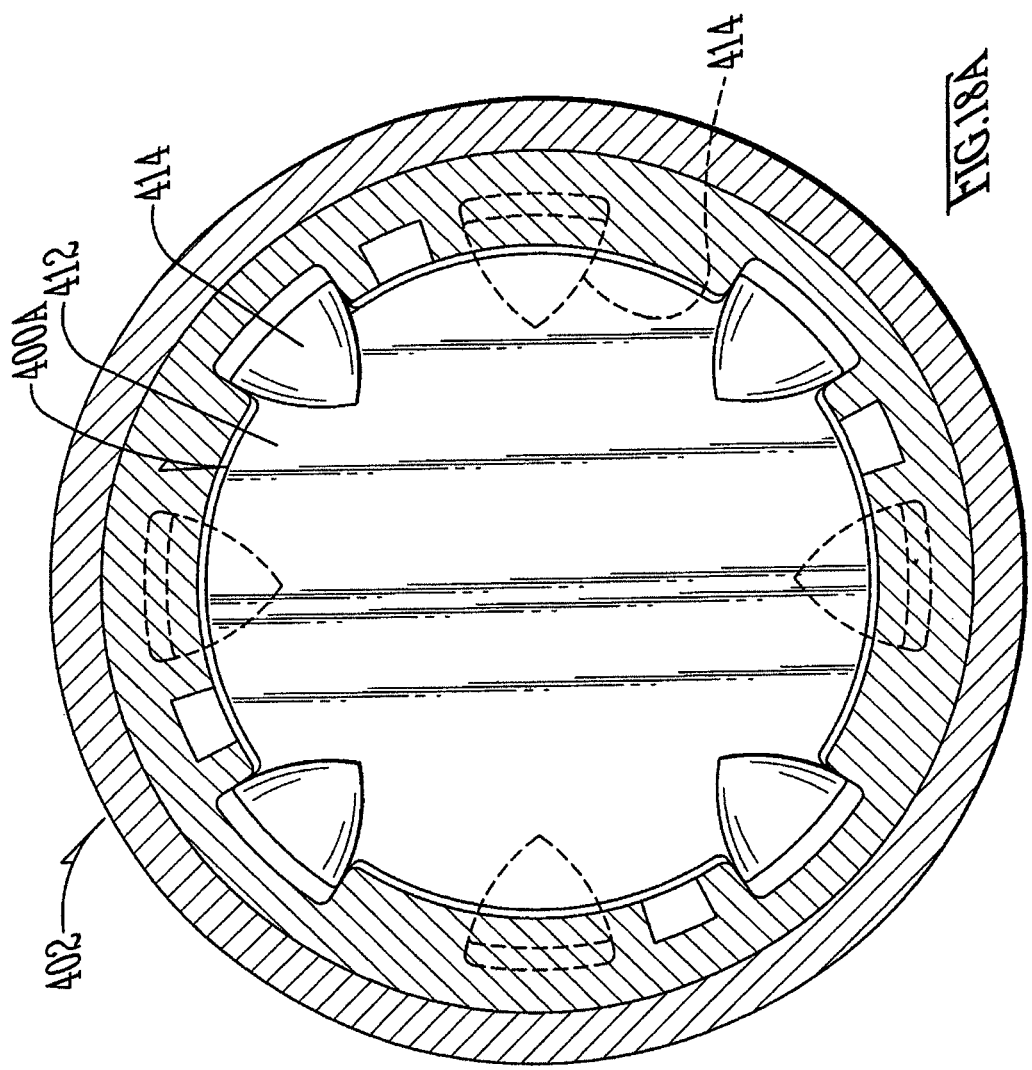

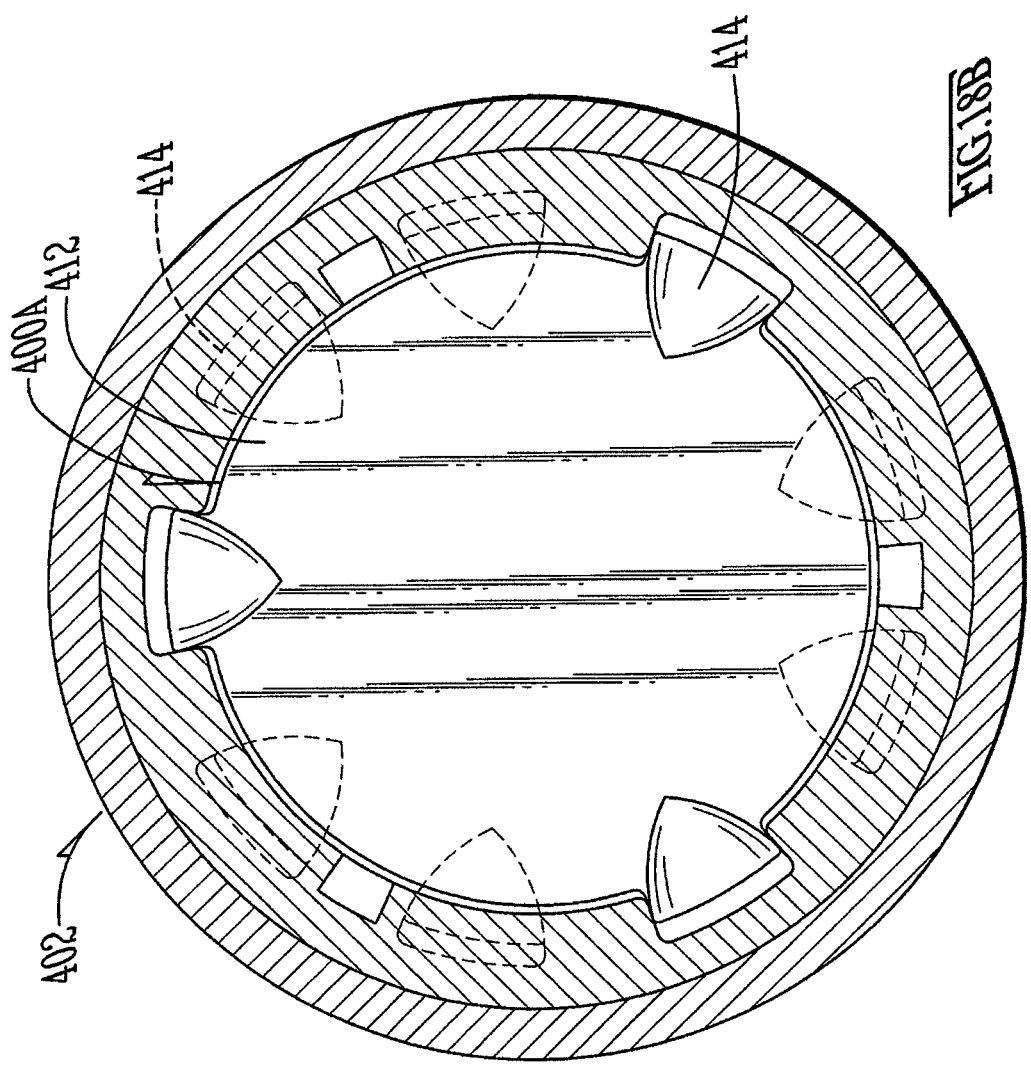

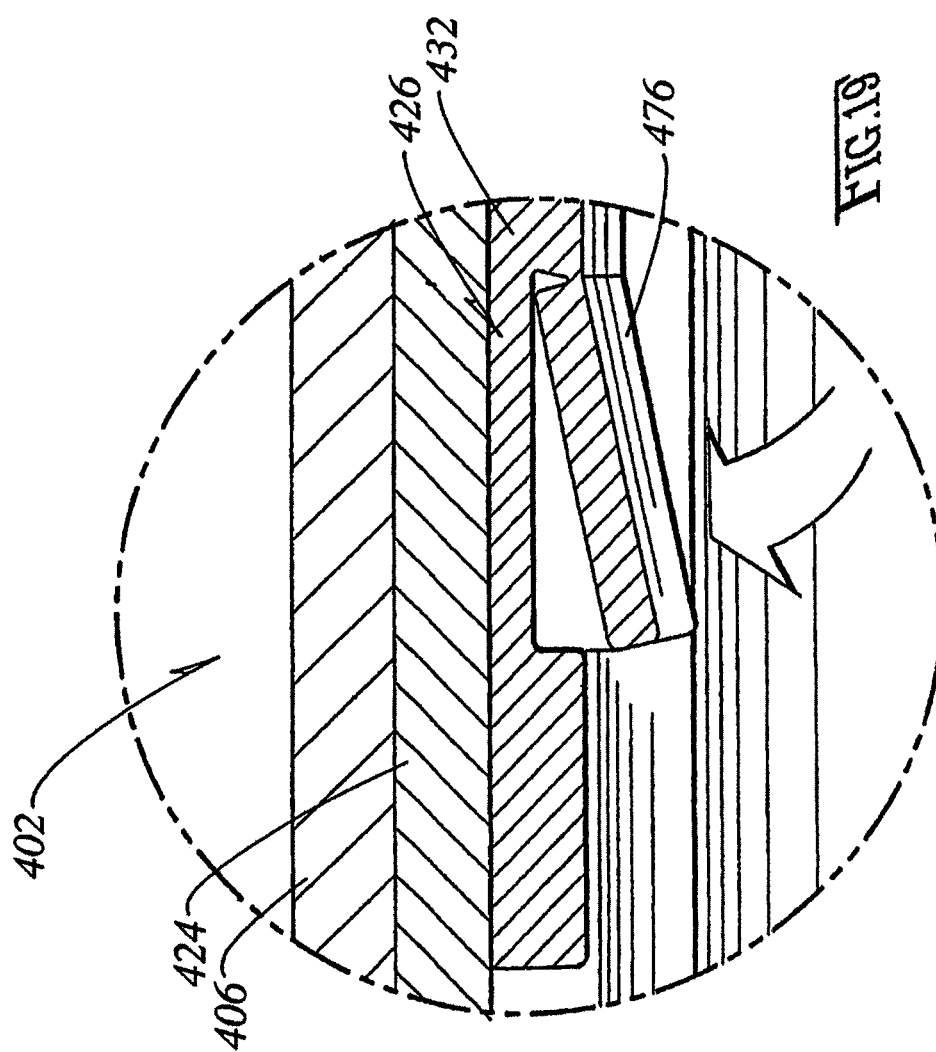

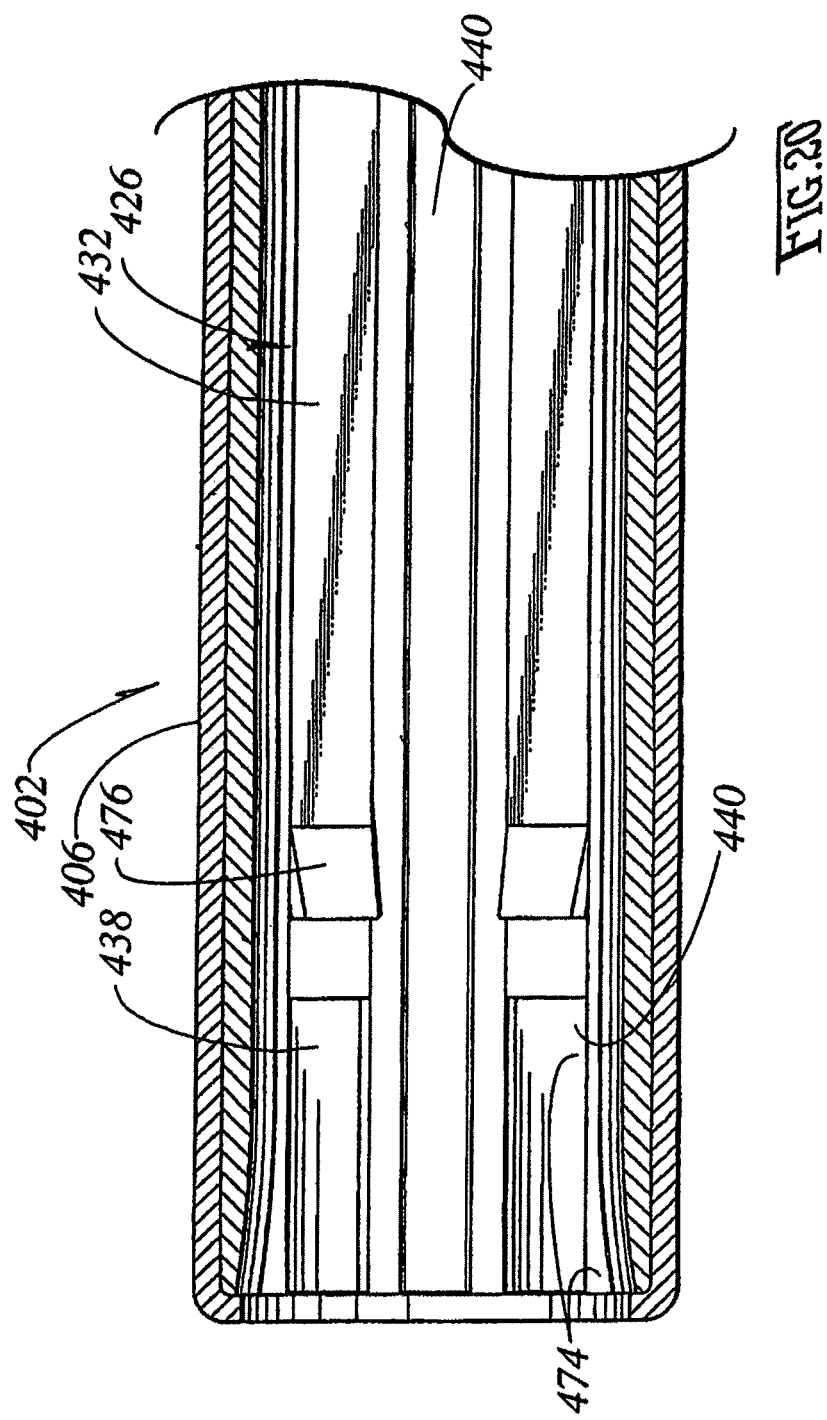

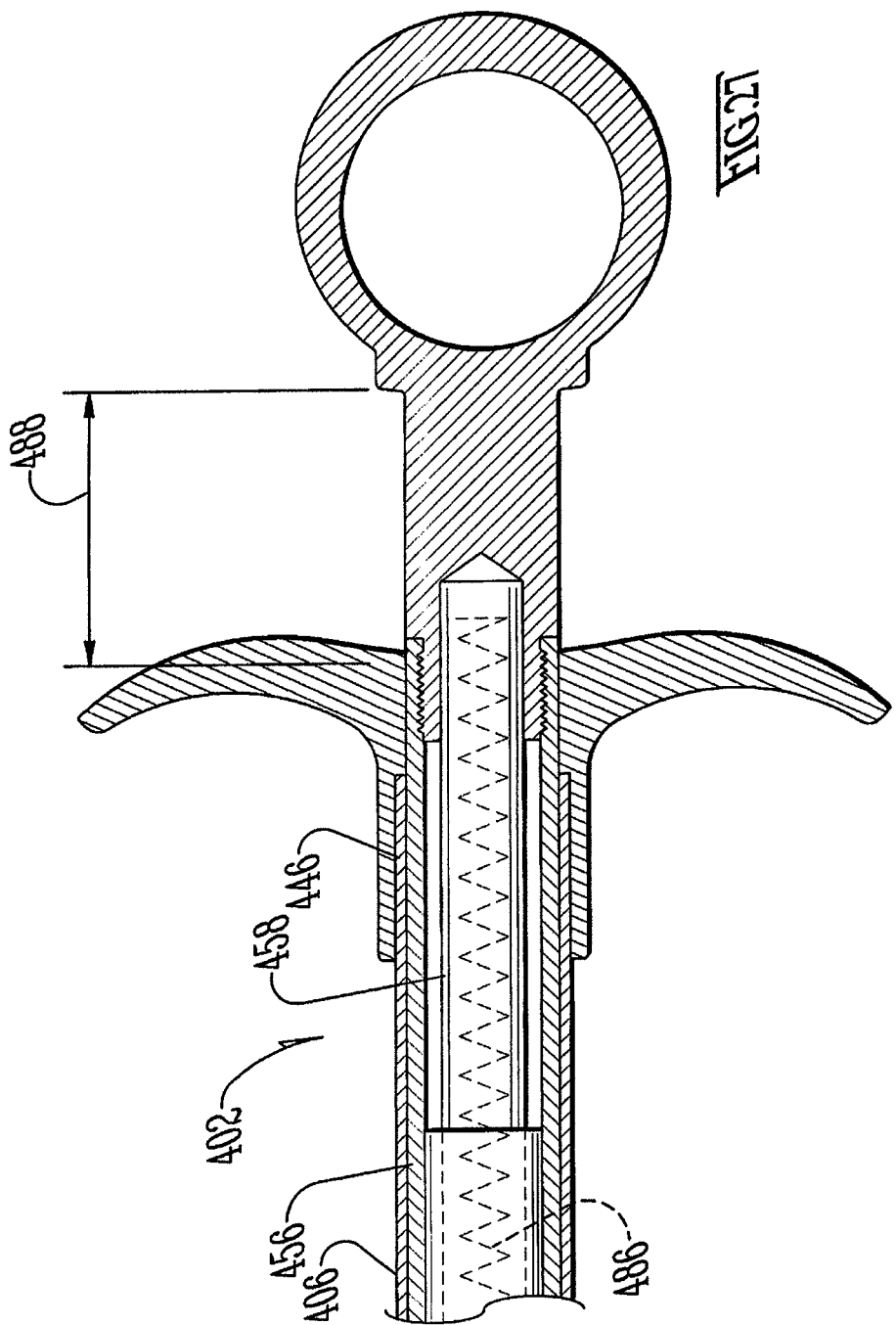

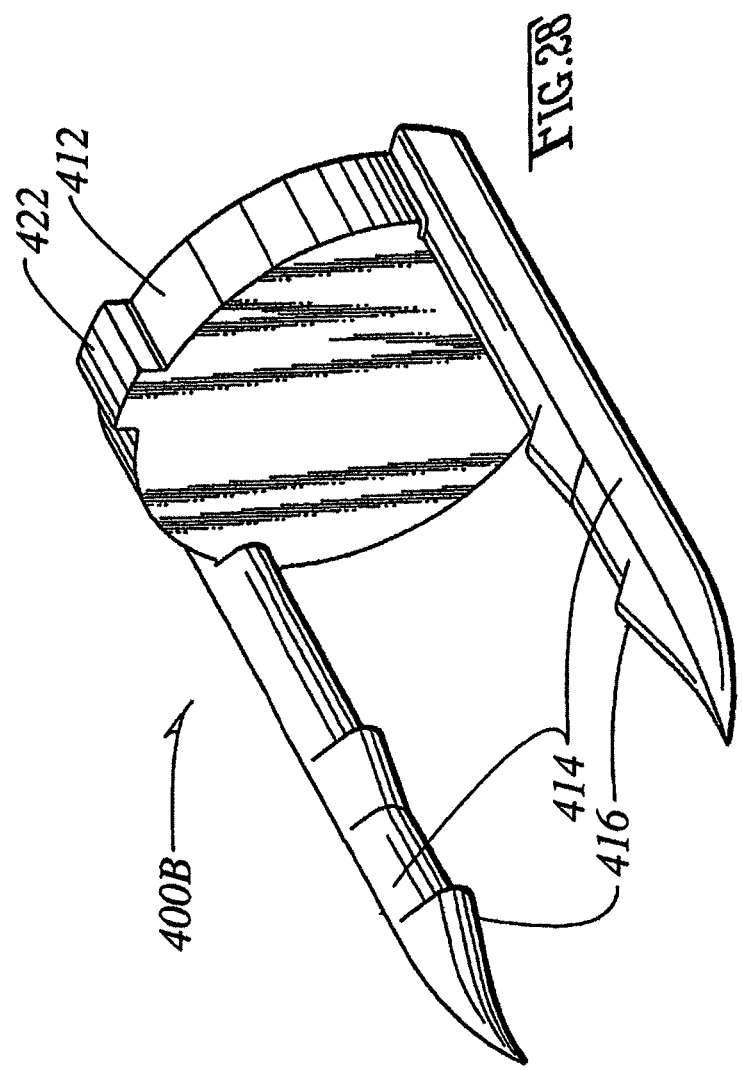

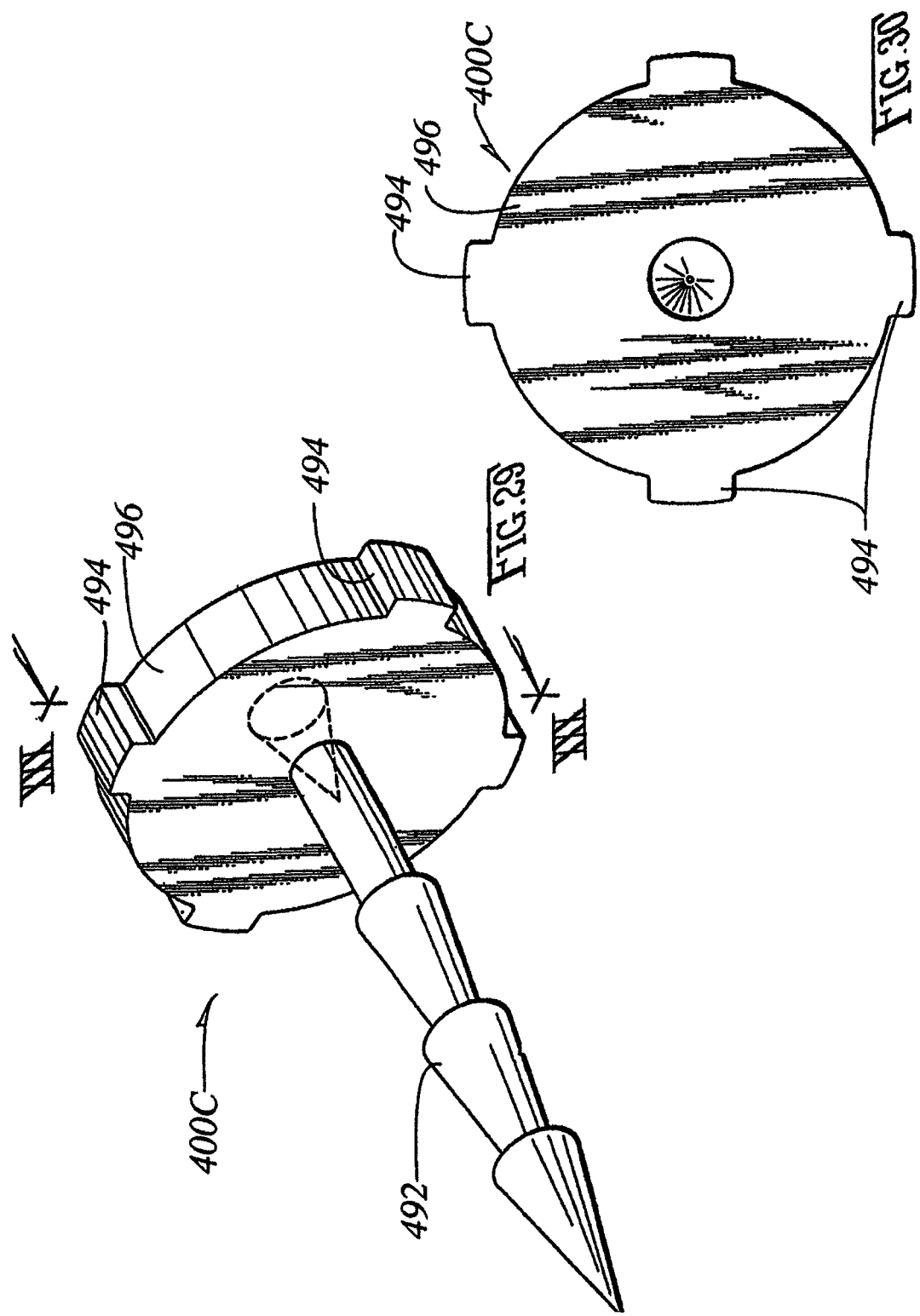

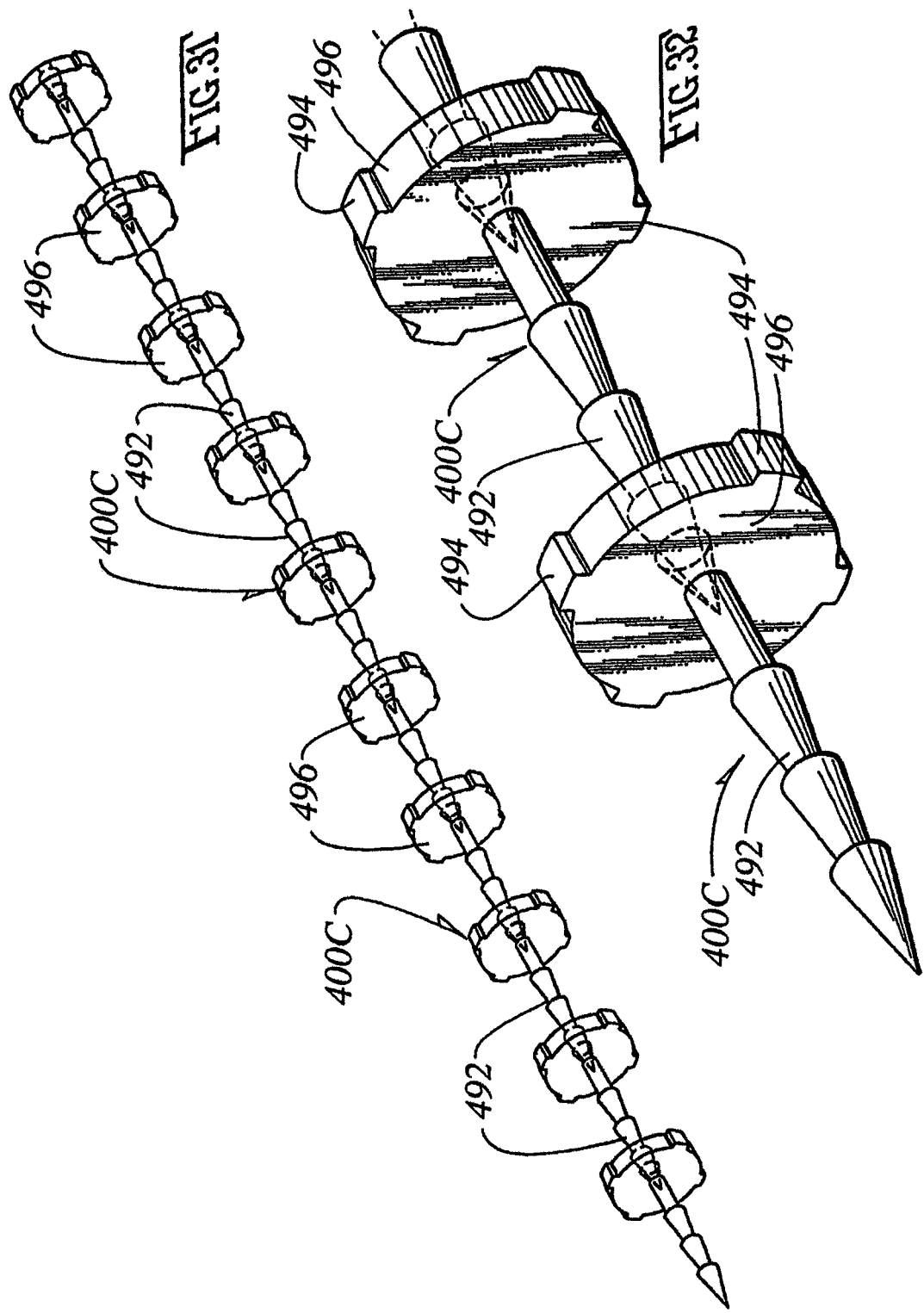

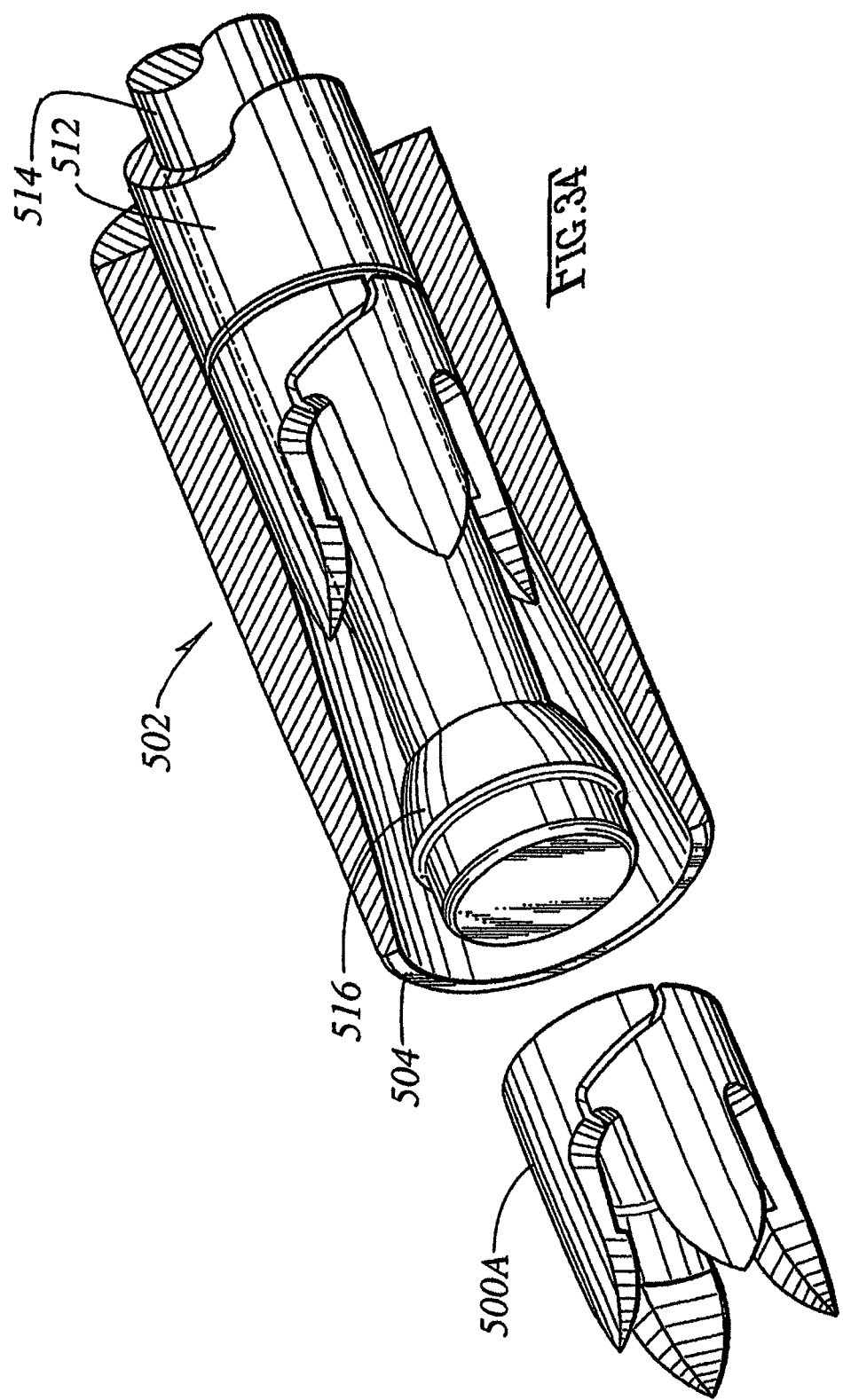

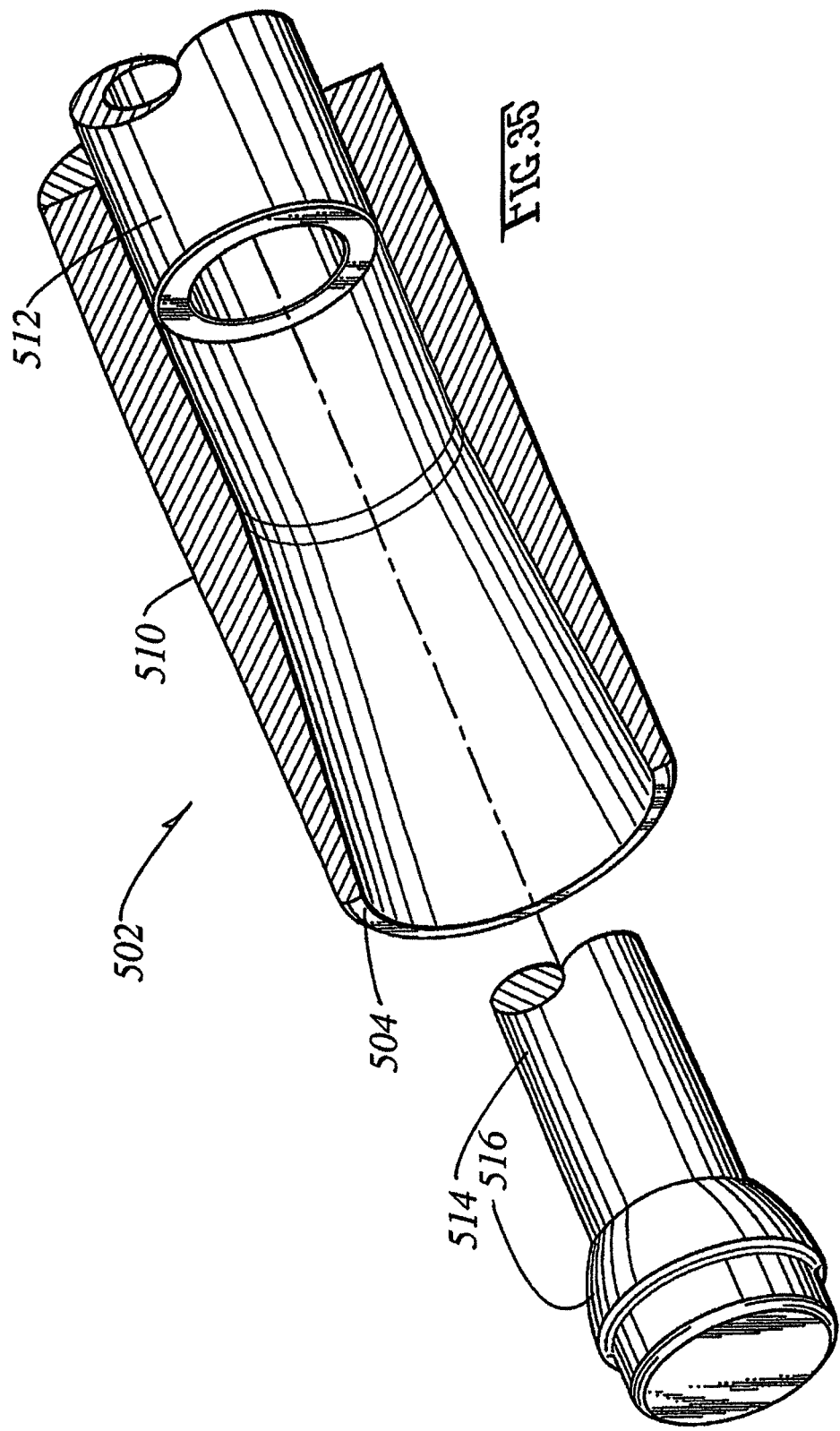

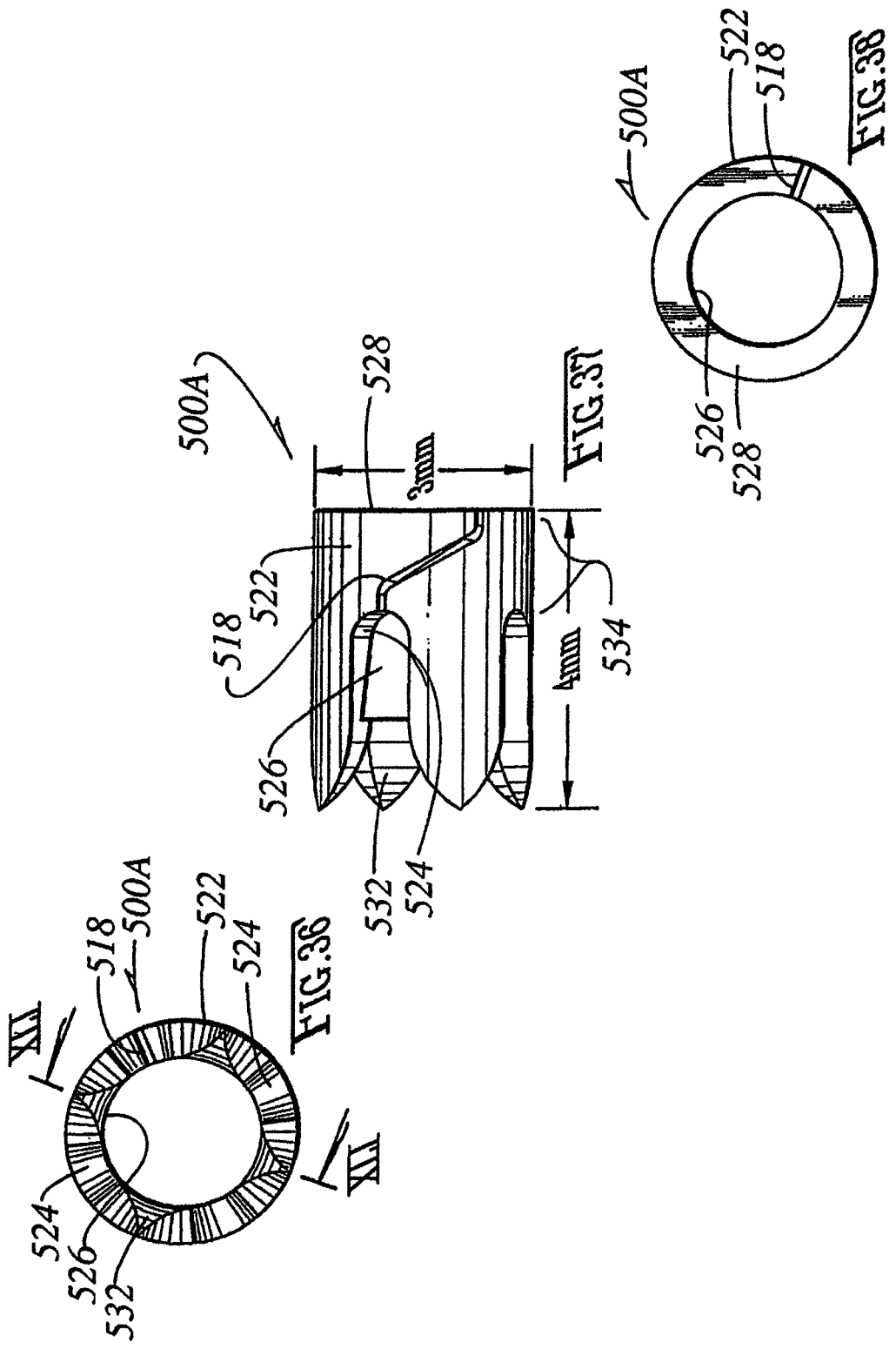

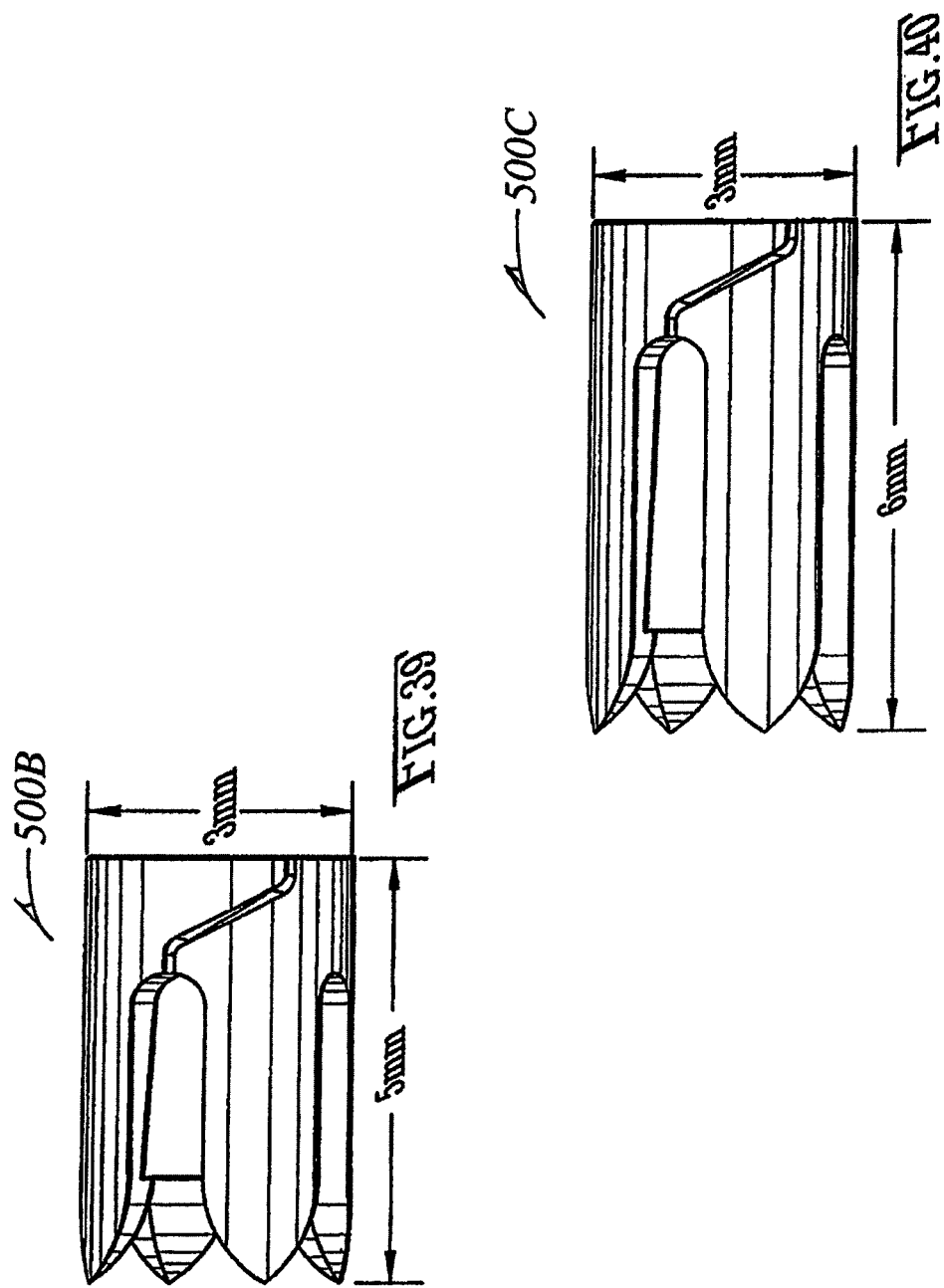

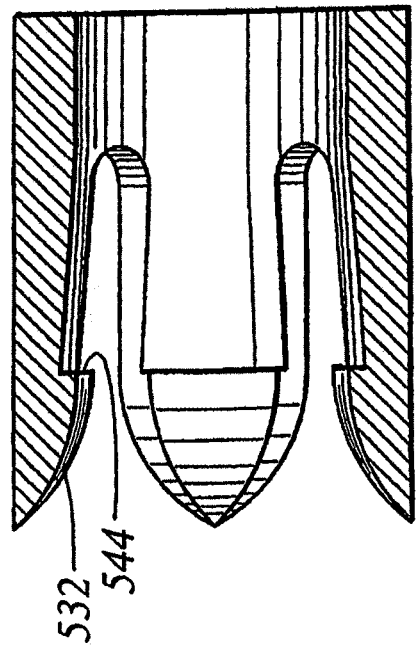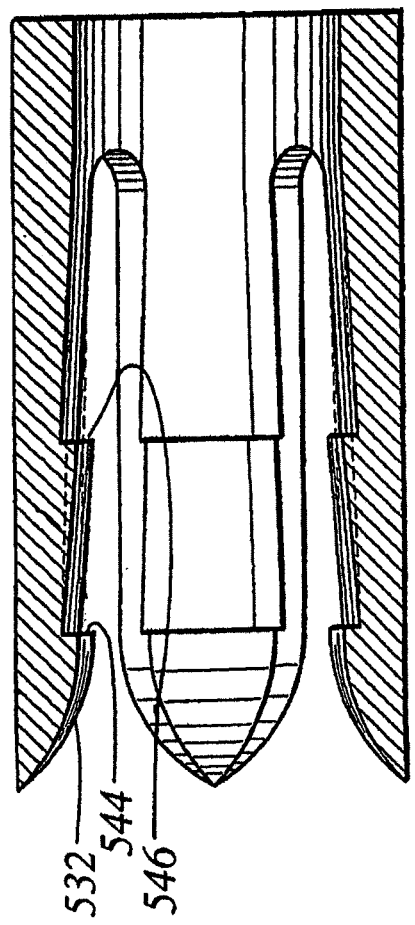

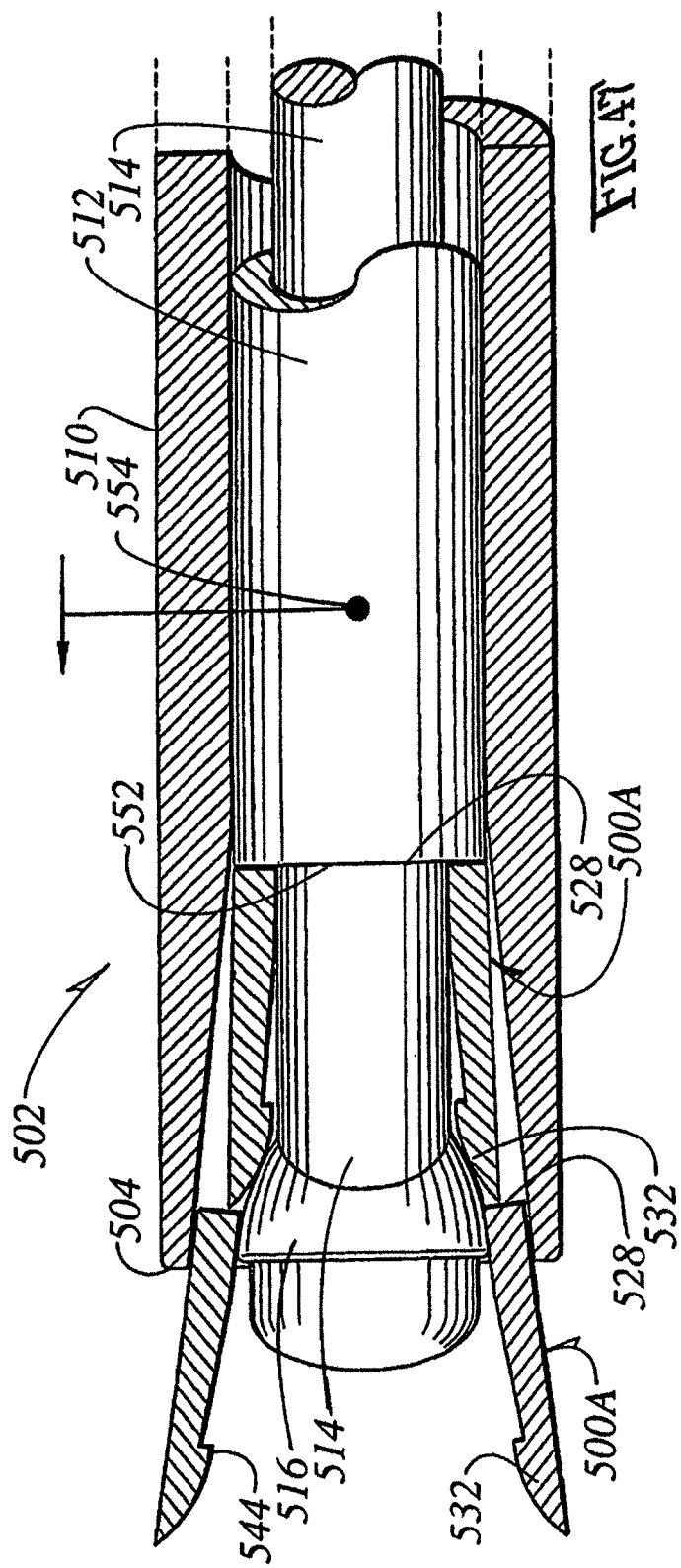

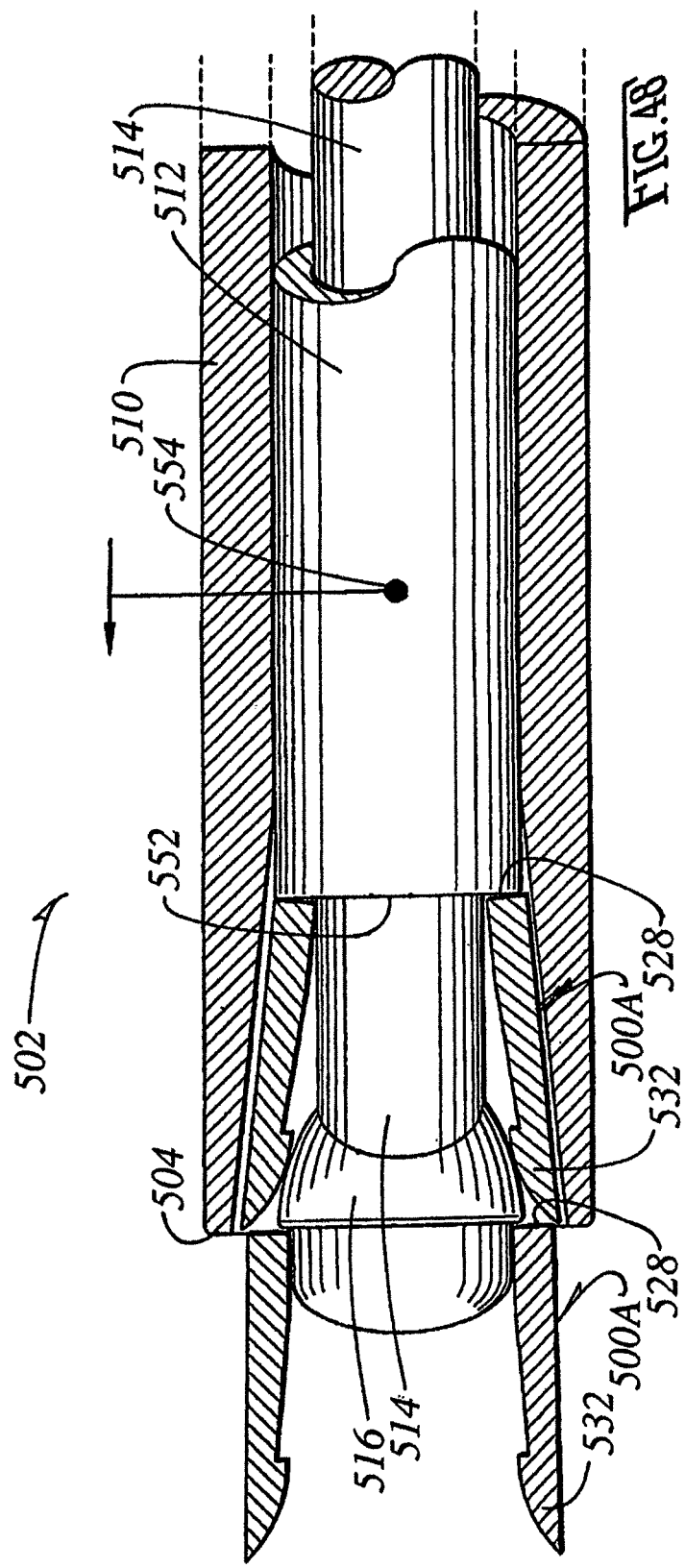

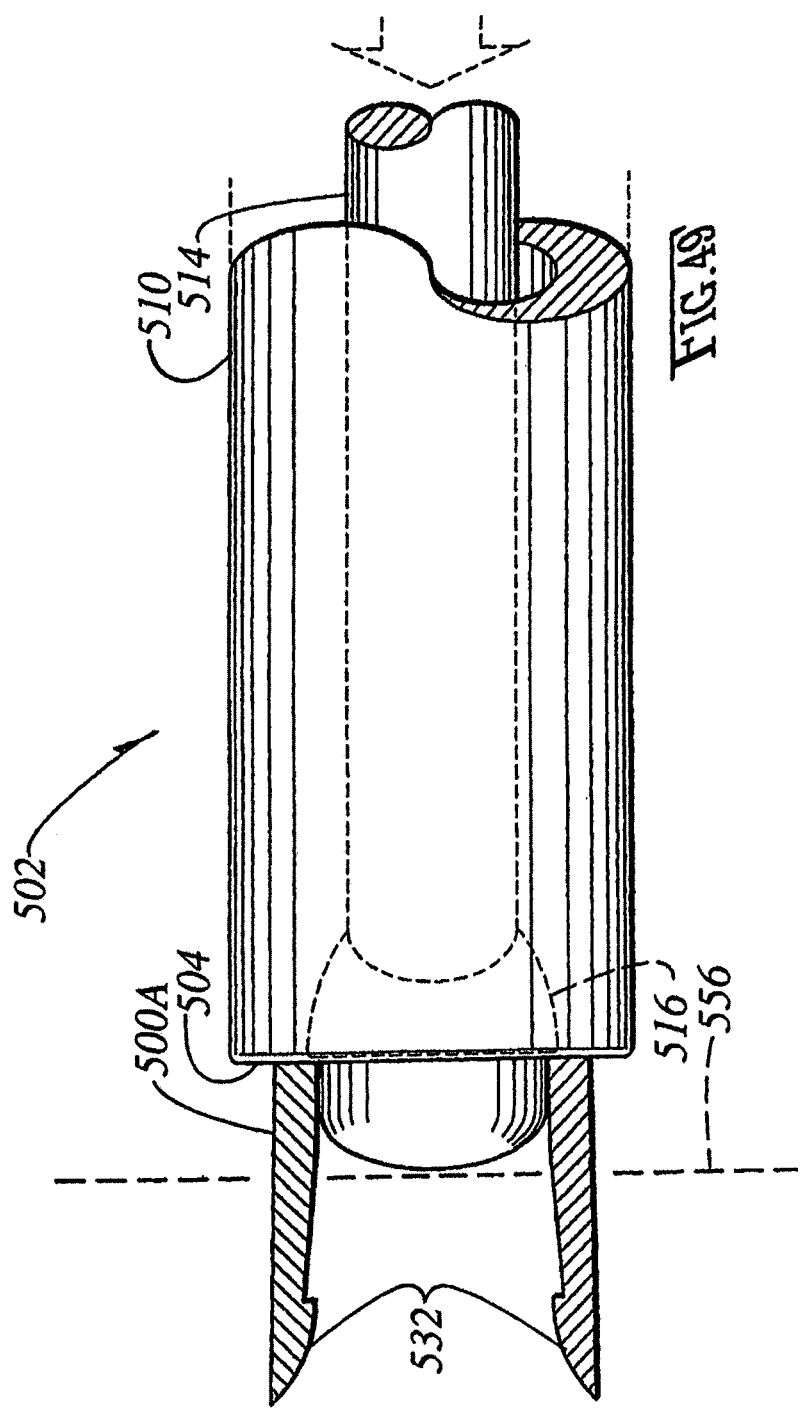

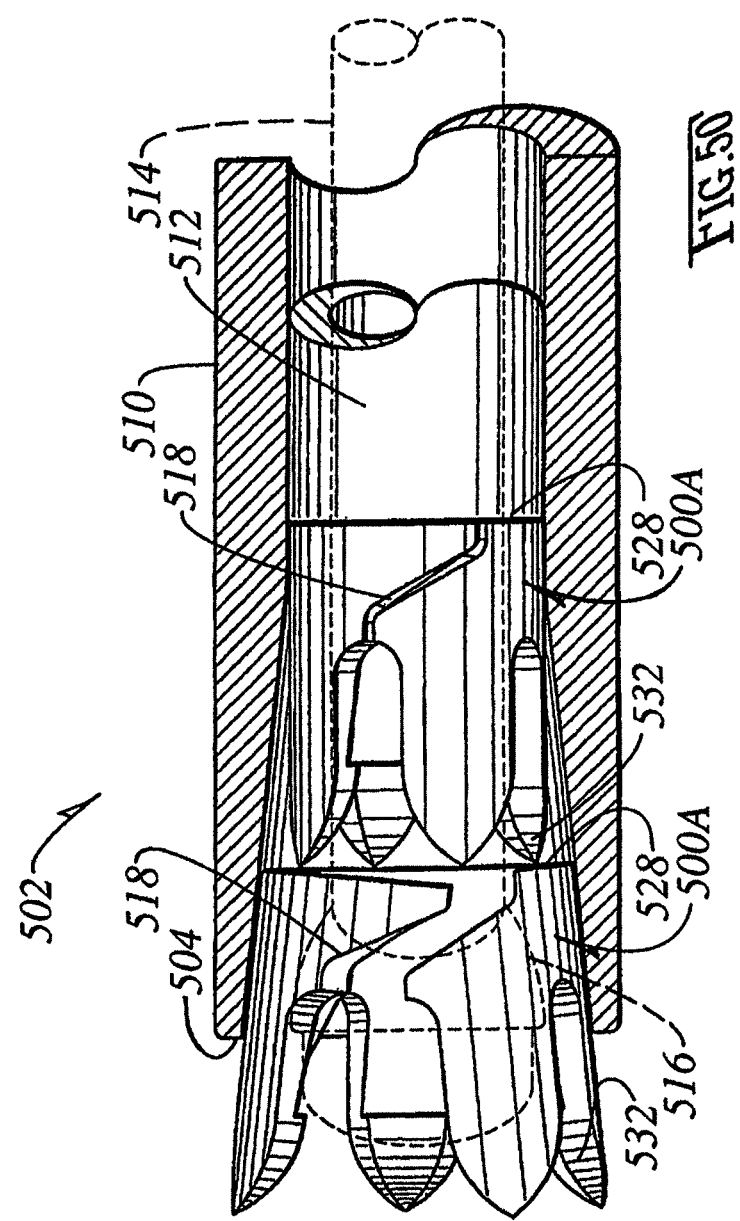

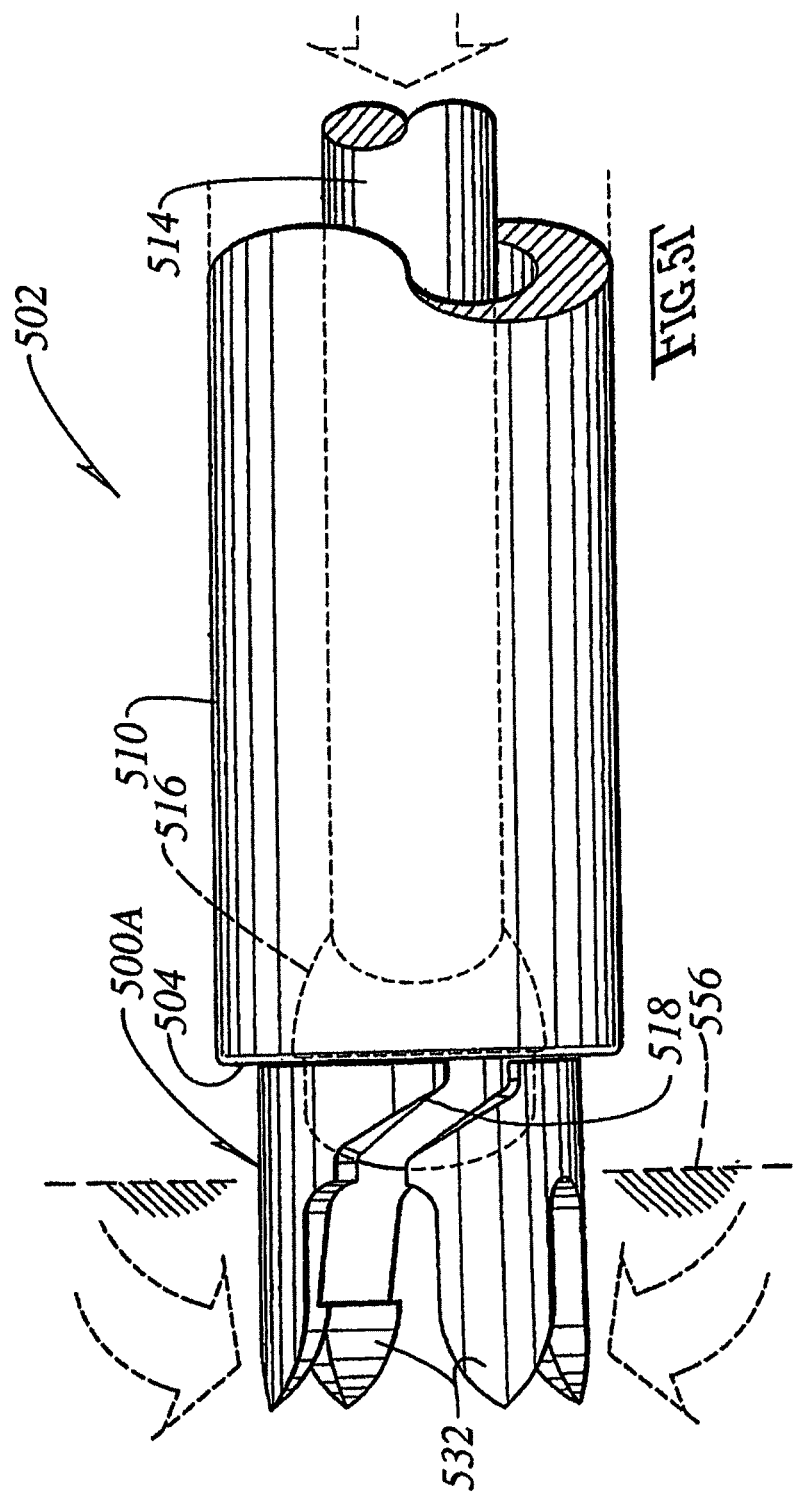

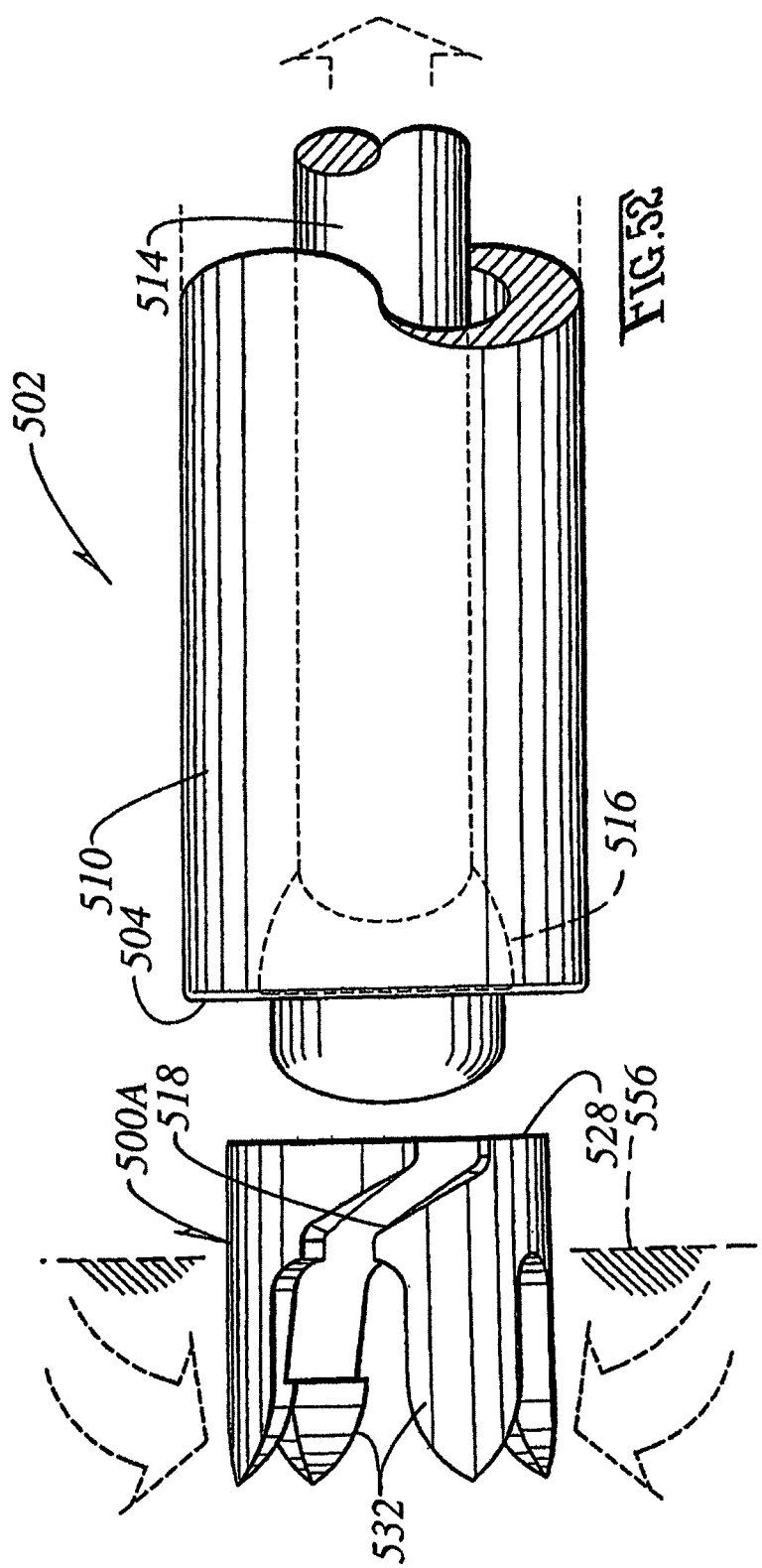

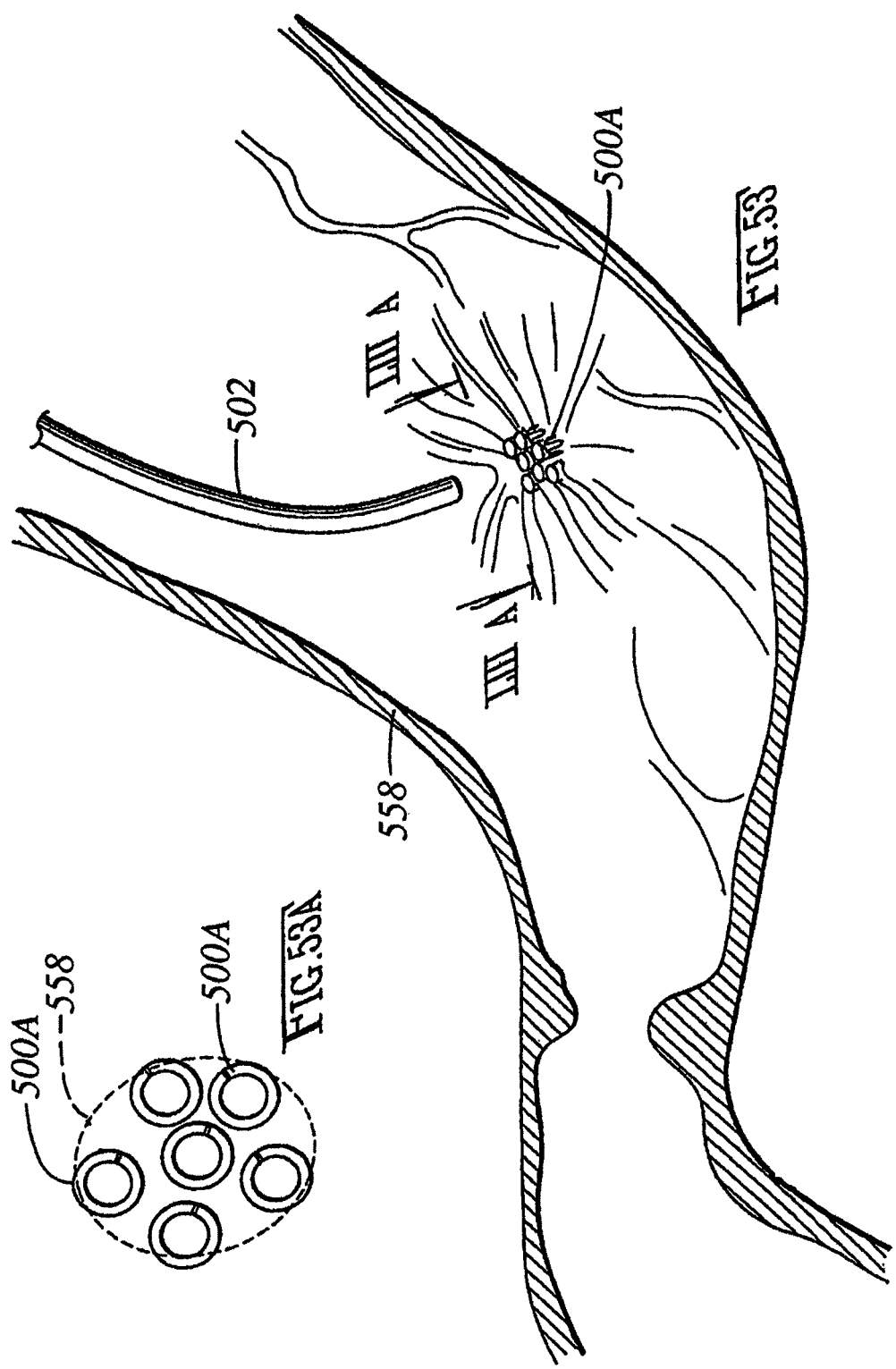

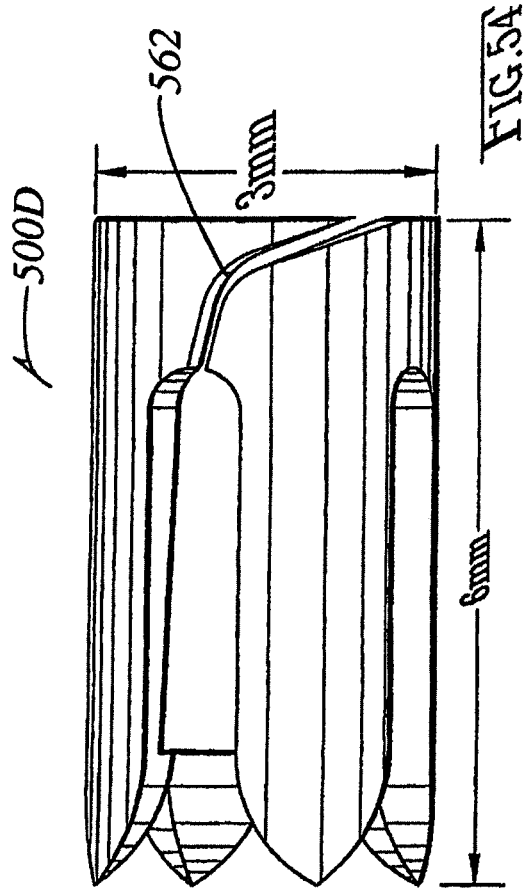
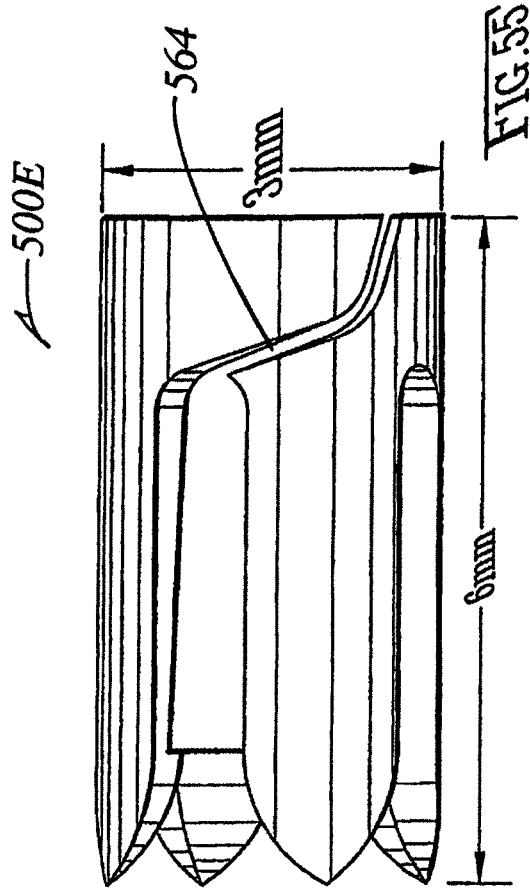

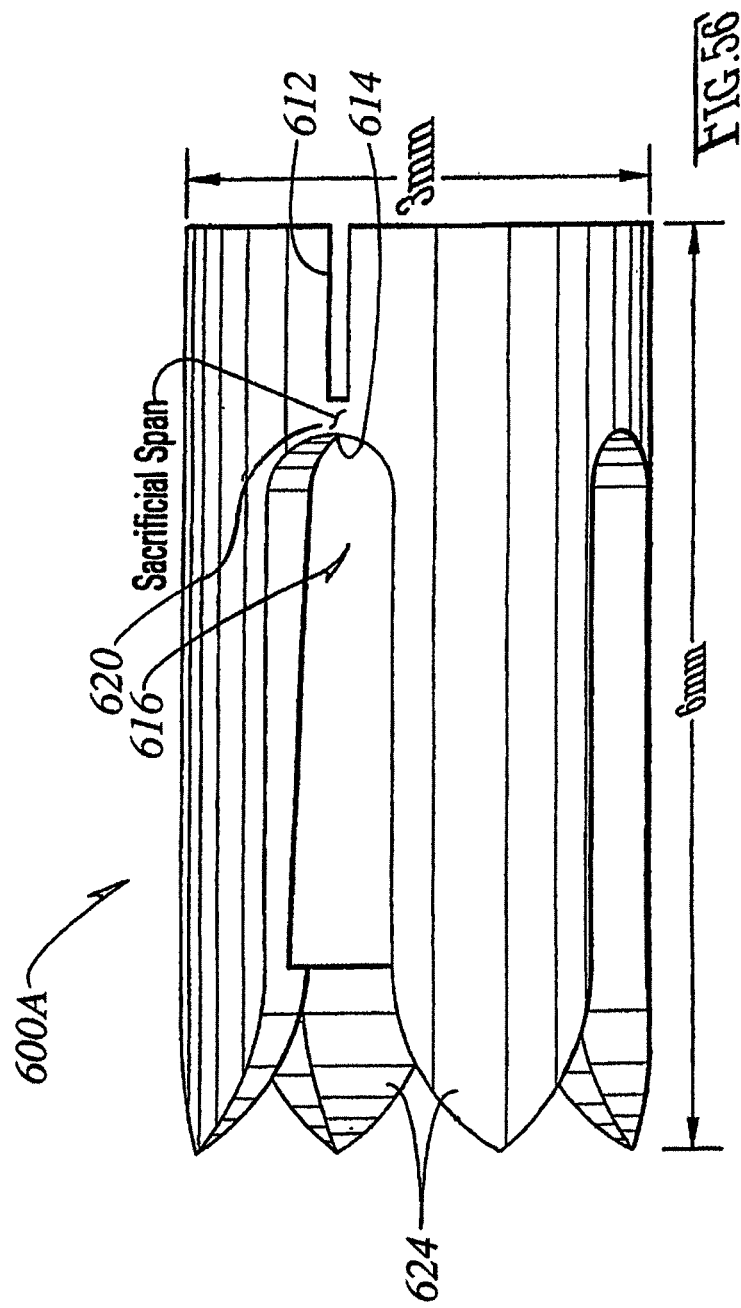

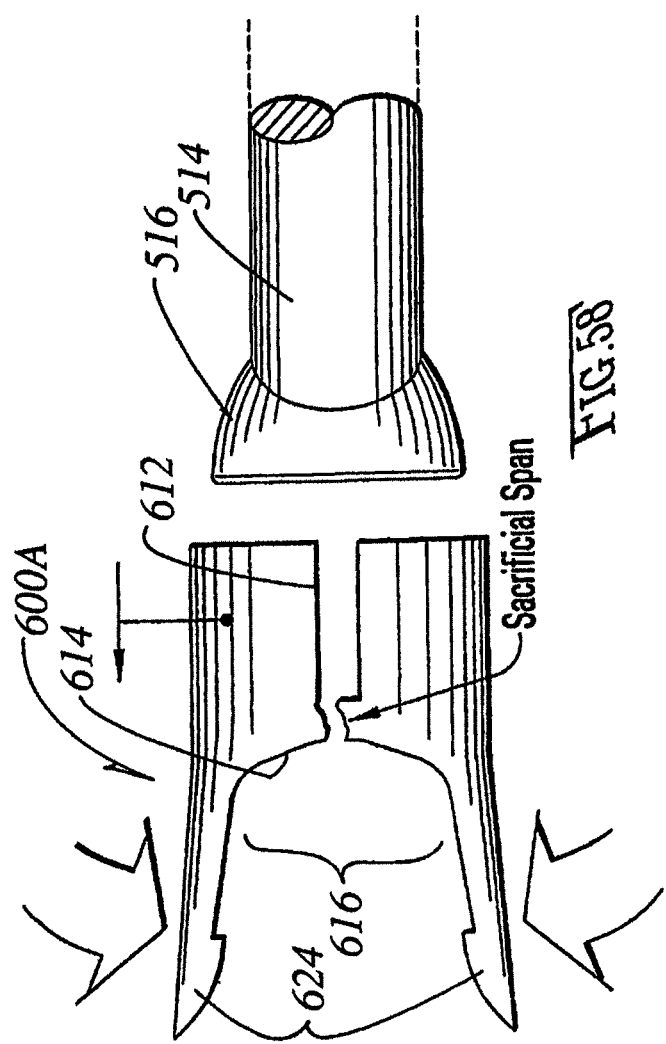

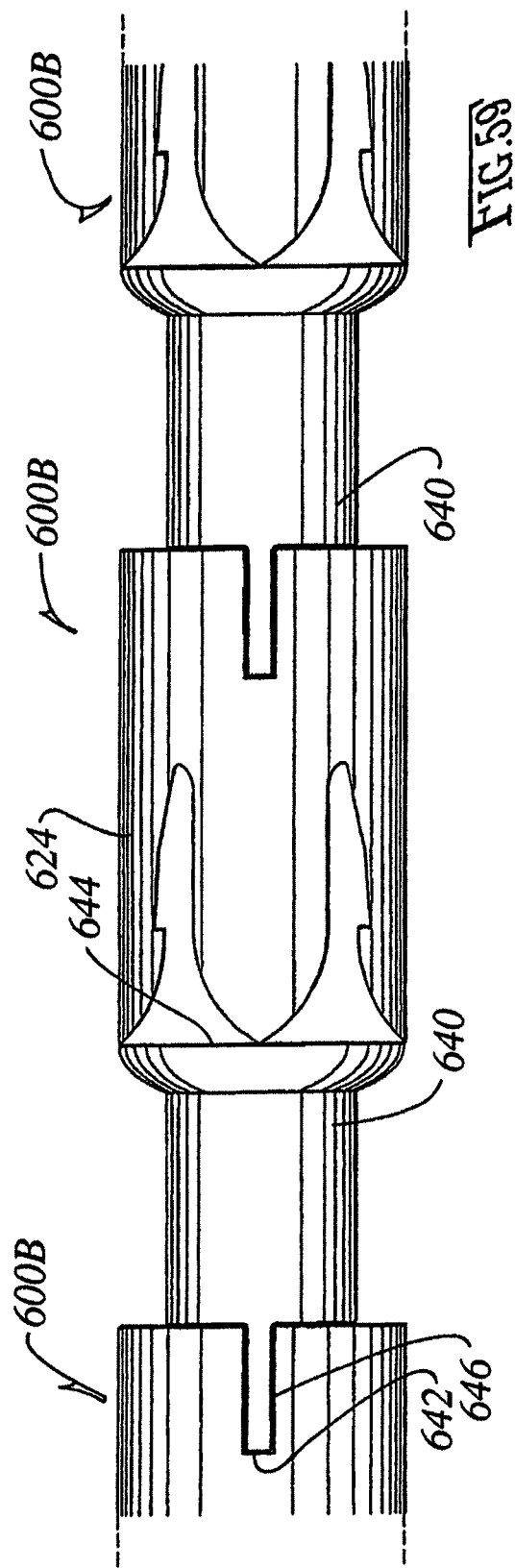

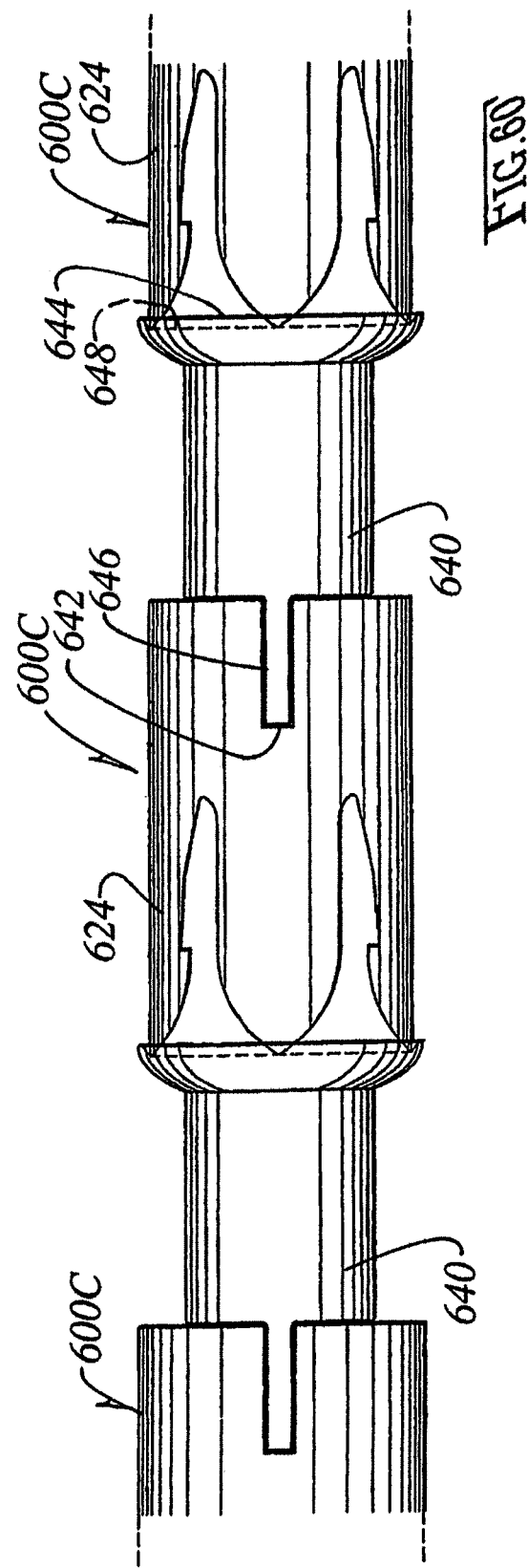

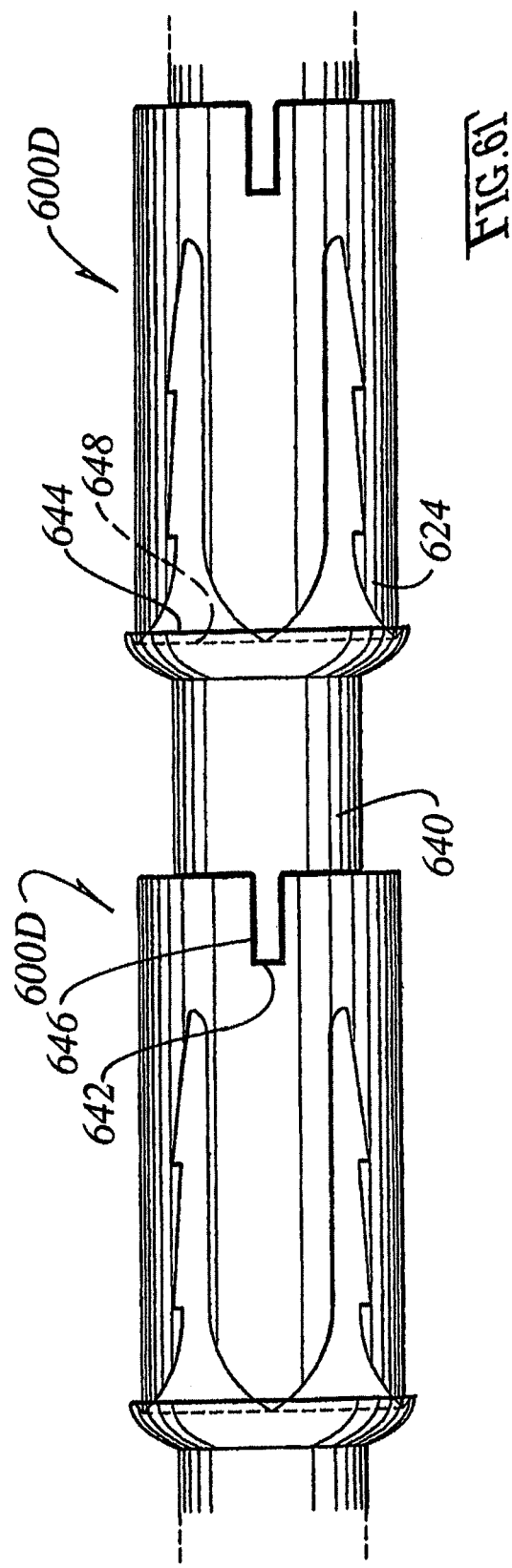

CARTRIDGE WITH MULTI-CLIP DISPENSING PROVISIONS

CROSS-REFERENCE TO RELATED APPLICATION(S)

This application is a continuation-in-part of U.S. patent application Ser. No. 14/834,186, filed Aug. 24, 2015.

The above-referenced U.S. patent application Ser. No. 14/834,186, filed Aug. 24, 2015, claims the benefit of U.S. Provisional Application No. 62/081,755, filed Nov. 19, 2014, U.S. Provisional Application No. 62/076,149, filed Nov. 6, 2014, U.S. Provisional Application No. 62/073,664, filed Oct. 31, 2014, and U.S. Provisional Application No. 62/040,908, filed Aug. 22, 2014.

The above-referenced U.S. patent application Ser. No. 14/834,186, filed Aug. 24, 2015, furthermore is a continuation-in-part of U.S. patent application Ser. No. 14/721,312, filed May 26, 2015, which claims the benefit of U.S. Provisional Application No. 62/002,691, filed May 23, 2014; and U.S. Provisional Application No. 62/016,717, filed Jun. 25, 2014;

and which is also a continuation-in-part of U.S. patent application Ser. No. 14/276,513, filed May 13, 2014, which claims the benefit of U.S. Provisional Application No. 61/961,842, filed Oct. 24, 2013; U.S. Provisional Application No. 61/957,306, accorded filing date of Jun. 29, 2013; and, U.S. Provisional Application No. 61/855,313, accorded filing date of May 14, 2013.

The foregoing patent disclosures are incorporated herein by this reference thereto.

BACKGROUND AND SUMMARY OF THE INVENTION

The invention relates to surgical instruments and, more particularly, to endoscopic surgical apparatus which accept a replaceable cartridge that has multi-clip endoscopic clip dispensing and applying provisions, and which endoscopic surgical apparatus are adapted to actuate the multi-clip endoscopic clip dispensing and applying provisions of the replaceable cartridge.

It is an object of the invention to shorten the length of time a typical procedure takes that uses these clips, by many times a fraction of what it typically takes.

This is not so much for medical efficiency, but to shorten the length of time the patient is under stress.

A number of additional features and objects will be apparent in connection with the following discussion of the preferred embodiments and examples with reference to the drawings.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the skills of a person having ordinary skill in the art to which the invention pertains. In the drawings, FIG. 1 is a perspective view of endoscopic surgical apparatus in accordance with the invention which is loaded with a replaceable cartridge with multi-clip dispensing provisions likewise in accordance with the invention;

FIG. 1B is an enlarged-scale side elevational view of the dispensing end of the endoscope of FIG. 1A, shown in dashed lines, also showing the dispensing end of the endoscopic surgical apparatus in accordance with the invention (shown in both FIGS. 1A and 1B), and which endoscopic surgical apparatus in accordance with the invention is loaded with a replaceable cartridge with multi-clip dispensing provisions likewise in accordance with the invention;

FIG. 2 is a perspective view of a first embodiment of a surgery clip in accordance with the invention;

FIG. 3 is a side elevation view of the surgery clip of FIG. 2;

FIG. 3A is a side elevation view comparable to FIG. 3 except showing each of the three resilient prongs of the clip that are in view in partial section, and each made of a different representative resilient (or else, elastic or springy material, ie., material which can recoil or spring back after bending or other deformation), wherein the top prong is depicted with section shading indicative of plastic or rubbery material, the middle prong of steel, and the lower prong of aluminum, however any one clip is likely to be made as a monolithic piece of one material or another, and not a composite;

FIG. 5 is an end elevation view of the surgery clip taken in the direction of arrows V-V in FIG. 3;

FIG. 6 is a perspective view of the cartridge in accordance with invention and a load of ten (10) clips in accordance with the invention as lined up in a single file (or, column);

FIG. 7 is a perspective view of the cartridge in accordance with the invention as disassembled apart into two pieces;

FIG. 12 is a section view taken along line XII-XII of FIG. 9;

FIG. 13 is a section view taken along line XIII-XIII of FIG. 8;

FIG. 14 is an end elevation view taken in the direction of arrows XIV-XIV of FIG. 8;

FIG. 15 is an end elevation view taken in the direction of arrows XV-XV of FIG. 8;

FIG. 16 is a sectional view of taken along an axial plane of symmetry through FIG. 9;

FIG. 17 is a sectional view comparable to FIG. 16 except also including the loading of a column of clips of in accordance with the invention;

FIG. 18 is a section view taken along line XVIII-XVIII in FIG. 17;

FIG. 18A is a section view comparable to FIG. 18 except showing the plurality of axially-elongated groove and/or axially elongated arms arranged and angularly-distributed in multiples of two (2's);

FIG. 18B is a section view comparable to FIGS. 18 and 18A except showing the plurality of axially-elongated groove and/or axially elongated arms arranged and angularly-distributed in multiples of three (3's);

FIG. 19 is an enlarged scale section view of detail XIX-XIX in FIG. 16;

FIG. 20 is a section view taken along line XX-XX in FIG. 18, wherein FIG. 20 serves to rotate the section views subsequently hereof to a new orientation as shown previously, wherein all section views shown previously had a channel for an arm of the slide ejector shown in the 12 o'clock position, henceforth, a groove for a prong of a clip will take the 12 o'clock position, the orientation between previous section views and subsequent section views being rotated about 45° counter-clockwise (or 135° and/or 225° or else 315° given the symmetry hereof), and wherein this FIG. 20 shows better the flaring apart of the dove-tailed grooves for the dove-tailed prongs of the clips at the dispensing end of the magazine cannister;

FIG. 21 shows a start position (SP) for the stroke of the slide;

FIG. 22 shows about a 66% extension position of the full stroke;

FIG. 23 shows about a 75% extension position of the full stroke; and

FIG. 24 shows about 100% extension of the full stroke;

FIG. 27 is section view comparable to FIG. 26 except of the manually-actuated plunger of the elongated endoscopic apparatus of FIG. 1;

FIG. 28 is a perspective view of a second embodiment of a surgery clip in accordance with the invention;

FIG. 29 is a perspective view of a third embodiment of a surgery clip in accordance with the invention;

FIG. 30 is a rear elevational view taken in the direction of arrows XXX-XXX in FIG. 29 clip;

FIG. 31 is a reduced scale perspective view of a column or load-formation of ten such clips as shown in FIG. 29;

FIG. 32 is an enlarged scale detail view (in perspective) of two such clips in the column in FIG. 31;

FIG. 34 is a perspective view partly in section comparable to FIG. 33 except showing better the three rings comprising (A) the catheter, which is the outer ring, (B) the middle ring occupied by both (i) a column or load of clips and (ii) the a plunger/driver conduit which only has a forward stroke; as well as (C) the central strand which is which terminates in a bulbed terminal end that is stationary relative to the end of the catheter;

FIG. 35 is an enlarged scale perspective view, partly exploded, to show that the central strand threads into the hollow lumen of the plunger/driver conduit;

FIG. 36 is front elevational view of any of the clips of FIGS. 33 and 34;

FIG. 37 is a side elevational view of FIG. 36;

FIG. 38 is a rear elevational view of FIG. 37;

FIG. 39 is a side elevational view comparable to FIG. 37 except showing that another preferred size for the clip is 5 mm long by 3 mm outside diameter (ie., the full inside diameter of the catheter's hollow passageway therefor);

FIG. 40 is a side elevational view comparable to FIGS. 37 and 39 except showing that a further preferred size for the clip is 6 mm long by 3 mm outside diameter (ie., the full inside diameter of the catheter's hollow passageway therefor);

FIG. 41 is an enlarged scale sectional view taken along line XLI-XLI in FIG. 36;

FIG. 42 is a sectional view comparable FIG. 41 except showing that a longer clip may afford opportunity for two barbs on each prong;

FIGS. 43 through 48 comprise a series of comparable sectional views to show the manner in which this version of a dispensing mechanism dispenses this version of a clip; wherein:

FIG. 43 is a reduced scale partial sectional view of FIG. 34, except in elevation (and with the clip floating out in front of the catheter removed from view);

FIG. 44 is a partial sectional view comparable to FIG. 43 except showing the plunger/driver conduit driving forward, pushing the trailing clip to ultimately push the lead clip such that the prongs of the lead clip are widened apart by the bulbed head of the central strand;

FIG. 45 is a comparable view to FIG. 44 except showing further forward travel of the plunger/driver conduit, forcing the lead clip to progress further over the bulbed head of the central strand, which the barbs of the prongs have passed across;

FIG. 46 is a partial sectional view comparable to FIG. 45 except showing the clips in solid line, and showing widening apart of the longitudinal through-slot in the constant-wall thickness, slotted-collar portion of the clip;

FIG. 47 is a view comparable to FIG. 45 except showing the butt end of the lead clip about to pass the widest circumference of the bulbed head of the central strand;

FIG. 48 shows that the lead clip has at last cleared past the widest circumference of the bulbed head of the central strand;

FIG. 49 is an elevational view, partly in section, comparable to FIG. 48 except showing that the prongs have not only pierced into tissue (such as for example and without limitation, the stomach wall), but also clenched back into themselves from their formerly flared out formation;

FIG. 50 is a partial sectional view comparable to FIG. 46 except starting a series of views, namely, along with FIGS. 51 and 52, to show the dispensing of the last clip in the former column of clips which have since been dispensed;

FIG. 51 is a side elevation view comparable to FIG. 49, again showing the snapping back into toward themselves of the four prongs of the last clip, and thereby pinching the pierced tissue in a fast grasp;

FIG. 52 is a view comparable to FIG. 51 except showing withdrawal of the catheter;

FIG. 53 shows the preferred result of the clips and dispenser in accordance with the invention;

FIG. 53A is an enlarged scale plan view of the detail LIII(A)-LIII(A) in FIG. 53;

FIG. 54 is a side elevational views comparable to any of FIGS. 37, 39 and 40 (and most particularly closest to FIG. 40), except showing that the (diagonally tracking) through slot shown in FIGS. 37, 39 and 40 can alternatively be given a non-linear course;

FIG. 55 is a side elevational views comparable to FIG. 54 except showing an alternate curvature to the slot;

FIGS. 56 through 58 comprise a series of side elevational views showing an alternative embodiment of the a clip in accordance with the invention; wherein:—

FIG. 56 shows the clip at rest with the sacrificial span intact;

FIG. 57 shows how the sacrificial span has the effect of forcing the prongs to flare out wider as the prongs transit past the bulbed terminal end of the stationary (relative to the catheter) central strand;

FIG. 58 shows how the sacrificial span is eventually severed by the bulbed terminal end of the stationary central strand, thereby releasing the prongs to snap shut;

FIGS. 59 through 61 show a plurality of spacers in accordance with invention in alternation with a plurality of clips in the single file line-up loaded in the cartridge; wherein:—

FIG. 59 is a side elevational view showing a single file series of a clip, then a spacer, then a clip again (and so on);

FIG. 60 is a side elevational view comparable to FIG. 59 except showing a shorter clip; and FIG. 61 is a side elevational view comparable to FIGS. 59 and 60 except showing a longer clip than both.

DETAILED DESCRIPTION OF THE PREFERRED EMBODIMENTS

Figure 1A:
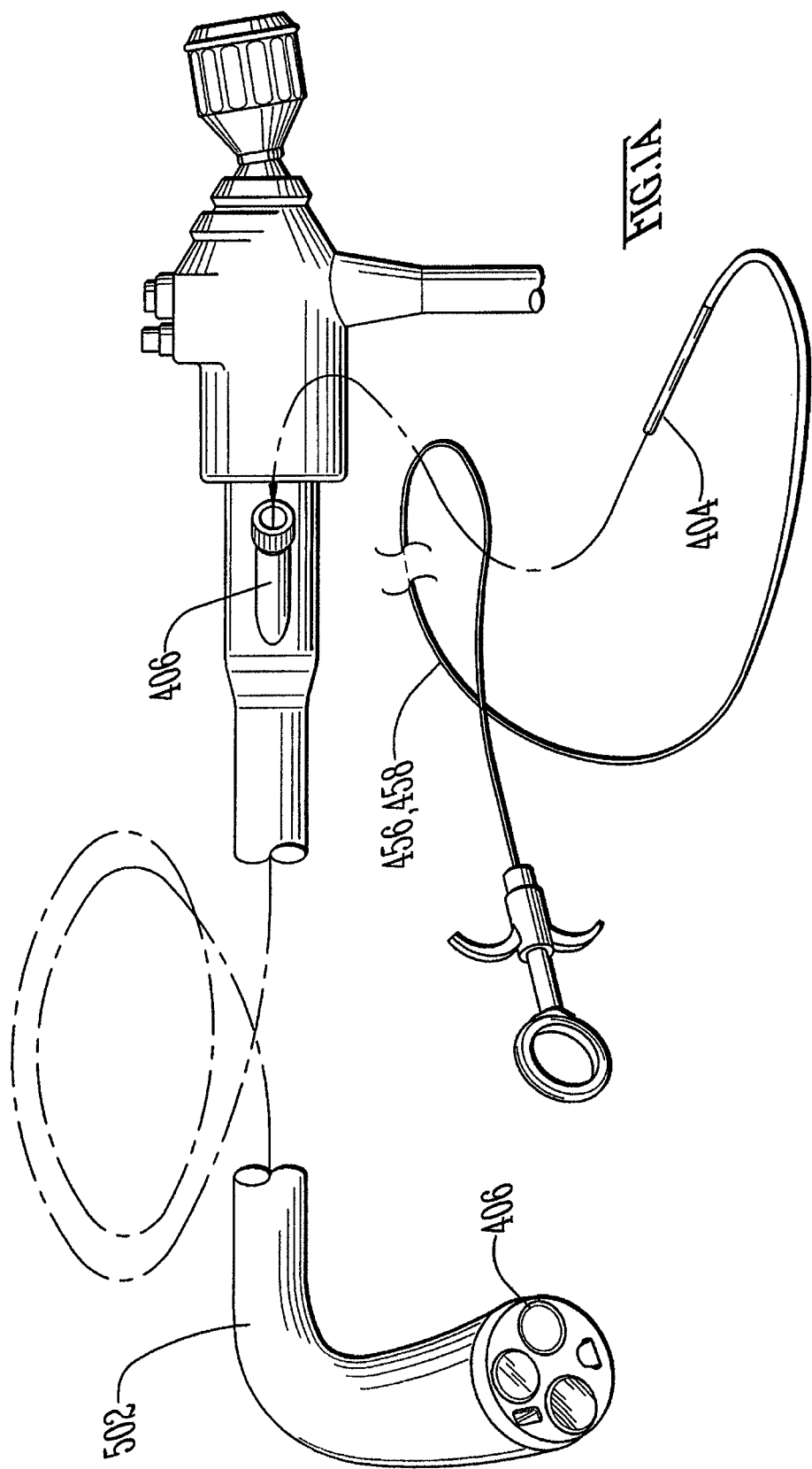
FIG. 1A is a reduced-scale perspective view of an endoscope which removably receives endoscopic surgical apparatus in accordance with the invention as shown in FIG. 1.

FIG. 1 is a perspective view of an endoscopic surgical apparatus 402 in accordance with the invention which is loaded with a replaceable cartridge 404 likewise in accordance with the invention, wherein the loaded cartridge 404 is barely in view and on a miniature scale in the open end of the slender and flexible tubular sidewall 406 of the catheter 402, but a carrying case 408 is shown independently to the side and containing ten such cartridges 404, it being an aspect of the invention that both the endoscopic apparatus 402 and the cartridge(s) 404 have provisions for multi-clip endoscopic-clip dispensing and applying, preferably one clip 400A at a time (see FIG. 2).

FIG. 2 is a perspective view of a first embodiment of a surgery clip 400A in accordance with the invention, wherein this clip 400A comprises a coin-like base 412, and from which base 412 there are four barbed prongs 414 extending straight forward (wherein the direction 'forward' is non-limiting and is merely relative a given point-of-view). The prongs 414 have barbs 416.

FIG. 3 is a side elevation view of the surgery clip 400A of FIG. 2, wherein the base 412 comprises a rear surface 418 serving as the butt end therefor.

Figure 4A:
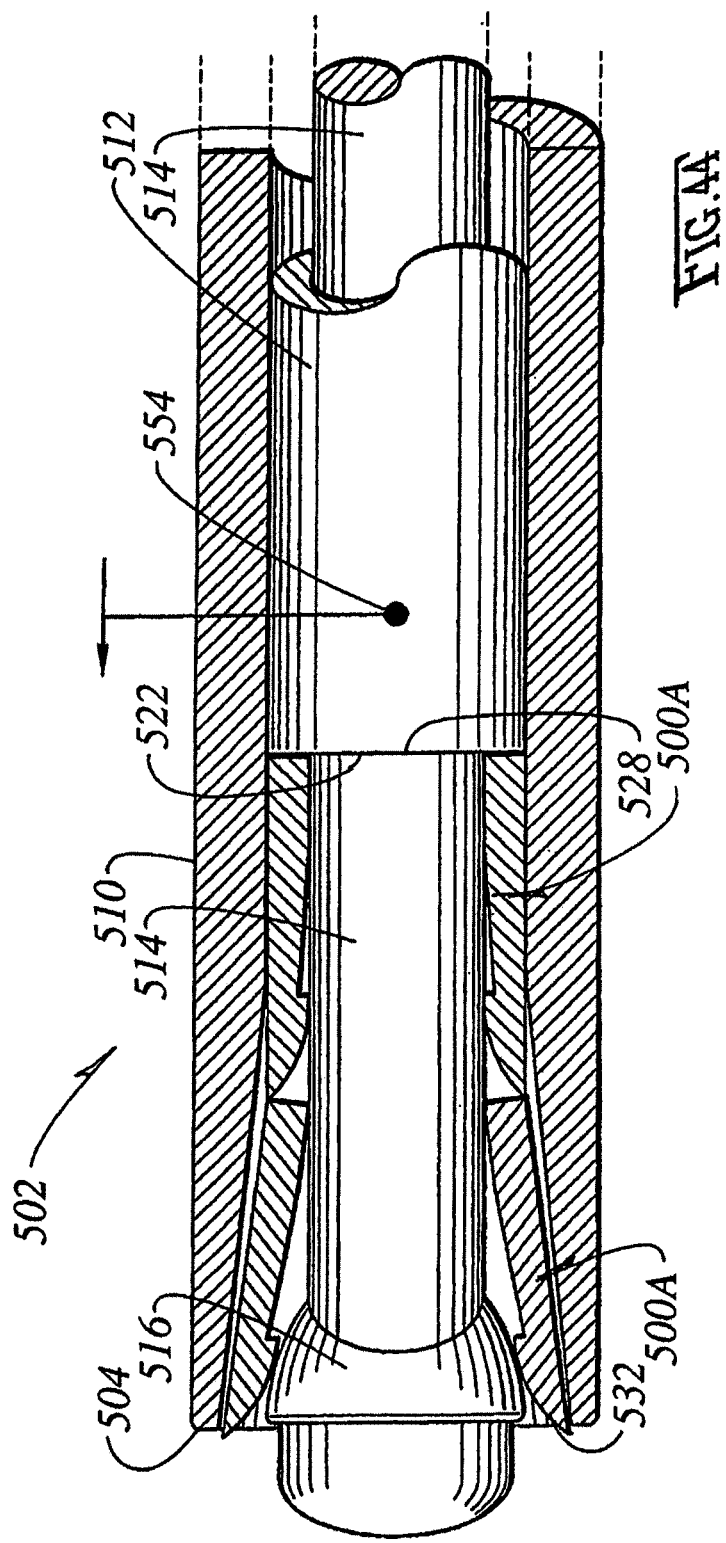
FIG. 4 is an end elevation view of the surgery clip taken in the direction of arrows IV-IV in FIG. 3.

FIG. 4 is an end elevation view of the surgery clip 400A taken in the direction of arrows IV-IV in FIG. 3 (eg., the 'forward' end), and which shows that each of the four prongs 414 present a dove-tailed tongue profile.

FIG. 5 is an end elevation view of the surgery clip 400A taken in the direction of arrows V-V in FIG. 3 (eg., the 'rear' or 'butt' end 418), and which shows four tabs 422, each of which tabs 422 serves as the base portion for one of the respective four prongs 414, wherein the tabs 422 continue the dove-tailed tongue profile of the prongs 414.

FIG. 6 is a perspective view of the cartridge 404 in accordance with invention and a load of ten clips 400A in accordance with the invention as lined up in a single file (or, column), wherein the column of clips 400A are shown to the side of the cartridge 404 to indicate how such a column of clips 400A load should be chambered into the cartridge 404.

Each clip is typically going to be 6 to 9 mm long and typically about 3 mm outside diameter. A cartridge of ten clips is going to be seventy-five to one hundred mm long (eg., ~three to four inches), while still about 3 or 4 mm outside diameter. The axial length of the lumen of endoscopic apparatus 402 is going to be nine-hundred to twelve hundred mm long (eg., ~three to four feet). Hence the characteristic axial length of the slender cartridge is many fractions less than an eighth (⅛th) of the characteristic axial length of the lumen, while the characteristic axial length of the slender flexible driver conduit 456 and slender flexible plunger 458 are going to be greater than the characteristic axial length of the lumen.

FIG. 7 is a perspective view of the cartridge 404 in accordance with the invention as disassembled apart into two pieces, namely (i) a stationary magazine cannister 424 and (ii) a reciprocating ejector slide 426; wherein ejector slide 426 has a ring base 428 from which four slender and elongate arms 432 project forwardly therefrom, each arm 432 having a detent 434 formed on the outer sidewall 436 thereof proximate but spaced away from the ring base 428, the magazine cannister 424 having two sets of four-per-set axially-elongated channels or grooves 438,440 formed on the inside wall thereof, one of which sets of channels 438 are spaced and sized for the arms 432 of the slide ejector 426 to reciprocate therein, whereby the magazine cannister 424 has each channel 438 for the arms 432 of the slide ejector 426 further formed with a relatively deepened section 444 indicated in dashed lines in FIG. 7, wherein the deepened sections 444 not only allow the reciprocation therein of the detents 434 on the arms 432 of the slide ejector 426 but also enable the magazine cannister 424 to be withdrawn completely out of the slender and flexible tubular sidewall (see 454 of FIG. 8) of the endoscope 402 out of the very back end thereof (which back end 446 is shown in FIG. 27).

Figure 8:
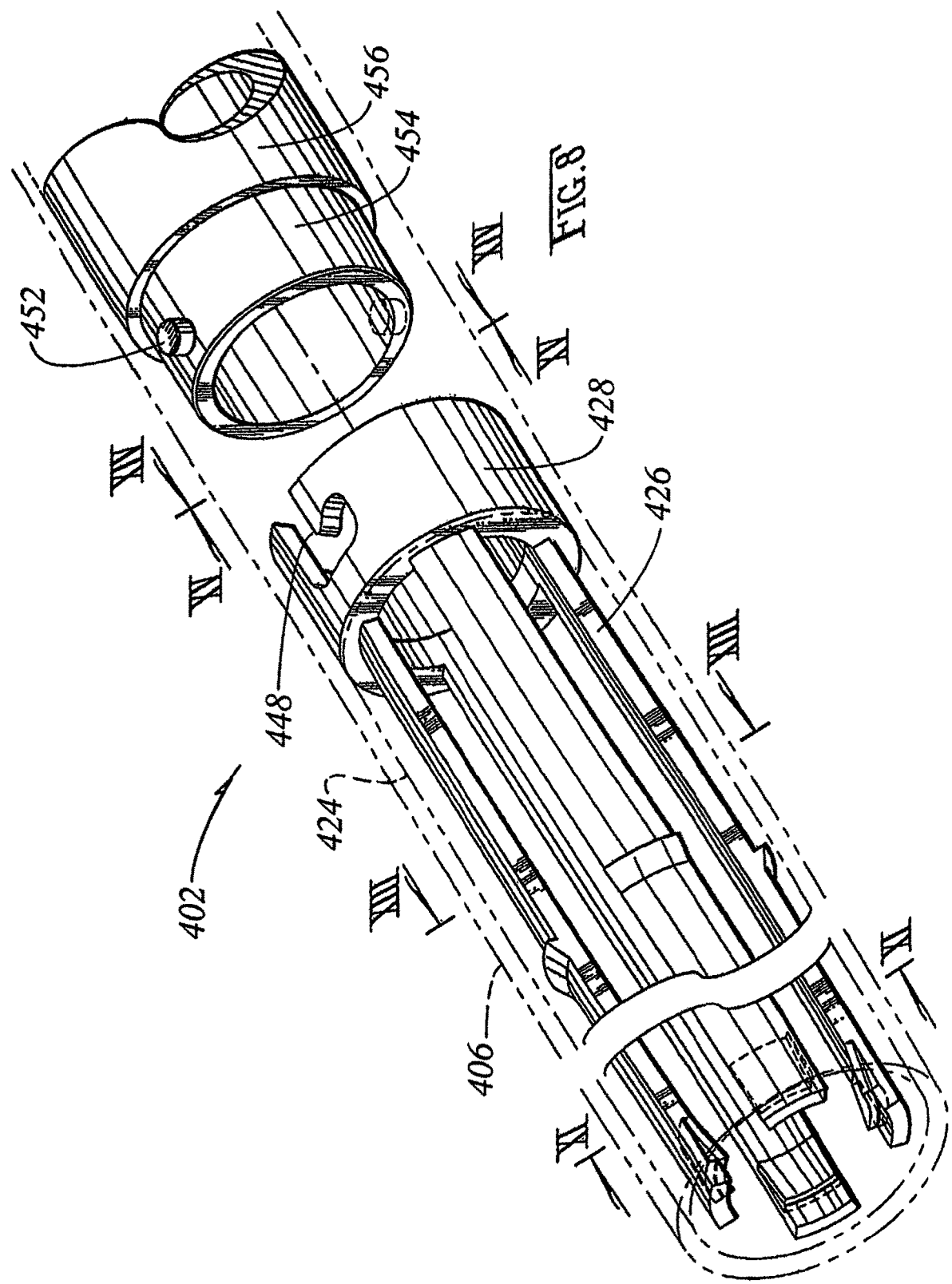
FIG. 8 is an enlarged-scale perspective view of the slide.

FIG. 8 is an enlarged-scale perspective view of the slide 426, shown foreshortened to illustrate better how the ring base 428 of the slide 426 is formed with L-shaped slots 448 typical of bayonet-style connections for coupling with the radially disposed pins 452 on the outside wall 454 of a manually-driven plunger/driver conduit 456, wherein magazine cannister 424 that encircles the slide 426, as well as the slender (and flexible) tubular sidewall 406 of the catheter 402 which encircles all, are both shown in dashed lines.

Hence, at least one axially-elongated arms has a radially-outward projecting detent formed on it. The corresponding axially-elongated groove in the sidewall of the magazine cannister for the at least one-axially elongated arm of the slide ejector is further formed with a relatively deepened but axially-abbreviated section spaced forward of the rear opening of the magazine cannister. The detent has a wedge profile to allow insertion of the ejector slide into the rear opening of the magazine cannister and traverse the axially-elongated grooves therefor until the detent enters the deepened section therefor. After that, the detent reciprocates in the deepened section during extension and retraction strokes of the ejector slide.

The detent has a rear profile and the deepened section has a rear terminus presenting a rear profile wherein the rear profile of the detent and rear profile of the deepened section impede one another so as to impede withdrawal of the ejector slide out of the magazine cannister. Given the foregoing, the deepened section not only allows reciprocation of the detent therein but also enables the detent to interact with the rear profile of the deepened section such that the magazine cannister is effectively tethered to the elongated slender flexible driver conduit and elongated slender flexible plunger. Thus, the cartridge comprising the magazine cannister, the ejector slide and any un-dispensed clips can be withdrawn completely out of the lumen of the elongate flexible endoscopic conduit by withdrawal of the elongated slender flexible driver conduit and elongated slender flexible plunger.

Figure 9:
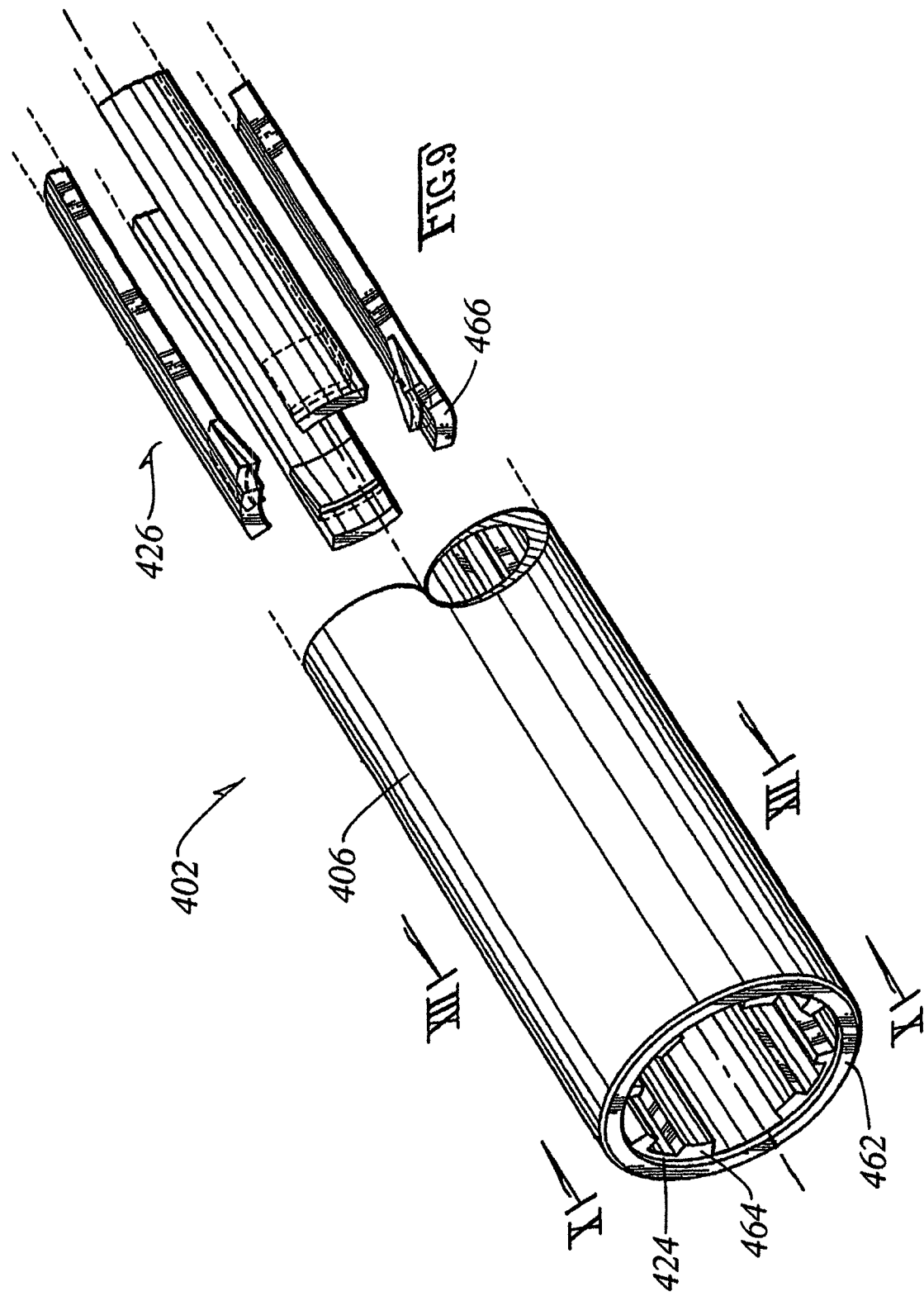
FIG. 9 is an enlarged-scale perspective view of the respective dispensing ends of (i) the tubular sidewall of the catheter and (ii) the magazine cannister (both of which are partly broken away), as well as (iii) the slide ejector, which is also partly broken away but which is moreover illustrated withdrawn from the other two.

FIG. 9 is an enlarged-scale perspective view of the respective dispensing ends 462, 464 and 466, respectively, of (i) the tubular sidewall 406 of the catheter 402 and (ii) the magazine cannister 424 (both of which are partly broken away), as well as (iii) the slide ejector 426, which is also partly broken away but which is moreover illustrated withdrawn from the other two.

Figure 10:
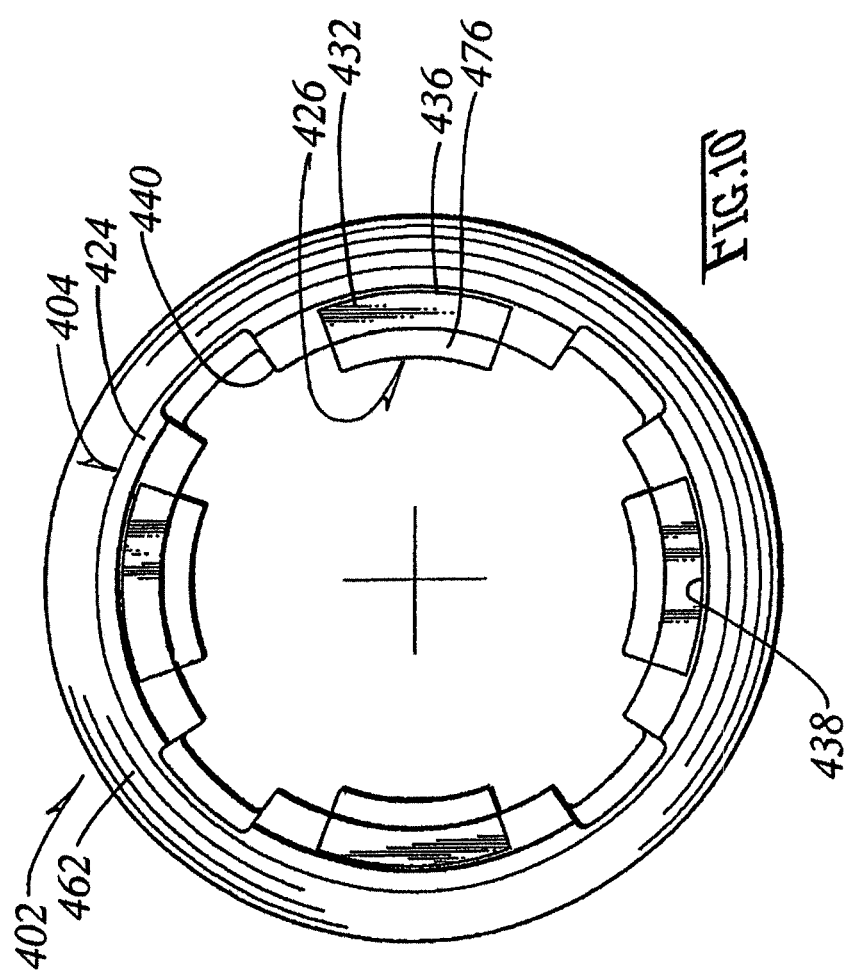
FIG. 10 is an end elevation view taken in the direction of arrows X-X in FIG. 9.

FIG. 10 is an end elevation view taken in the direction of arrows X-X in FIG. 9, and which shows that the magazine cannister 424 has a first set of four channels 438 spaced 90° apart from each other and disposed at the 12 o'clock, 3 o'clock, 6 o'clock and 9 o'clock positions relative to each other, thereby being spaced and sized for the four arms 432 of the slide ejector 426, and which four channels 438 are indeed occupied by a respective one of the arms 432 of the slide ejector 426, and wherein the magazine cannister 424 has a second set of four channels or grooves 440 at the 1:30, 4:30, 7:30 and 10:30 positions of an imaginary clock dial (relative to and without limitation the orientation of FIG. 10), which grooves 440 present a dove-tailed groove profile so as to provide a dove-tailed tongue and dove-tailed groove interaction between the prongs 414 of the clip 400A (not shown) and the grooves 440 therefor in the sidewall 442 of the magazine cannister 424 as described more particularly in connection with FIGS. 22-25.

Figure 11:
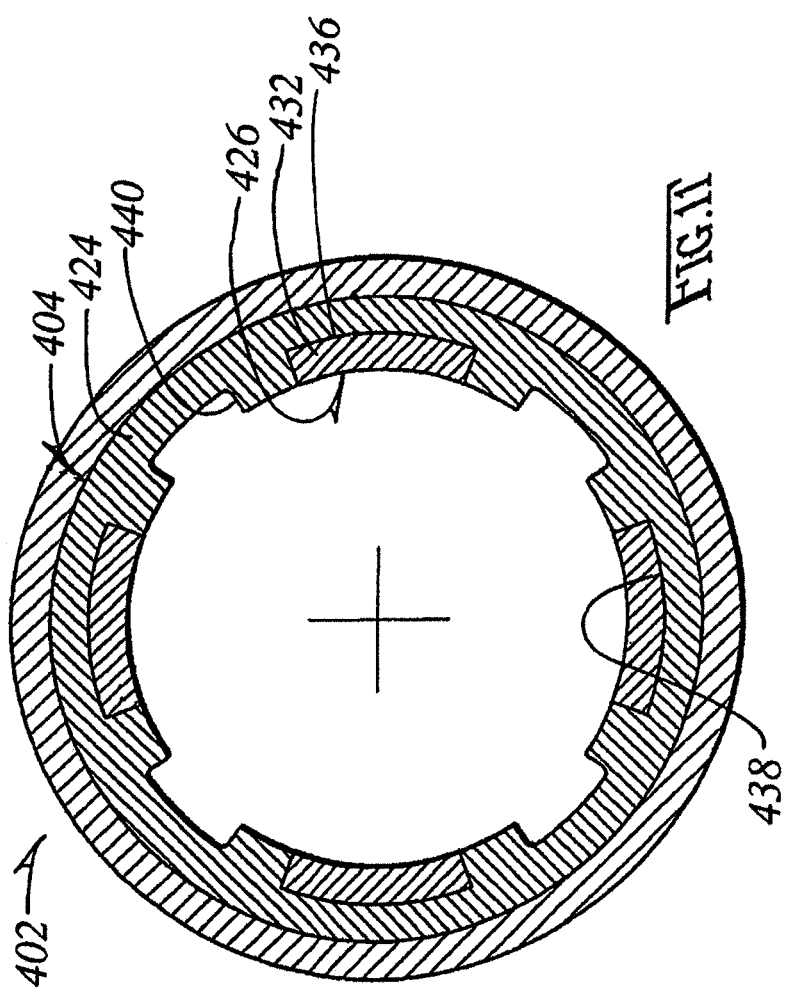
FIG. 11 is a section view taken along line XI-XI of FIG. 8.

FIG. 11 is a section view taken along line XI-XI of FIG. 8 (or, in the alternative, in the reverse direction of the arrows for line XII-XII of FIG. 9), wherein the arms 432 of the slide ejector 426 are in substantial part (in this FIG. 11) depicted in section shading, however, the portions of the arms 432 of the slide ejector depicted as solid line comprise the detents 434 as more particularly described in connection with FIG. 7.

FIG. 12 is a section view taken along line XII-XII of FIG. 9, wherein both the first and second sets of four channels 438 and 440 present a dove-tailed groove profile.

FIG. 13 is a section view taken along line of FIG. 8, and in contrast to FIG. 11 is taken across the deepened sections 444 of the four channels 438 shaped and sized for the four arms 432 of the slide ejector 426 to slide therein, wherein the arms 432 of the slide ejector 426 are in substantial part (in this FIG. 13) depicted in section shading, however, the portions of the arms 432 of the slide ejector 426 depicted as solid comprise the detents 434 as more particularly described in connection with FIG. 7 (ie., the white space between the outer sidewall of the slide arm 432 portions depicted in section shading and the inner sidewall 442 of the magazine cannister 424, also depicted in section shading, is solid depiction of the detents).

FIG. 14 is an end elevation view taken in the direction of arrows XIV-XIV of FIG. 8 and comprising an end elevational view of the ring base 428 of the slide ejector 426 (which hides the rear end of the magazine cannister 424 (not in view) from this vantage point), showing not only the detents 434 of the arms 432 of the slide ejector 426 but also the L-shaped slots 448 typical of bayonet-style connections as more particularly described in connection with FIG. 8, wherein the tubular sidewall 406 of the elongated catheter is minimized in significance in this view by being shown in dashed lines.

FIG. 15 is an end elevation view taken in the direction of arrows XV-XV of FIG. 8 and comprising an end elevational view of the coupling end 468 of the manually-driven plunger/driver conduit 456, showing (among other things) the radial pin 452 placement typical of bayonet-style connections as more particularly described in connection with FIG. 8, wherein the tubular sidewall 406 of the elongated catheter 402 is minimized in significance in the view by being shown in dashed lines.

FIG. 16 is a sectional view of taken along an axial plane of symmetry through FIG. 9, except wherein the slide ejector 426 (ie., it being the third item in the list for the figure description for FIG. 9 above) has been re-united with (i) the tubular sidewall of the catheter 406 and (ii) the magazine cannister 424, wherein this view shows better three more other distinctions (among other distinctions):— the dispensing end 462 of the elongated catheter sidewall 406 terminates in a circular in-turned rim 472 for retaining the magazine cannister 424 from pushing past this rim 472, however, the reciprocation of the slide ejector 426 (which action dispenses the clips 400A (not shown) in the forward stroke and returns to a starting position in the return stroke) does not tend to withdraw the magazine cannister 424 from its abutment with the circular in-turned rim 472 of the catheter sidewall 406 as shown here—that is, the magazine cannister 424 does not tend move back until withdrawn in the manner with the detents 434 described above in connection with FIG. 7, the channels 438 for the arms 432 of the slide ejector 426 remain axially straight all the way through the dispensing end 464 of the magazine cannister 424, while in contrast, the dove-tailed grooves 440 for the prongs (414, not shown) of the clips (400A, not shown) which have a counterpart dove-tailed profile, such dove-tailed grooves 440 in the inner sidewall 442 of the magazine cannister 424 flare outwardly (ie., flare profile indicated by reference numeral 474) at the dispensing end 464 of the magazine cannister 424.

FIG. 17 is a sectional view comparable to FIG. 16 except also including the loading of a column of clips of in accordance with the invention.

FIG. 18 is a section view taken along line XVIII-XVIII in FIG. 17.

FIG. 19 is an enlarged scale section view of detail XIX-XIX in FIG. 16, wherein this view introduces the matter concerning flexible resilient pawls 476, that is, this view shows one of four resilient drive pawls 476 (one drive pawl 476 is formed in each of the four arms 432 of the slide ejector 426), and which drive pawls 476 engage the butt end (418, not shown in this view, but see FIG. 17) of the lead clip (clips are indicated by reference numeral 400A, none shown in this view, but see FIG. 17) in the column to dispense the lead clip when given manual actuation by the plunger (456, not shown in this view).

FIG. 20 is a section view taken along line XX-XX in FIG. 18, wherein FIG. 20 serves to rotate the section views subsequently hereof to a new orientation as shown previously, wherein all section views shown previously had a channel 438 for an arm 432 of the slide ejector 426 shown in the 12 o'clock position, while henceforth, a groove 440 for a prong 414 of a clip 400A will take the 12 o'clock position, the orientation between previous section views and subsequent section views being rotated about 45° counter-clockwise (or 135° and/or 225° or else 315° given the symmetry hereof), and wherein this FIG. 20 shows better the flaring apart (ie., flaring profile 474) of the dove-tailed grooves 440 for the dove-tailed prongs 414 of the clips 400A at the dispensing end 464 of the magazine cannister 424.

FIGS. 21-24 are a series of partial sectional views forming a slideshow and showing the dispensing of the lead clip of the column of clips 400A, and each of these views are comparable to FIG. 17 except the orientation of the section views has been rotated consistent with as described in connection with FIG. 20, whereby:—

Figure 21:
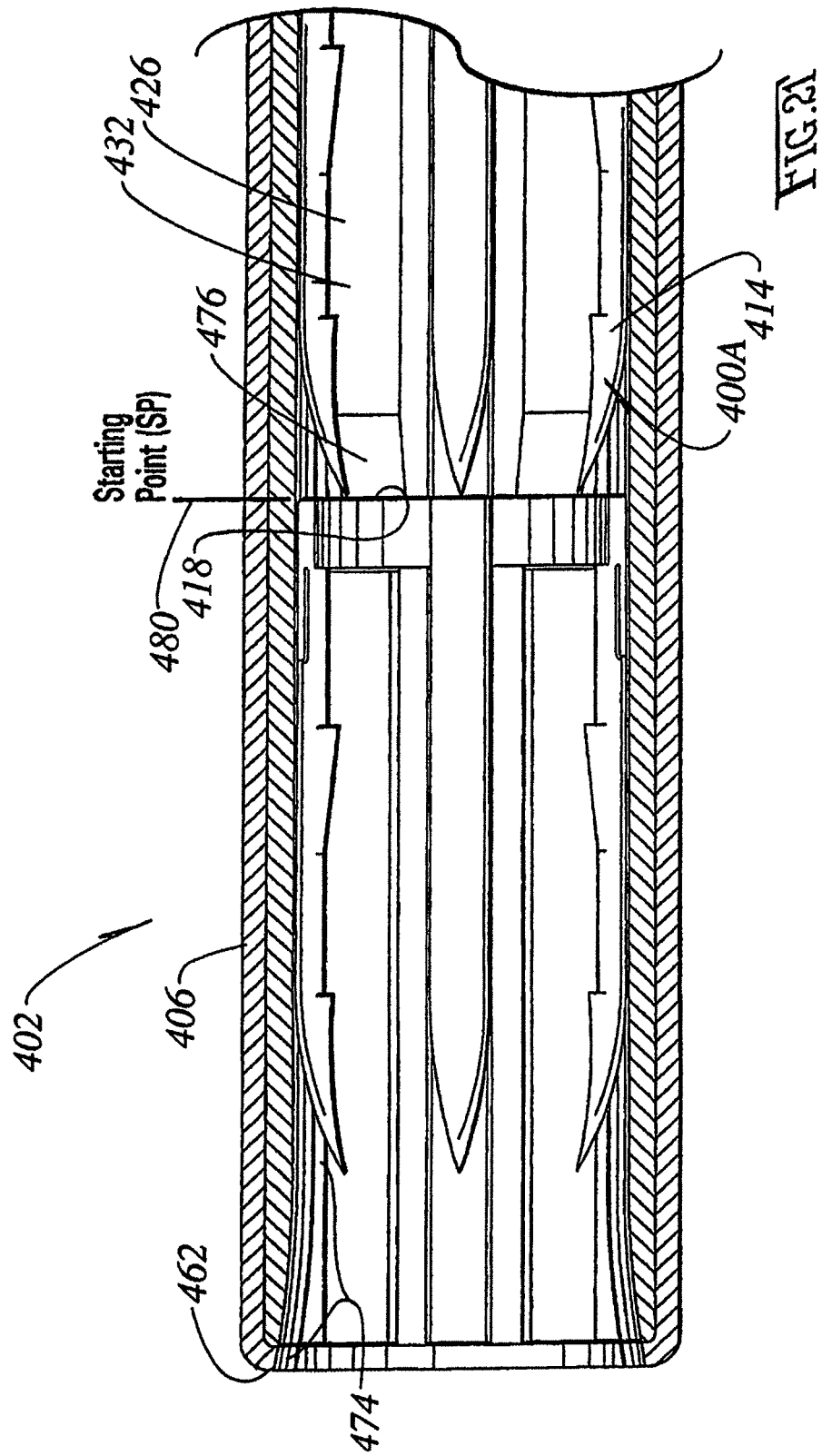
FIGS. 21-24 are a series of partial sectional views forming a slideshow and showing the dispensing of the lead clip of the column of clips, and each of these views are comparable to FIG. 17 except the orientation of the section views has been rotated consistent with as described in connection with FIG. 20; wherein:—
Figure 22:
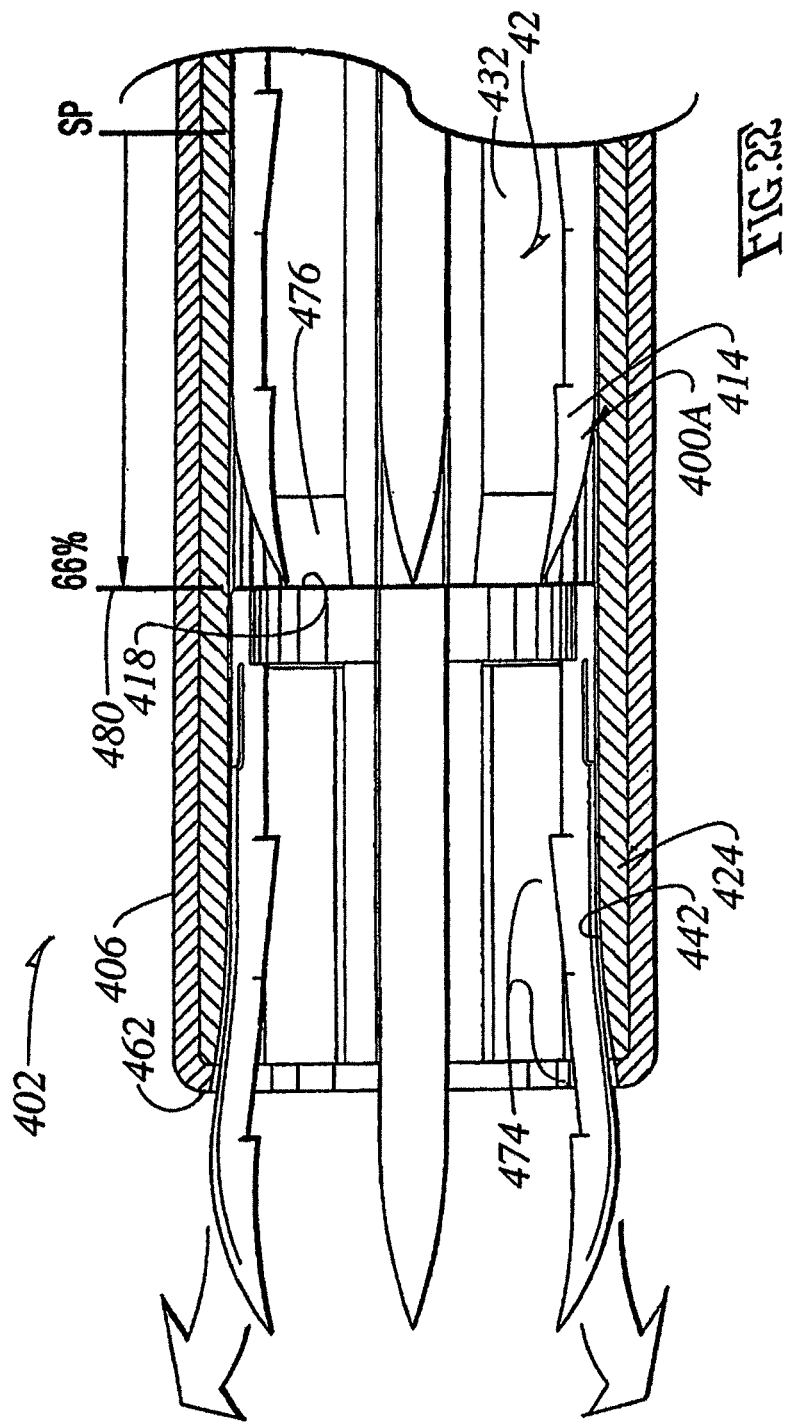
Figure 23:
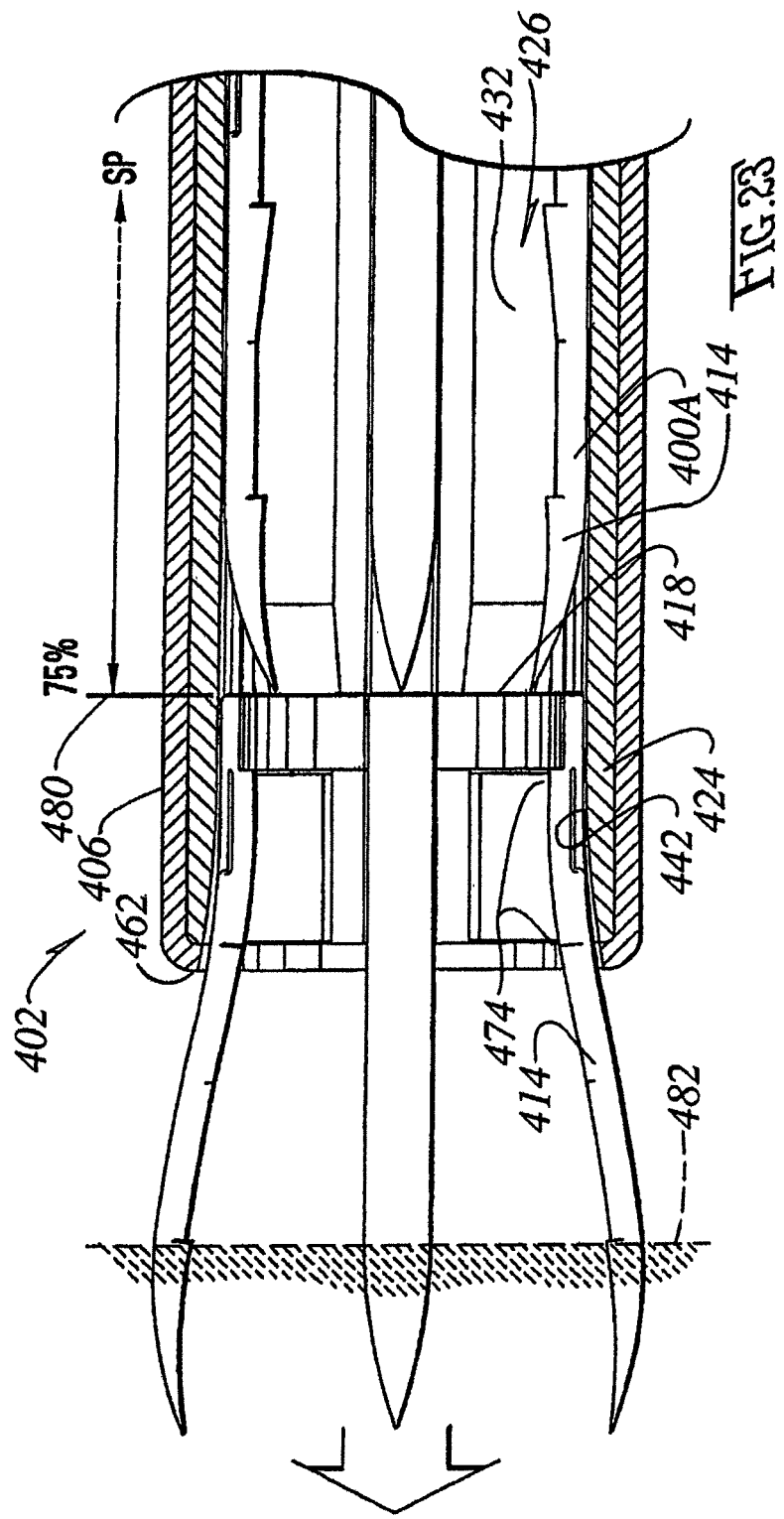
Figure 24:
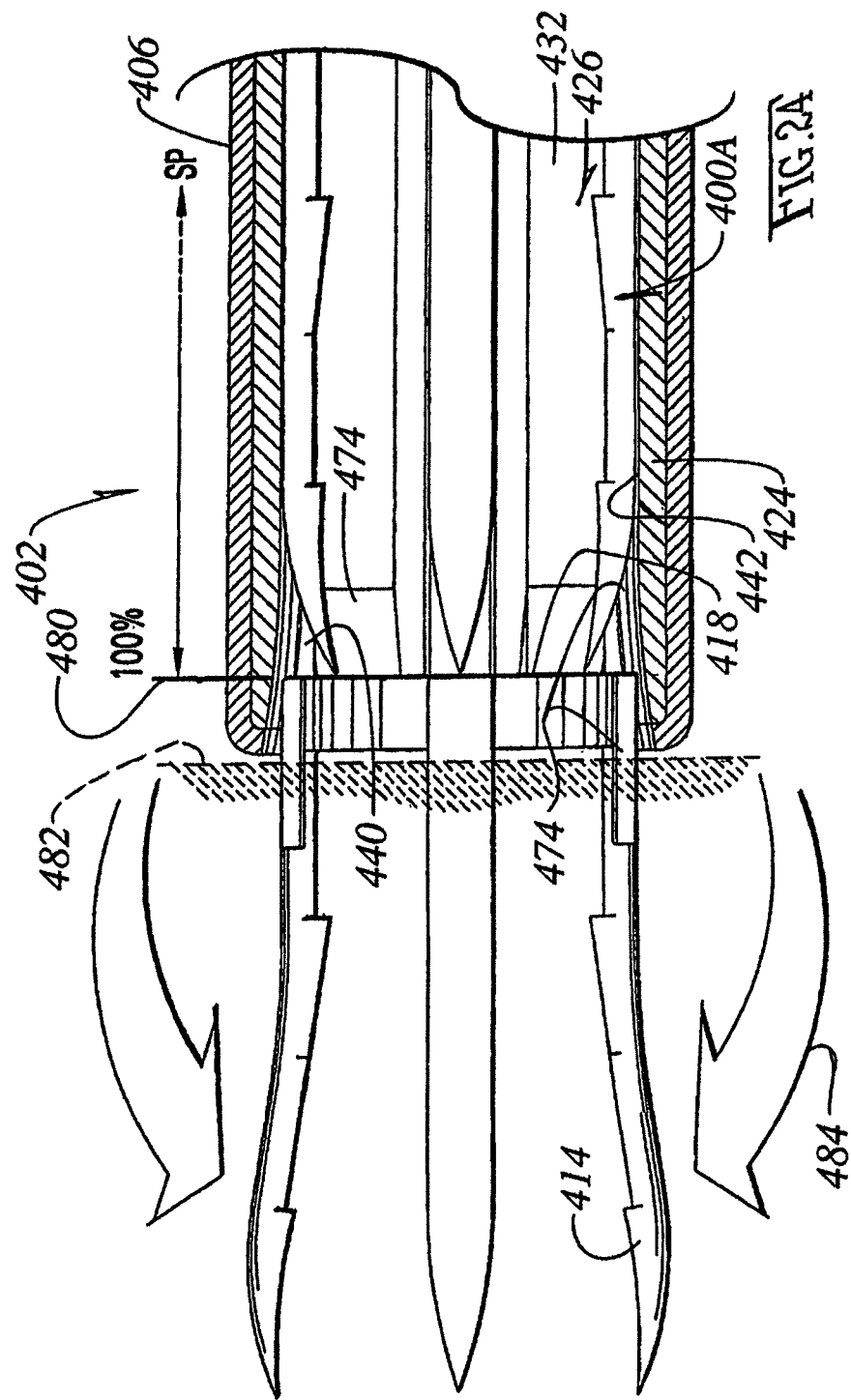

FIG. 21 shows a start position (SP) for the plane 480 at the interface where the drive pawls 476 of the arms 432 of the slide ejector 426 are in engagement with the butt end 418 of the lead clip of the column of clips 400A, and wherein the prongs 414 of the lead clip of the column of clips 400A are pointing straight forward, whereby this start position plane (SP) is a stationary reference plane relative the terminal end of the catheter sidewall 406 (ie., the dispensing end 462 of the catheter 402), FIG. 22 is partial sectional view comparable to FIG. 21 except on a relatively enlarged scale, and except showing that the slide ejector 432 has advanced to about a 66% extension position of its full stroke, as measured by the advancement of the interface 480 where the drive pawls 476 of the arms 432 of the slide ejector 426 are in engagement with the butt end 418 of the lead clip of the column of clips 400A, and wherein the prongs 414 of the lead clip 400A are being forced to flare apart by a dove-tailed tongue and dove-tailed groove interaction between the prongs 414 of the lead clip 400A and the flare profile 474 of the grooves 440 therefor in the sidewall 442 of the magazine cannister 424, FIG. 23 is more or less on the same scale of FIG. 22 and shows that the slide ejector 426 has advanced to about a 75% extension position of its full stroke, as measured by the advancement of the interface 480 where the drive pawls 474 of the slide ejector 426 are in engagement with the butt end 418 of the lead clip of the column of clips 400A, and wherein the prongs 414 of the lead clip are being forced to flare further apart by the aforementioned dove-tailed tongue and dove-tailed groove interaction between the prongs 414 of the lead clip and the flare profiled 474 of the grooves 440 therefor in the sidewall 442 of the magazine cannister 424 (target tissue is indicated by reference numeral 482), and FIG. 24 is also is more or less on the same scale as FIGS. 22 and 23, and shows that the slide ejector 426 has extended to about the end (eg., about the 100% position) of its full stroke, as measured by the advancement of the interface 480 where the drive pawls 474 of the slide ejector 426 are in engagement with the butt end 418 of the lead clip of the column of clips 400A, except that by now the prongs 414 of the lead clip have advanced past the dove-tailed tongue and dove-tailed groove interaction between the prongs 414 of the lead clip and the flared profile 474 of the grooves 440 therefor in the sidewall 442 of the magazine cannister 424, which in consequence releases the prongs 414 to restore themselves inherently their straight-forward pointing position (target tissue is indicated by reference numeral 482).

Figure 25:
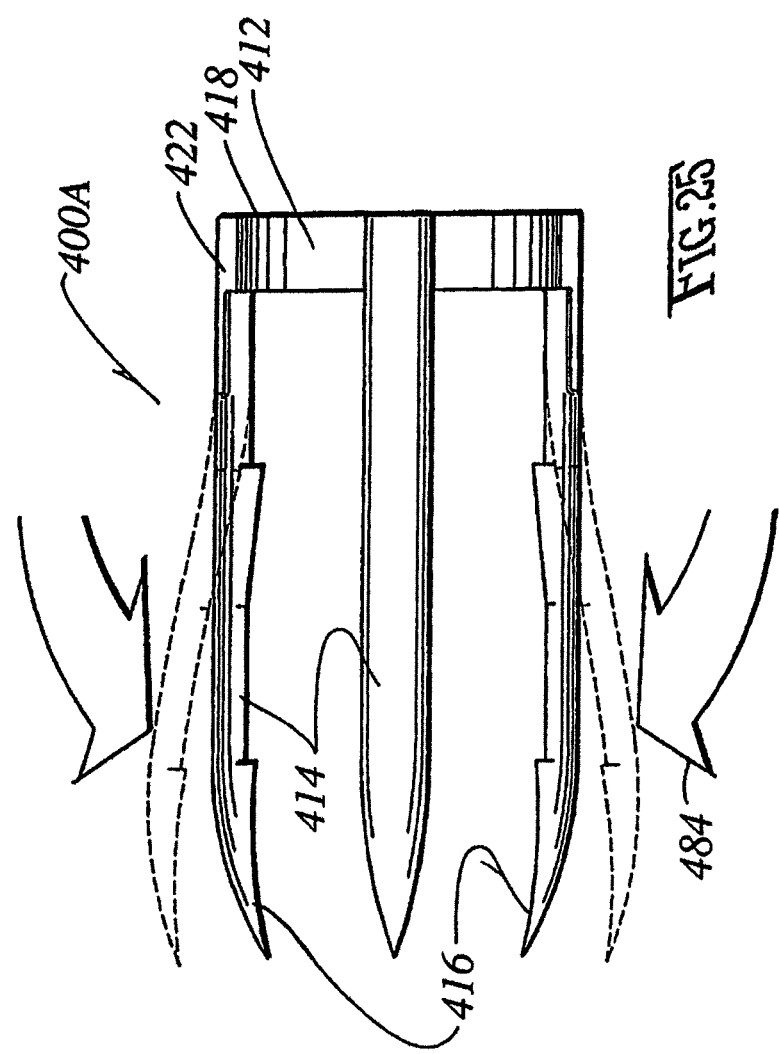
FIG. 25 is a side elevational view of the dispensed lead clip from FIG. 24.

FIG. 25 is a side elevational view of the dispensed lead clip of the column of clips 400A from FIG. 24, it having been released from the dove-tailed tongue and dove-tailed groove interaction between the prongs 414 of the clip 400A and the flared profile 474 of the grooves 440 therefor in the sidewall 442 of the magazine cannister 424, by about some position contemporary with FIG. 23 (the magazine cannister 424 is not shown in this view, only the dispensed lead clip of the column of clips 400A is shown), wherein the open arrows 484 are indicators of the inherent restoring force of the dispensed lead clip 400A to restore its prongs 414 to a more shut position relative to a maximum flared apart position as shown in FIG. 23 (and indicated in dashed lines in this view).

Figure 26:
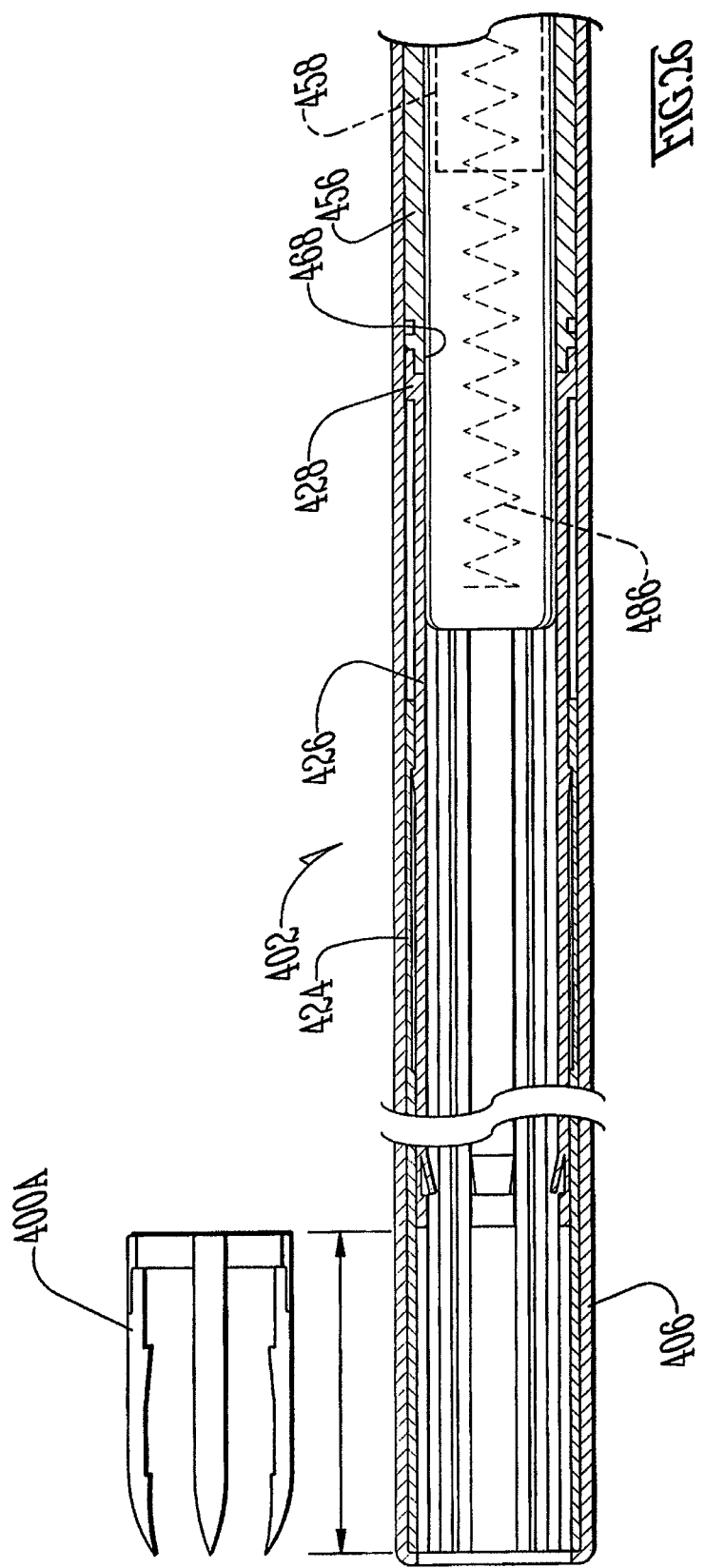
FIG. 26 is section view comparable to FIG. 17, except on a much reduced scale relative to FIG. 17.

FIG. 26 is section view comparable to FIG. 17, except on a much reduced scale relative to FIG. 17, wherein this FIG. 26 has all three of (i) the slide ejector 426, (ii) the magazine cannister 424 and (iii) the catheter sidewall 406 re-rotated back to the angular orientation of FIG. 17 and not FIG. 20 (but it's hard to tell with the catheter sidewall 406), but not the clip 400A:—the clip 400a remains rotated to the angular rotation set by FIG. 20, wherein this FIG. 26 illustrates the bayonet-style connection between the ring base 428 of the slide ejector 426 and the coupling end 468 of the of a driver conduit 456 and manually-driven flexible plunger 458 (see also FIGS. 1A and/or 1B), albeit on a minuscule scale compared to FIG. 8 (which shows the connection uncoupled), and wherein this FIG. 26 further shows that the a driver conduit 456 and manually-driven flexible plunger 458 are hollow, whereby it can be filled with a constantly-urging spring 486 that constantly urges against the butt end 418 of the last-in-line of the column of clips 400A (this is not shown).

FIG. 27 is section view comparable to FIG. 26 except of the driver conduit 456 and manually-actuated plunger 458 of the elongated endoscopic apparatus 402 of FIG. 1, wherein the arrow 488 that corresponds to the length of the stroke also corresponds to the length of one clip 400A (not shown).

FIG. 28 is a perspective view of a second embodiment of a surgery clip 400B in accordance with the invention, wherein this second embodiment 400B has two prongs 414 in contrast with the four prongs of the first embodiment 400A, but still has a comparable dove-tailed tongue and dove-tailed groove interaction between the prongs 414 of this clip 400B and the and the flared profile 474 of the grooves 440 therefor in the sidewall 442 of the magazine cannister 424, as described in connection with FIGS. 22-25.

FIG. 29 is a perspective view of a third embodiment of a surgery clip 400C in accordance with the invention, comprising a single, barbed spike 492.

FIG. 30 is a rear elevational view taken in the direction of arrows XXX-XXX in FIG. 29 clip 400C, showing dove-tailed tabs 494 on the coin-like base 496.

FIG. 31 is a reduced scale perspective view of a column or load-formation of ten such clips 400C as shown in FIG. 29 clip, showing dove-tailed tabs 494 on the coin-like base 496.

FIG. 32 is an enlarged scale detail view (in perspective) of two such clips 400C in the column in FIG. 31.

Figure 33:
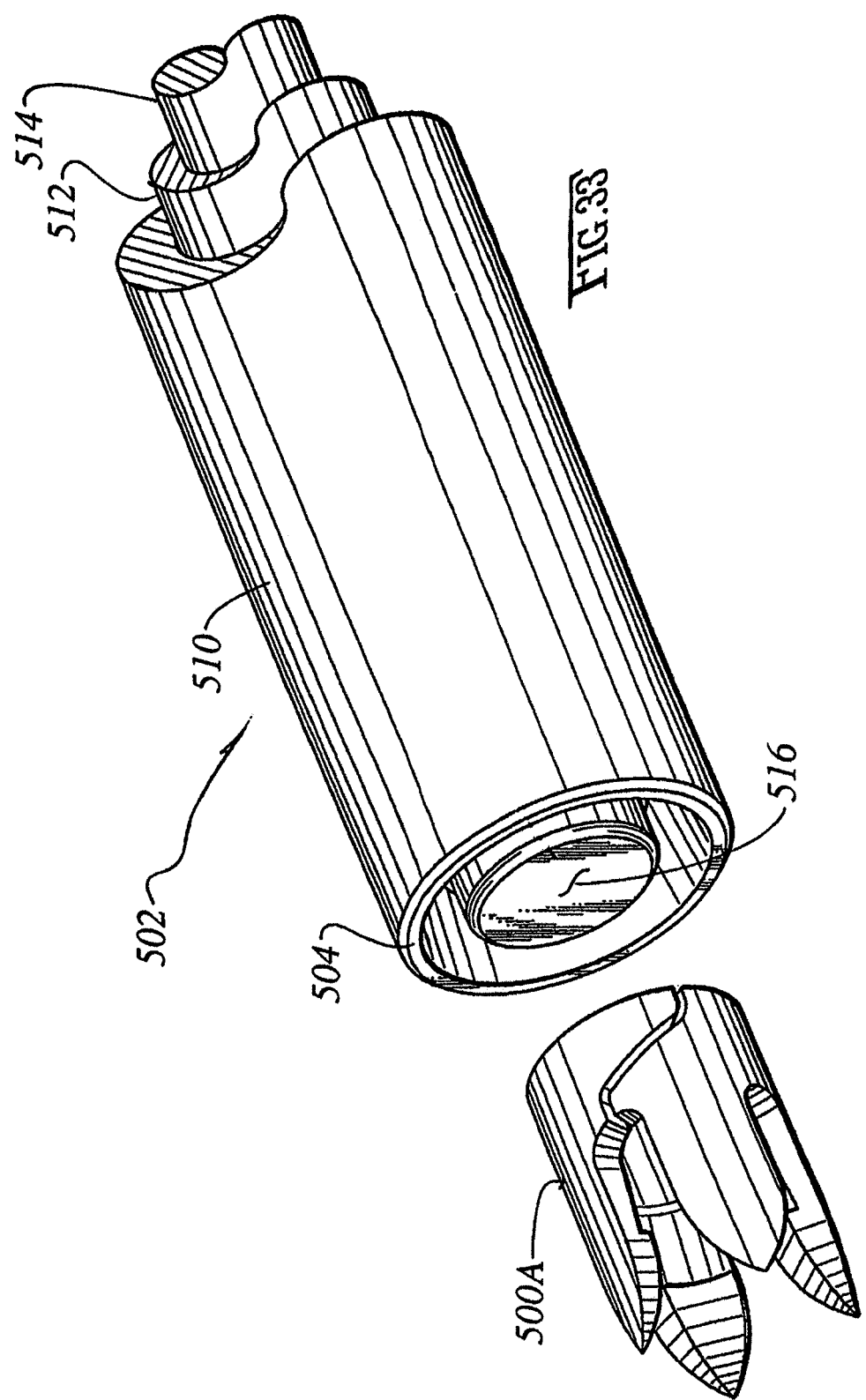
FIG. 33 is a perspective view of a fourth embodiment of a clip in accordance with the invention, while also showing only a second embodiment of a dispensing provision in accordance with the invention.

FIG. 33 is a perspective view of a fourth embodiment of a clip 500A in accordance with the invention, while also showing only a second embodiment of dispensing apparatus 502 in accordance with the invention. This view shows better the terminal end 504 (and dispensing end 504) of the catheter 510 of the dispensing apparatus 502. This catheter 510 is simulative of modern endoscopic apparatus. That is, modern endoscopic apparatus (not shown) would typically have multiple conduits for optics, illumination and so on (again, not shown). It is conventional nowadays that the conduit reserved for clip dispensing is 3 mm inside diameter (~⅛ th of an inch).

Hence the catheter 510 forms the outer ring of three concentric rings:—namely 510, 500A/512 and 514. The middle ring 500A/512 is occupied by both (i) a load of clips 500A and (ii) a plunger/driver conduit 512 which only has a forward stroke. The inner ring 514 is occupied by a stationary (relative to the catheter 510) central strand 514 which has a bulbed terminal end 516 which each clip 500A must pass when being dispensed.

FIG. 34 is a perspective view partly in section comparable to FIG. 33 except showing better the three rings comprising (A) the catheter 510, which is the outer ring, (B) the middle ring occupied by both (i) a column or load of clips 500A and (ii) the a plunger/driver conduit 512 which only has a forward stroke; as well as (C) the central strand 514 which is which terminates in a bulbed terminal end 516 that is stationary relative to the end of the catheter.

FIG. 35 is an enlarged scale perspective view, partly exploded, to show that the central strand 514 threads into (ie., extends centrally through) the hollow lumen of the plunger/driver conduit 512.

FIG. 36 is front elevational view of any of the clips 500A shown in FIGS. 33 and 34.

FIG. 37 is a side elevational view of FIG. 36 and showing the single longitudinal through-slot 518 formed in the cylindrical sidewall 522 of the clip 500A, and extending on an offset (eg., diagonal) track from (a) the web 524 of one of the inter-prong interspaces 526 to (b) the rear end (butt end) 528 of the clip. One preferred size for the clip 500A is 4 mm long by 3 mm outside diameter (ie., the full inside diameter of the catheter 510's hollow passageway therefor).

The clip 500A is essentially a cylindrical spring, such as on the principles of a ring spring for placing on the outside wall of a pipe, or a retainer clip for placing again on the outside wall of a shaft. That is, the clip 500A in accordance with the invention is capable of angularly expanding to travel over the enlarged bulb head 516 of the central strand (see FIGS. 43 through 52). The clip 500A in this FIG. 37 comprise four prongs 532 separated apart by four inter-prong interspaces 526 and protruding forward from a constant thickness slotted collar portion 534.

FIG. 38 is a rear elevational view of FIG. 37 and showing the butt end 528 of the clip 500A, with the single longitudinal through-slot 518 formed therethrough.

FIG. 39 is a side elevational view comparable to FIG. 37 except showing that another preferred size for a clip is clip 500B which is 5 mm long by 3 mm outside diameter (ie., the full inside diameter of the catheter 510's hollow passageway therefor).

FIG. 40 is a side elevational view comparable to FIGS. 37 and 39 except showing that a further preferred size for a clip is clip 500C which is 6 mm long by 3 mm outside diameter (ie., the full inside diameter of the catheter 510's hollow passageway therefor), and so on.

FIG. 41 is an enlarged scale sectional view taken along line XLI-XLI in FIG. 36, and showing that clip 500A has an longitudinally-varying internal contour which preferably includes barbs 544 near the end of the prongs 532.

FIG. 42 is a sectional view comparable FIG. 41 except showing that a longer clip (eg., 500C) may afford opportunity for two barbs 544 and 546 on each prong 532.

FIGS. 43 through 48 comprise a series of comparable sectional views to show the manner in which this version of a dispensing mechanism 502 dispenses this version of a clip 500A, 500B and/or 500C and so on.

Figure 43:
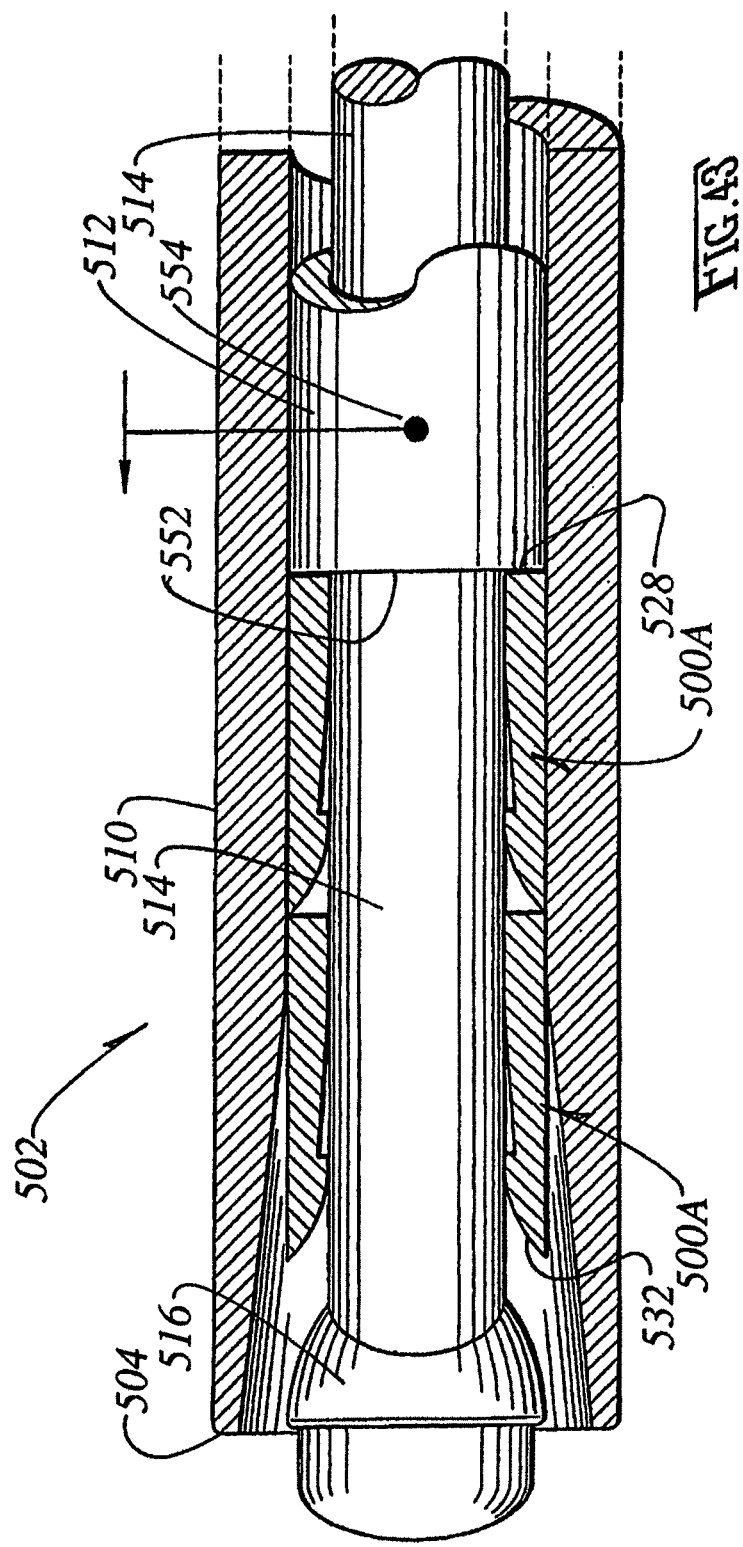

FIG. 43 is a reduced scale partial sectional view of FIG. 34, except in elevation (and with the clip floating out in front of the catheter 510 removed from view). The lead clip is the clip 500A about to be dispensed. The trailing clip 500A has the front rim 552 of the plunger/driver conduit 512 abutted up against this trailing clip 500A's butt end 528. Only two clips 500A are shown in the column but preferably numerous clips could be formed in such a column, preferably and without limitation as many as ten. The plunger/driver conduit 512 is provided with an imaginary target 554 to trace its forward motion during clip dispensing.

FIG. 44 is a partial sectional view comparable to FIG. 43 except showing the plunger/driver conduit 512 driving forward, pushing the trailing clip 500A to ultimately push the lead clip 500A such that the prongs 532 of the lead clip 500A are widened apart by the bulbed head 516 of the central strand 514.

Figure 45:
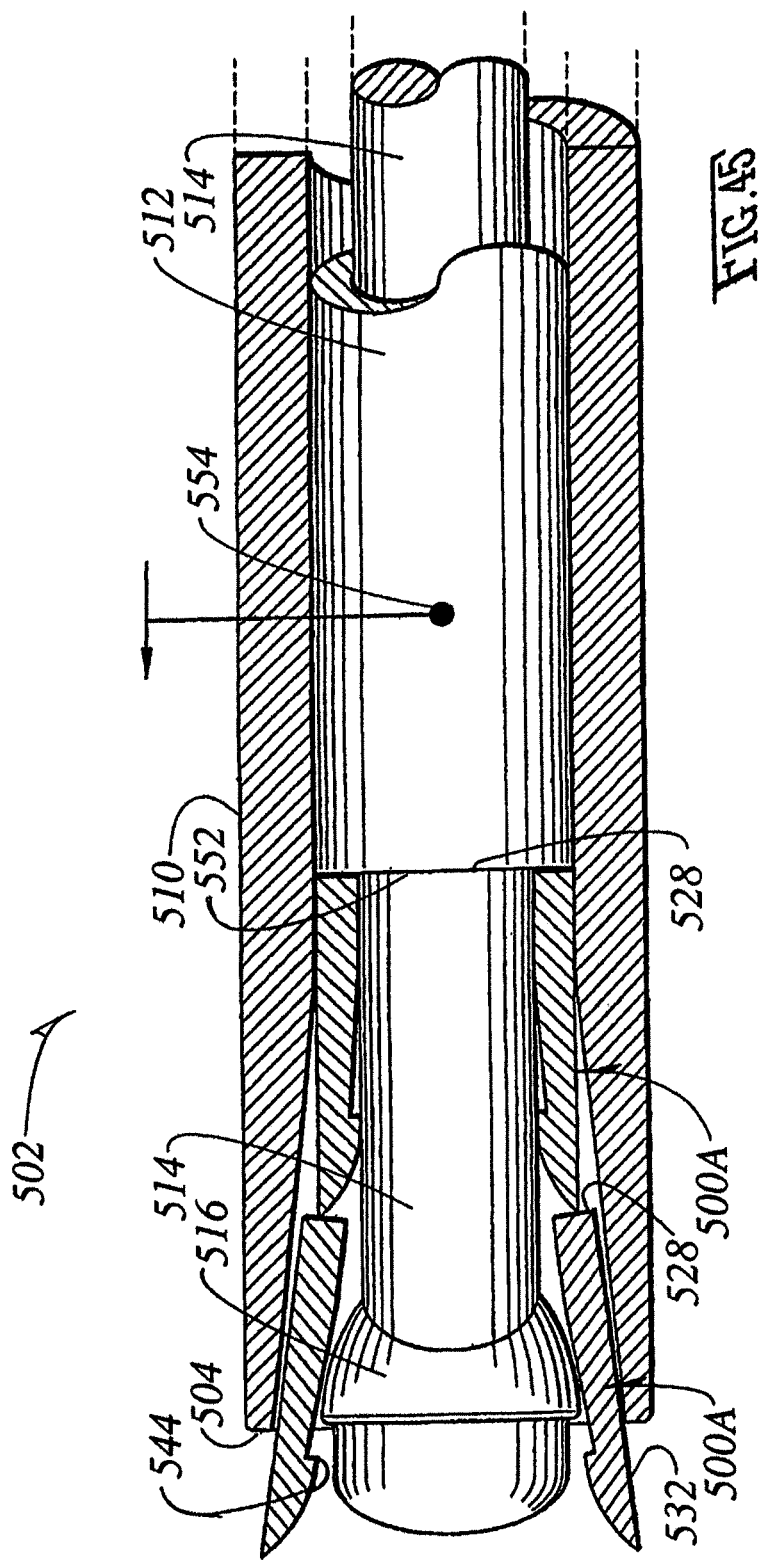

FIG. 45 is a comparable view to FIG. 44 except showing further forward travel of the plunger/driver conduit 512, forcing the lead clip 500A to progress further over the bulbed head 516 of the central strand 514, which the barbs 544 of the prongs 532 have passed across.

Figure 46:
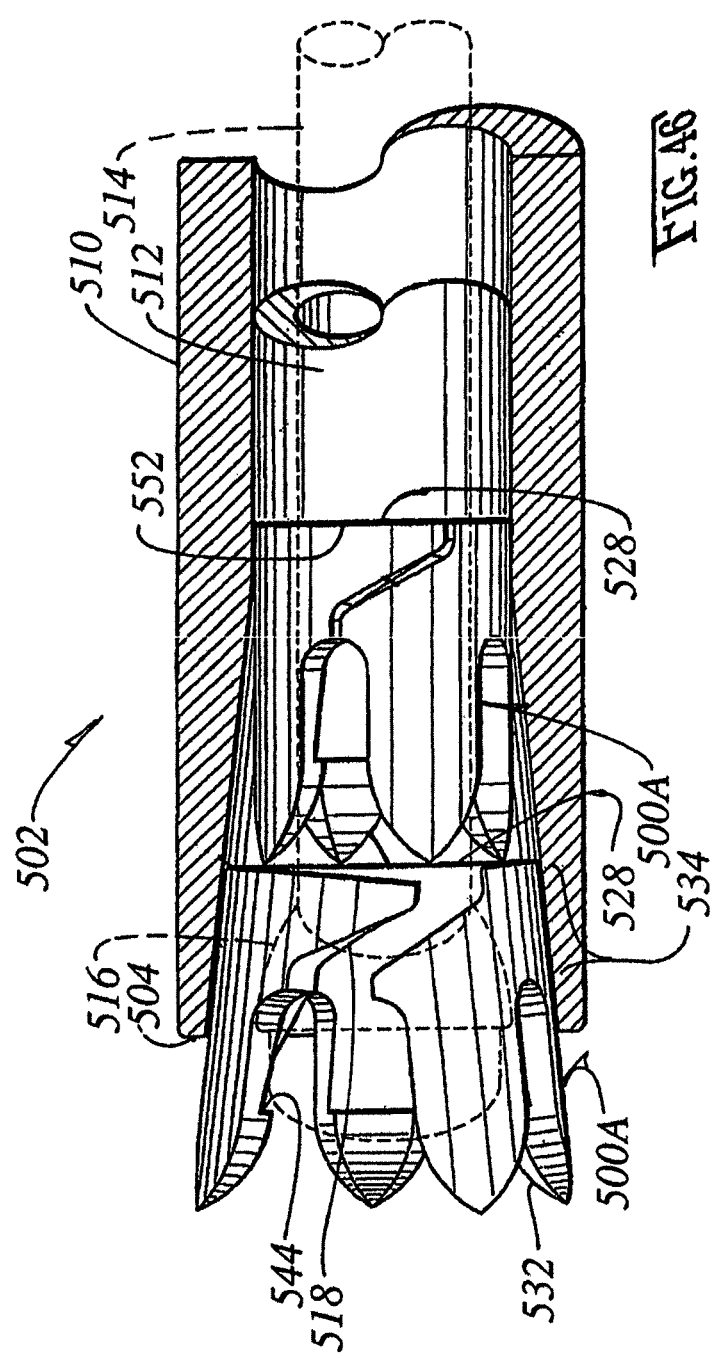

FIG. 46 is a partial sectional view comparable to FIG. 45 except showing the clips 500A in solid line, and showing widening apart of the longitudinal through-slot 518 in the constant-wall thickness, slotted-collar portion 534 of the lead clip 500A. The lead clip 500A's prongs 532 flare apart along an opening conic form. The lead clip 500A's butt end 528's rim warps so that the butt end 528 is not contained in a perpendicular plane to the elongate axis. Instead, the butt end 528 of the lead clip 500A is warped on another conic form that flares out rearwardly, and albeit on a very shallow angle.

FIG. 47 is a view comparable to FIG. 45 except showing the butt end 528 of the lead clip 500A about to pass the widest circumference of the bulbed head 516 of the central strand 514.

FIG. 48, the last in sequence of this series of FIGS. 43-48, shows that the lead clip 500A has at last cleared past the widest circumference of the bulbed head 516 of the central strand 514. The prongs 532 of the lead clip 500A have clenched back into themselves.

FIG. 49 is an elevational view, partly in section, comparable to FIG. 48 except showing that the prongs 532 of the lead clip 500A have not only pierced into tissue 556 (such as for example and without limitation, the stomach wall), but also clenched back into themselves from their former flared out formation. Thus the prongs 532 of the lead clip 500A have clenched and hold in a fast grasp a pinch of tissue 556 as shown (ie., the tissue is represented by the vertical dash line).

FIG. 50 is perhaps a duplicate of FIG. 46. It emphasizes again how the offset (diagonally tracking) through slot 518 enables the lead clip 500A to not only pass over the widest circumference of the bulbed head 516 of the central strand 514, but be flared out along a forward-opening conic form as a whole. The slot 518 does not uniformly widen apart. Instead, the slot 518 widens apart with the opposite side edges on two different helixes of different pitch. In this FIG. 50, it appears if the lower side edge of the slot 518 would align on a coarser screw pitch than the upper side edge.

FIG. 51 is a side elevation view comparable to FIG. 49, again showing the snapping back into toward themselves of the four prongs 532 of the lead clip 500A, pinching the pierced tissue 556 in a fast grasp.

FIG. 52 is a view comparable to FIG. 51 except showing withdrawal of the catheter 510. The plunger/drive conduit (512, but not shown in this view) has been stationary relative to the central strand 514 and catheter 510 since FIG. 51. The plunger/driver conduit (512, again, not shown in this view) does not have a retraction stroke. Instead, the plunger/drive conduit (512, not shown in this view) only has a series of extension (drive) strokes in the increments of the length of one clip 500A at a time. The catheter 510 is immediately available for re-use for dispensing a successive clip 500A.

FIG. 53 shows the preferred result of the clips 500A and dispenser (502, not shown in this view) in accordance with the invention. A wound in a stomach wall 558 is closed by an array of multiple ones of these endoscopic clips 500A in accordance with the invention.

FIG. 53A is an enlarged scale plan view of the detail LIII(A)-LIII(A) in FIG. 53.

FIGS. 54 and 55 are side elevational views comparable to any of FIGS. 37, 39 and 40 (and most particularly closest to FIG. 40), except showing that the (diagonally tracking) through slot 518 shown in FIGS. 37, 39 and 40 can alternatively be given a non-linear course. FIG. 54 shows clip 500D with slot 562. FIG. 55 shows clip 500E with slot 564. That way, the characteristics of how the prongs 532 flare can be manipulated by changing the curvature of the through slot 518, 562 and/or 564.

Figure 57:
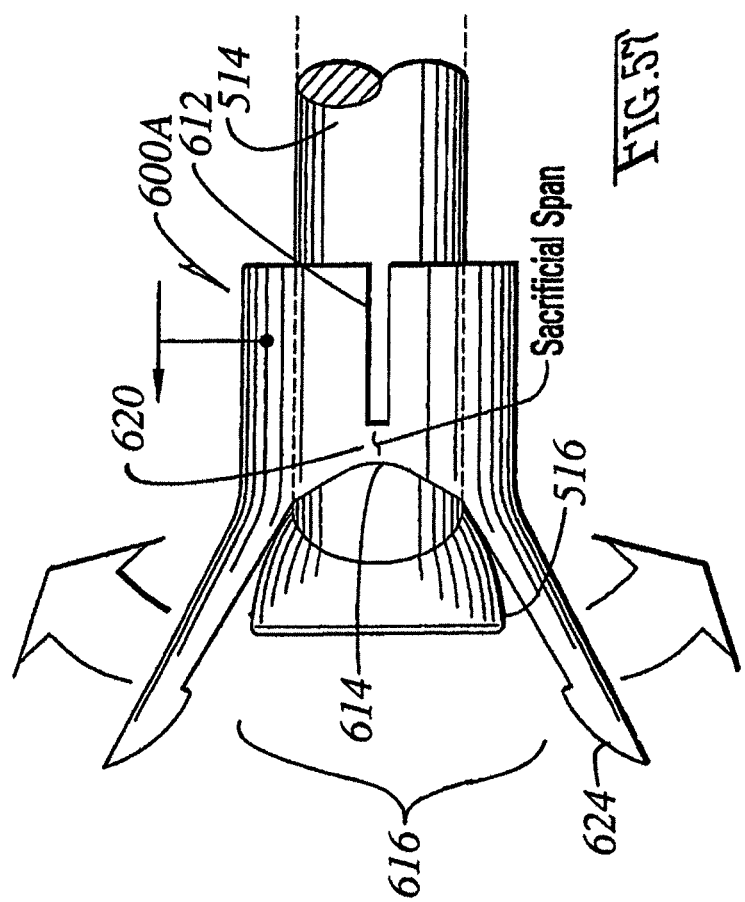

FIGS. 56 through 58 comprise a series of side elevational views showing an alternative embodiment of the a clip 600A in accordance with the invention. Instead of having a through slot with open ends at both ends, the clip 600A has a closed-ended slot 612. Wherein, the open end of slot 518 (not shown here) that formerly opened into the web 614 of the inter-prong inter-space 616 is now closed by a sacrificial span 620.

FIG. 56 shows the clip 600A at rest with the sacrificial span 620.

FIG. 57 shows how the sacrificial span 620 has the effect of forcing the prongs 624 to flare out wider as the prongs transit past the bulbed terminal end 516 of the stationary (relative to the catheter 510, not shown) central strand 514.

FIG. 58 shows how the sacrificial span 620 is eventually severed by the bulbed terminal end 516 of the stationary central strand 514, thereby releasing the prongs 624 to snap shut.

FIGS. 59 through 61 show a plurality of spacers 640 in accordance with invention in alternation with a plurality of clips 600 in the single file line-up loaded in the cartridge.

FIG. 59 is a side elevational view showing a single file series of a clip 600B, then a spacer 640, then a clip 600B again (and so on).

FIG. 60 is a side elevational view comparable to FIG. 59 except showing a shorter clip 600C.

FIG. 61 is a side elevational view comparable to FIGS. 59 and 60 except showing a longer clip 600D than both.

One spacer 640 is inserted between each clip 600. The spacer 640 extends between a leading end 642 and a trailing end 644. The leading end 642 has projecting pin 646. The pin 646 inserts in the back end of the clip 600 just ahead of the spacer 640. The spacer 640's trailing end 644 has a spherical cavity 648 (see FIGS. 60 and 61) formed into it. The prongs 624 of the clip 600 immediately behind the spacer 640 nest in this spherical cavity.

It is an aspect of the invention that the spacer 640 has ends 642 and 644 shaped each independently shaped for the purpose of fitting better the geometries for the front end and back end of the clips 600 respectively.

As FIGS. 60 and 61 show better, the prongs 624 of the clip 600 immediately behind each spacer 640 nest into and push the spacer 640 by abutting in the spherical cavity 648. This drives the lead clip 600 to be dispensed preferably as disclosed by FIGS. 56 through 58. After the lead clip 600 is dispensed, there is a slight possibility that the spacer 640 will remain stuck on the prongs 624 of the clip 600 immediately behind the spacer 640. However, as this trailing clip 600 is cycled through the process of being dispensed, this trailing clip 600's prongs 624 will flare outwardly as shown by FIG. 57. The stuck spacer 640 will have long before this, been flung off.

Hence it is an aspect of the invention that the spacer 640 is self-clearing off the trailing clip 600. Thus the spacer 640 provides geometries to better let each clip 600 be pushed from behind, and to better let the trailing clips 600 in the line to push forwardly. And again, it is a further aspect of the invention that the spacer 640 is self-clearing, before the dispensing (eg., ejection) of the clip 600 behind it.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. Endoscopic apparatus comprising:
    an elongated flexible endoscopic conduit extending between a control end and a dispensing end for endoscopic clip dispensing, said elongated flexible conduit being formed with at least one elongated lumen which likewise extends between the control end and dispensing end, and defining a dispensing end opening and a control end opening, wherein the lumen is characterized by a central axis;
    a slender tubular cartridge extending between a forward dispensing end defining a forward dispensing end opening and a rear control end defining a rear control end opening, and loaded into the lumen through the control end opening of the lumen and advanced through the lumen until the forward dispensing end opening of the cartridge is approximately co-planar with the dispensing end opening of the lumen;
    a plurality of endoscopic clips loaded into the tubular cartridge in series in a single-file line between a lead clip, which will be the first to be dispensed, and a trailing-most clip, which will be the last to be dispensed; and
    an actuator comprising an elongated slender flexible driver conduit and an elongated slender flexible plunger disposed in the lumen and extending between a forward coupling end for coupling with the rear control end of the cartridge and a rear control end connected to a driver disposed outside of the control end opening of the lumen.

2. The endoscopic apparatus of claim 1, wherein:
    the lumen is characterized by a characteristic axial length, the slender cartridge is characterized by a characteristic axial length, and the elongated slender flexible driver conduit and elongated slender flexible plunger are characterized by a characteristic axial length;
    the elongated slender flexible driver conduit and elongated slender flexible plunger couple together in a manner overlapping each other's respective axial lengths over an abbreviated axial-length of overlap between the rear control end of the slender cartridge and the forward coupling end of the elongated slender flexible driver conduit and elongated slender flexible plunger;
    during use, the coupled together slender cartridge and the elongated slender flexible driver conduit and elongated slender flexible plunger occupy the full characteristic axial length of the lumen where—excluding the abbreviated axial-length of overlap between the rear control end of the slender cartridge and the forward coupling end of the elongated slender flexible driver conduit and elongated slender flexible plunger—the characteristic axial length of the slender cartridge represents a minor fraction of the characteristic axial length of the lumen while the characteristic axial length of the elongated slender flexible driver conduit and elongated slender flexible plunger occupies a major, remaining fraction of the characteristic axial length of the lumen.

3. The endoscopic apparatus of claim 2, wherein:
said slender cartridge, when loaded, holds in excess of three (3) clips which can be dispensed independently of each other.

4. The endoscopic apparatus of claim 1, wherein:
the slender cartridge comprises an elongated reciprocating ejector slide and an elongated slender magazine cannister which during use is capable of holding a stationary position in the lumen;
said elongated slender magazine cannister extending between a rear end defining a rear opening and the forward dispensing end of the cartridge;
said ejector slide having at least one axially-elongated arm projecting forwardly from a ring base to a tip end;
said magazine cannister having a sidewall having an inner surface defining a hollow core;
said sidewall being formed with at least one axially-elongated groove recessed through the inner surface, said at least one axially-elongated groove extending from the rear opening of the magazine cannister to the forward dispensing end opening and being provided to allow the at least one axially-elongated arm of the ejector slide to slide therein, whereby the axially-elongated groove promotes the axially-elongated arm from not buckling during extension and retraction strokes.

5. The endoscopic apparatus of claim 4, wherein:
said ejector slide comprises a plurality of axially-elongated arms angularly distributed about the ring base and projecting forwardly to respective tip ends; and
said sidewall of the magazine cannister being formed with complementary plurality of axially-elongated grooves, extending from the rear opening of the magazine cannister to the forward dispensing end opening, and being provided to allow the plurality of axially-elongated arms of the ejector slide to slide therein, whereby promoting the axially-elongated arm s arms from not buckling during extension and retraction strokes.

6. The endoscopic apparatus of claim 5, wherein:
the plurality of axially-elongated grooves have a dove-tailed groove profile and the plurality of axially-elongated arms of the ejector slide have a corresponding dove-tailed tongue profile to provide dove-tailed groove profile to dove-tailed tongue profile interaction during extension and retraction strokes and thereby further promote the axially-elongated arms from not buckling.

7. The endoscopic apparatus of claim 6, wherein:
each clip has a plurality of axially-elongated prongs projecting forwardly from a common base, and angularly distributed about the common base, and extending from the common base to respective tip ends;
said angularly distributed axially-elongated arms being operational within the plurality of axially-elongated grooves therefor to slide past the respective common bases of the plurality of clips during retraction strokes.

8. The endoscopic apparatus of claim 7, wherein:
the plurality of axially-elongated grooves for the axially-elongated arms comprise a first plurality of axially-elongated grooves;
said sidewall of the magazine cannister being formed with a second plurality of axially-elongated grooves for the plurality of axially-elongated prongs of the clips to slide therein, whereby the second plurality of axially-elongated grooves promotes common orientation among the clips relative to the dispensing end opening of the lumen.

9. The endoscopic apparatus of claim 8, wherein:
the prongs of the clips have a dove-tailed tongue profile; and
the second plurality of axially-elongated grooves in the sidewall of the magazine cannister have a counterpart dove-tailed groove profile whereby providing dove-tailed tongue profile to dove-tailed groove profile interaction between the axially-elongated prongs of the clips and the second plurality of axially-elongated grooves of the magazine cannister.

10. The endoscopic apparatus of claim 9, wherein:
each of all of the prongs are characterized by a common, characteristic axial length and are produced of resilient material;
the second plurality of axially-elongated dove-tailed profile grooves are generally parallel to the central axis of the lumen from the rear opening of the magazine cannister to a transition within a fraction of the characteristic axial length of the prongs from the forward dispensing end opening;
the sidewall of the magazine cannister is furthermore formed correspondingly for receiving of the second plurality of axially-elongated dove-tailed profile grooves such that from the transition to the forward open dispensing end the second plurality of axially-elongated dove-tailed profile grooves progressively flare outwardly to a maximum extent in a plane of the forward open dispensing end such that, as the lead clip travels past the transition and ultimately out the open forward dispensing end, the prongs progress from being elongated along axes generally parallel with the central axis of the lumen to being progressively flared radially outwardly between the traverse past the transition and out the open forward dispensing end by dove-tailed groove profile to dove-tailed tongue profile interaction with the flared axially-elongated dove-tailed profile grooves past the transition, until dispensed out the forward dispensing end opening, whereby the prongs are released from the axially-elongated grooves and are free to clench toward one another.

11. The endoscopic apparatus of claim 10, wherein:
the first plurality of axially-elongated grooves for the axially-elongated arms comprise two or more in multiples of twos (2's); and
the second plurality of axially-elongated grooves for the axially-elongated prongs comprise two or more in multiples of twos (2's).

12. The endoscopic apparatus of claim 10, wherein:
the first plurality of axially-elongated grooves for the axially-elongated arms comprise two or more in multiples of twos (2's);
the second plurality of axially-elongated grooves for the axially-elongated prongs comprise four or more in multiples of twos (2's); and the plurality of prongs for each clip comprise two or more in multiples of twos (2's) but not in excess of the second plurality of axially-elongated grooves.

13. The endoscopic apparatus of claim 12, wherein:
the plurality of axially-elongated arms comprises two or four;
the first plurality of axially-elongated grooves for the axially-elongated arms comprise four;
the second plurality of axially-elongated grooves for the axially-elongated prongs comprise four; and
the plurality of prongs for each clip comprise two or four.

14. The endoscopic apparatus of claim 12, wherein:
the first plurality of axially-elongated grooves for the axially-elongated arms are angularly spaced 90° apart from each other; and
the second plurality of axially-elongated grooves for the axially-elongated prongs are angularly spaced 90° apart from each other and staggered in between the first plurality of axially-elongated grooves for the arms.

15. The endoscopic apparatus of claim 10, wherein:
the first plurality of axially-elongated grooves for the axially-elongated arms comprise three or more in multiples of threes (3's); and
the second plurality of axially-elongated grooves for the axially-elongated prongs comprise three or more in multiples of threes (3's).

16. The endoscopic apparatus of claim 4, wherein:
the at least one axially-elongated arms has a radially-outward projecting detent formed thereon;
the at least one axially-elongated groove in the sidewall of the magazine cannister for the at least one-axially elongated arm of the slide ejector is further formed with a relatively deepened but axially-abbreviated section spaced forward of the rear opening of the magazine cannister;
said detent has a wedge profile to allow insertion of the ejector slide into the rear opening of the magazine cannister and traverse the axially-elongated grooves therefor until the detent enters the deepened section therefor, whereafter the detent reciprocates in the deepened section during extension and retraction strokes of the ejector slide;
the detent has a rear profile and the deepened section has a rear terminus presenting a rear profile wherein the rear profile of the detent and rear profile of the deepened section impede one another so as to impede withdrawal of the ejector slide out of the magazine cannister;
whereby the deepened section not only allows reciprocation of the detent therein but also enables the detent to interact with the rear profile of the deepened section such that the magazine cannister is effectively tethered to the elongated slender flexible driver conduit and elongated slender flexible plunger;
whereby the cartridge comprising the magazine cannister, the ejector slide and any un-dispensed clips can be withdrawn completely out of the lumen of the elongate flexible endoscopic conduit by withdrawal of the elongated slender flexible driver conduit and elongated slender flexible plunger.

17. The endoscopic apparatus of claim 16, wherein:
the actuator can advance the cartridge forward through the lumen to a use position after insertion through the control end opening of the endoscopic conduit, and later the actuator can withdraw the cartridge completely out for the loading of a subsequent cartridge, all while the elongated endoscopic conduit is left in place internally in the patient for reloading further clips.

18. Endoscopic apparatus comprising:
an elongated flexible endoscopic conduit extending between a control end and a dispensing end for endoscopic clip dispensing, said elongated flexible conduit being formed with at least one elongated lumen which likewise extends between the control end and dispensing end, and defining a dispensing end opening and a control end opening;
an assembly comprising a slender tubular cartridge and an actuator comprising an elongated slender flexible driver conduit and an elongated slender flexible plunger;
said slender tubular cartridge extending between a forward dispensing end and a rear control end;
in excess of two independently dispensable endoscopic clips loaded into the tubular cartridge in series in a single-file line between a lead clip, which will be the first to be dispensed, and a trailing-most clip, which will be the last to be dispensed;
the elongated slender flexible driver conduit and elongated slender flexible plunger terminating in a forward coupling end for releasably coupling with the rear control end of the cartridge;
portions of said assembly comprise the slender tubular cartridge loaded with the clips along with the elongated slender flexible driver conduit and elongated slender flexible plunger releasably coupled to the rear control end of the slender tubular cartridge, which portions are sized and proportioned to be loaded into the lumen through the control end opening of the lumen and advanced through the lumen until the forward dispensing end of the cartridge is in an operative position relative the dispensing end opening of the lumen, and, withdrawn completely when the last clip is dispensed.

19. The endoscopic apparatus of claim 18, wherein:
the slender cartridge is an eighth (⅛th) or less as long as the elongated slender flexible driver conduit.

20. Endoscopic apparatus comprising:
an elongated flexible endoscopic conduit extending between a control end and a dispensing end for endoscopic clip dispensing, said elongated flexible conduit being formed with at least one elongated lumen which likewise extends between the control end and dispensing end, and defining a dispensing end opening and a control end opening;
an assembly comprising a slender tubular cartridge and an elongated slender flexible driver conduit and an elongated slender flexible plunger;
said slender tubular cartridge extending between a forward dispensing end and a rear control end;
in excess of two independently dispensable endoscopic clips loaded into the tubular cartridge in series in a single-file line;
the elongated slender flexible driver conduit and elongated slender flexible plunger terminating in a forward coupling end for releasably coupling with the rear control end of the cartridge;
said assembly bing sized and proportioned to be loaded into the lumen through the control end opening and advanced through the lumen until the forward dispensing end of the cartridge is in an operative position relative the dispensing end opening of the lumen, and, withdrawn completely after all the clips are dispensed.

* * * * *